(12) United States Patent
Kobayashi et al.

(10) Patent No.: US 9,028,461 B2
(45) Date of Patent: May 12, 2015

(54) PULL-ON WEAR ARTICLE AND METHOD FOR PRODUCING THE SAME

(75) Inventors: Kenji Kobayashi, Utsunomiya (JP); Hayami Ishikawa, Shimotsuga-gun (JP); Junichi Yamashita, Haga-gun (JP)

(73) Assignee: Kao Corporation, Tokyo (JP)

( * ) Notice: Subject to any disclaimer, the term of this patent is extended or adjusted under 35 U.S.C. 154(b) by 17 days.

(21) Appl. No.: 13/976,847

(22) PCT Filed: Dec. 22, 2011

(86) PCT No.: PCT/JP2011/079841
§ 371 (c)(1),
(2), (4) Date: Jun. 27, 2013

(87) PCT Pub. No.: WO2012/090866
PCT Pub. Date: Jul. 5, 2012

(65) Prior Publication Data
US 2013/0281955 A1    Oct. 24, 2013

(30) Foreign Application Priority Data

Dec. 28, 2010 (JP) ................................. 2010-291843
Nov. 7, 2011 (JP) ................................. 2011-243227

(51) Int. Cl.
*A61F 13/496* (2006.01)
*A61F 13/514* (2006.01)
(Continued)

(52) U.S. Cl.
CPC ..... *A61F 13/49012* (2013.01); *A61F 13/49011* (2013.01); *A61F 13/4902* (2013.01); *A61F 13/496* (2013.01); *A61F 13/15699* (2013.01); *A61F 13/15593* (2013.01)

(58) Field of Classification Search
CPC .................... A61F 13/49011; A61F 13/49012; A61F 13/496; A61F 13/49061; A61F 13/49019; A61F 13/49038
See application file for complete search history.

(56) References Cited

U.S. PATENT DOCUMENTS

2004/0010241 A1* 1/2004 Sanders et al. ........... 604/385.24
2005/0107763 A1 5/2005 Matsuda et al.
(Continued)

FOREIGN PATENT DOCUMENTS

JP    62-199808 A    9/1987
JP    8-38546 A      2/1996
(Continued)

OTHER PUBLICATIONS

International Search Report for PCT/JP2011/079841 mailed on Apr. 3, 2012.
(Continued)

*Primary Examiner* — Susan Su
(74) *Attorney, Agent, or Firm* — Birch, Stewart, Kolasch & Birch, LLP

(57) ABSTRACT

A pull-on wear article having a front portion that is adapted to be worn around the front side of a wearer, a crotch portion that is adapted to be worn along the wearer's crotch region, and a rear portion that is adapted to be worn around the wearer's rear side, which is formed into a pants form by bonding lateral side edges of the front portion and lateral side edges of the rear portion, wherein the front portion and the rear portion are each constituted by an outer cover in which an inner layer material and an outer layer material are laminated, the outer cover has plural single layer areas that are formed of the inner layer material or the outer layer material at intervals in the direction of length of the outer cover, and the laminate areas where the inner layer material and outer layer material are laminated have elasticity in the waist-surrounding direction of the outer cover.

5 Claims, 31 Drawing Sheets

(51) Int. Cl.
  *A61F 13/49*  (2006.01)
  *A61F 13/15*  (2006.01)

(56) References Cited

U.S. PATENT DOCUMENTS

| | | | |
|---|---|---|---|
| 2005/0131374 A1* | 6/2005 | Otsubo et al. | 604/385.27 |
| 2005/0131379 A1* | 6/2005 | Otsubo et al. | 604/387 |
| 2006/0244166 A1 | 11/2006 | Wada et al. | |
| 2010/0059168 A1* | 3/2010 | Endo et al. | 156/164 |
| 2010/0106123 A1 | 4/2010 | Fukae | |
| 2011/0098668 A1* | 4/2011 | Thorson et al. | 604/385.25 |
| 2012/0310193 A1* | 12/2012 | Ostertag | 604/365 |
| 2013/0046266 A1* | 2/2013 | Kawakami | 604/385.3 |
| 2013/0060219 A1* | 3/2013 | Mukai et al. | 604/385.3 |
| 2013/0165890 A1* | 6/2013 | Glaug et al. | 604/385.16 |
| 2013/0289513 A1* | 10/2013 | Takino | 604/385.25 |

FOREIGN PATENT DOCUMENTS

| | | |
|---|---|---|
| JP | 10-137288 A | 5/1998 |
| JP | 2002-273808 A | 9/2002 |
| JP | 2003-38556 A | 2/2003 |
| JP | 2005-279077 A | 10/2005 |
| JP | 2007-509725 A | 4/2007 |
| JP | 2008-508082 A | 3/2008 |
| JP | 2008-131968 A | 6/2008 |
| JP | 2008-132023 A | 6/2008 |
| JP | 2008-136793 A | 6/2008 |
| JP | 2008-142341 A | 6/2008 |
| JP | 2008-161514 A | 7/2008 |
| JP | 2008-178682 A | 8/2008 |
| JP | 2008-194160 A | 8/2008 |
| JP | 2008-307272 A | 12/2008 |
| JP | 2009-106666 A | 5/2009 |
| JP | 2009-153841 A | 7/2009 |
| JP | 2009-160128 A | 7/2009 |
| JP | 2009-195647 A | 9/2009 |
| JP | 2010-158590 A | 7/2010 |
| JP | 2011-25006 A | 2/2011 |
| JP | 4659109 B2 | 3/2011 |
| WO | WO 2004/054490 A1 | 7/2004 |
| WO | WO 2006/017718 A1 | 2/2006 |
| WO | WO 2008/108270 A1 | 9/2008 |

OTHER PUBLICATIONS

International Preliminary Report on Patentability and Translation of the Written Opinion of the International Searching Authority, dated Feb. 23, 2012, for International Application No. PCT/JP2010/060991.

International Search Report, dated Sep. 28, 2010, for International Application No. PCT/JP2010/060991.

* cited by examiner

The arrows represent the conveying directions.

FIG. 31
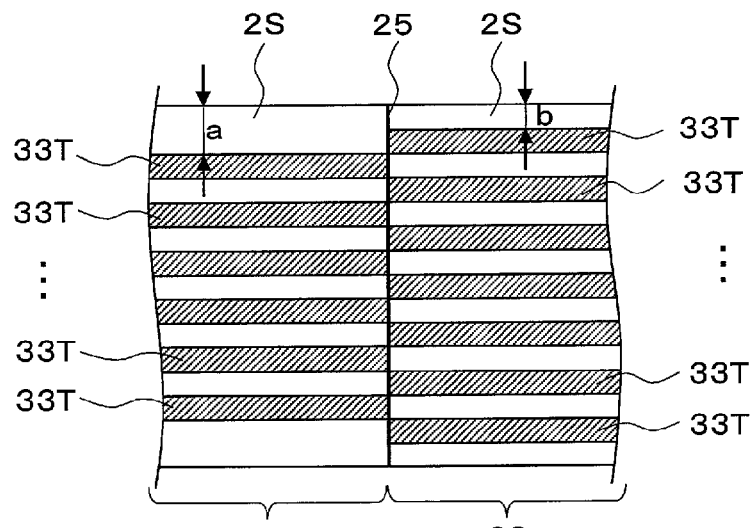
(1)
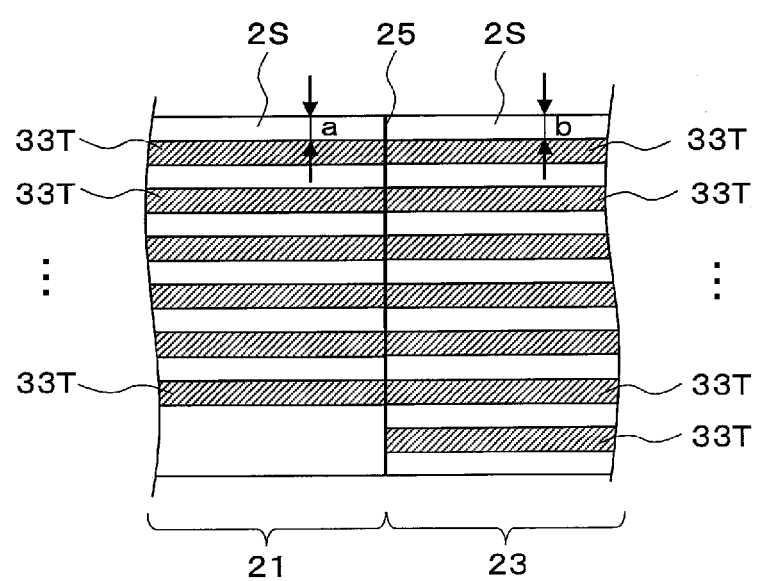
(2)

PULL-ON WEAR ARTICLE AND METHOD FOR PRODUCING THE SAME

FIELD OF THE INVENTION

The present invention relates to a pull-on (pants type) wear article, and a method for producing the same.

BACKGROUND OF THE INVENTION

As a conventional pull-on diaper, a pull-on diaper is known that comprises an outer cover adapted to be worn around the front side and rear side of a wearer, and a crotch portion adapted to be worn along the wearer's crotch, which is arranged between the front side and rear side of the outer cover, wherein an absorbent body is disposed on the crotch portion (for example, see Patent Literatures 1 and 2).

The outer cover has a two-layer structure of an inner layer material and an outer layer material laminated over almost their entire surfaces, and a sheet in which the inner layer material and outer layer material are attached to each other through an interposed elastic element is used to constitute the outer cover. This sheet is divided in two widthwise, and an absorbent body is disposed so as to link the divided sheet portions in parallel, the outer edge portions of the outer layer materials constituting the sheets are respectively folded, and the both edge portions of the absorbent body are fixed by the folded portions. Subsequently, the absorbent body is folded in the vicinity of the central portion and the sheets are superposed so that the inner layer material comes to the inside, and the sheets that are superposed so as to interpose the absorbent body therebetween are bonded at predetermined intervals in the lateral direction. Thereafter the central portion of the bonded portion is cut in the lateral direction of the sheets and the cut portions are separated off. By this way, a pull-on diaper comprising an outer cover formed by bonding sheets, and an absorbent body fixed on this outer cover is completed (for example, see Patent Literature 1).

Another disclosed structure comprises an integral outer cover sheet that covers from a front body to a rear body; band-like sheet materials extending in the lateral direction, which are plurally disposed in a staggered arrangement in the longitudinal direction on the outer surface of the outer cover sheet; and an elastic-stretchable element under waist that also acts as a gathered elastic-stretchable element, which is interposed into an edge portion on the waist side of the superposed portions of the band-like sheet substrates and outer cover sheet and fixed by a hot-melt adhesive or the like (for example, see Patent Literature 3). Since each edge portion on the crotch side in the CD direction (the lateral direction at right angles to the line flow direction) of the band-like sheet materials is disposed so as to cover another band-like sheet substrate whereunder, the outer cover sheet as a whole has a two-layer structure comprising at least the outer cover sheet and band-like sheet materials (the outer cover sheet has a three layer structure at the superposed portion of the band-like sheet materials). A method for producing this comprises continuously interposing the elongated elastic-stretchable element between the outer cover sheet and band-like sheet substrates, and, at the same time, fixing the elastic-stretchable element to the edge portions of the waist side of the band-like sheet substrates using a hot-melt adhesive. Therefore, it is necessary to dispose the respective band-like sheet materials in a staggered arrangement so that the respective band-like sheet substrates are partially overlapped, and thus the positional accuracy of the band-like sheet materials with respect to the elongated elastic-stretchable elements is important.

CITATION LIST

Patent Literatures
Patent Literature 1: JP-A-2005-279077 ("JP-A" means unexamined published Japanese patent application)
Patent Literature 2: JP-T-2008-508082 ("JP-T" means published searched patent publication)
Patent Literature 3: Japanese Patent No. 4659109

SUMMARY OF THE INVENTION

Pull-on diaper users want usability like that of underwear, and desire further improvement of the flexibility and air permeability because conventional pull-on diapers have an outer cover of a two-layer structure whose inner layer material and outer layer material are laminated over almost the whole surface. Specifically, this is most likely in the case where an embossed sheet such as spabond fabrics is used. Furthermore, a structure in which band-like sheet materials to serve as waist frill elements are disposed in the longitudinal direction has a two-layer structure or a three-layer structure, so that further improvement of air permeability is desired.

The present invention relates to a pull-on wear article that solves the problem of steaminess during wearing by softening a waist-surrounding area of an outer cover of a pull-on diaper and improving the air permeability thereof. Furthermore, the present invention relates to a method for producing a pull-on wear article on which tape-type sheet materials (band-like sheet materials), which are formed by cutting a sheet such as a nonwoven fabric in narrow widths, are stably disposed at predetermined intervals with fine accuracy in the case when where tape-type sheet materials are fixed thereon.

Solution to Problem

The present invention resides in a pull-on wear article comprising a front portion that is adapted to be worn around the front side of a wearer, a crotch portion that is adapted to be worn along the wearer's crotch region, and a rear portion that is adapted to be worn around the wearer's rear side, wherein lateral side edges of the front portion and lateral side edges of the rear portion are bonded to thereby form a pants shape. The front portion and the rear portion are each constituted by an outer cover obtained by laminating an inner layer material and an outer layer material, and the outer cover has plural single layer areas formed of the inner layer material or the outer layer material, wherein the plural single layer areas are disposed at intervals in the direction of length of the outer cover, and the laminate areas where the inner layer material and the outer layer material are laminated have elasticity in the waist-surrounding direction of the outer cover.

Furthermore, the present invention resides in a method for producing a pull-on wear article. The method for producing a pull-on wear article of the present invention comprises:
a step of slitting a first sheet material for constituting an outer cover at plural points in a lateral direction to thereby form plural pieces of tape-type sheet materials;
a step of laminating and fixing the plural pieces of tape-type sheet materials at spaced intervals with second sheet materials to give the outer cover;
a step of orienting the second sheet materials to face inward and thereby overlapping the outer cover and bonding the overlapped outer cover at a predetermined interval in the lateral direction of the outer cover; and a step of cutting the outer cover at the bonded portions in the lateral direction.

The present invention resides in a method for producing a pull-on wear article. The method for producing a pull-on wear article of the present invention comprises:

a step of slitting a first sheet material for constituting an outer cover at plural points in a lateral direction to form plural pieces of tape-type sheet materials;

a step of conveying the plural pieces of tape-type sheet materials alternately in different directions while maintaining the positions in the lateral direction during the slitting to thereby separate the tape-type sheet materials into tape-type sheet materials for a front side and tape-type sheet materials for a rear side;

a step of laminating and fixing the respective tape-type sheet materials for the front side and for the rear side with separate second sheet materials for the front side and rear side while maintaining the positions in the lateral direction during the slitting to give an outer cover continuous element to be disposed on the front portion and an outer cover continuous element to be disposed on the rear portion;

a step of adjusting their positions of the outer cover continuous element to be disposed on the front portion and the outer cover continuous element to be disposed on the rear portion to give a predetermined interval;

a step of fixing an absorbent body so as to bridge between the outer cover continuous element to be disposed on the front portion and the outer cover continuous element to be disposed on the rear portion;

a step of orienting the second sheet materials to face inward and thereby overlapping the outer cover continuous element to be disposed on the front portion and the outer cover continuous element to be disposed on the rear portion, and bonding the outer cover continuous elements at a predetermined interval in the lateral direction; and a step of cutting the outer cover continuous elements in the lateral direction at the bonded portions.

BRIEF DESCRIPTION OF THE DRAWINGS

FIG. 31 shows a side view of the main portion showing an example of the positional relationship between the tape-type sheet materials and the second sheet materials for the front portion and the rear portion, on both sides of the side seal portion of the pull-on wear article of the present invention.

DESCRIPTION OF EMBODIMENTS

A preferable embodiment (the first embodiment) of the pull-on wear article according to the present invention will be explained below, referring to the perspective view shown in FIG. 1 and the exploded perspective view shown in FIG. 2.

In the pull-on wear articles 10 and 100 in this description, the direction of length of the pull-on wear article is defined as Y direction, and the lateral direction of the pull-on wear article is defined as X direction and also referred to as "waist-surrounding direction".

Figure 1:
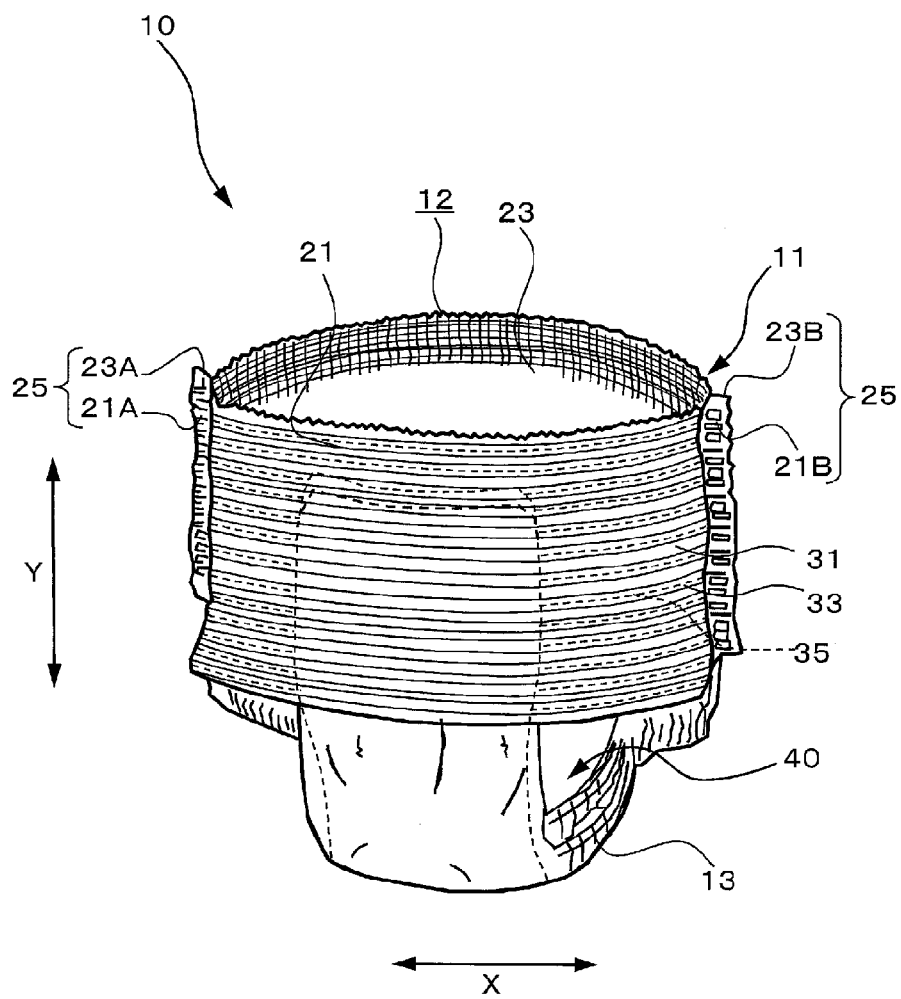
FIG. 1 is a perspective view showing a preferable embodiment (the first embodiment) of the pull-on wear article of the present invention.
Figure 2:
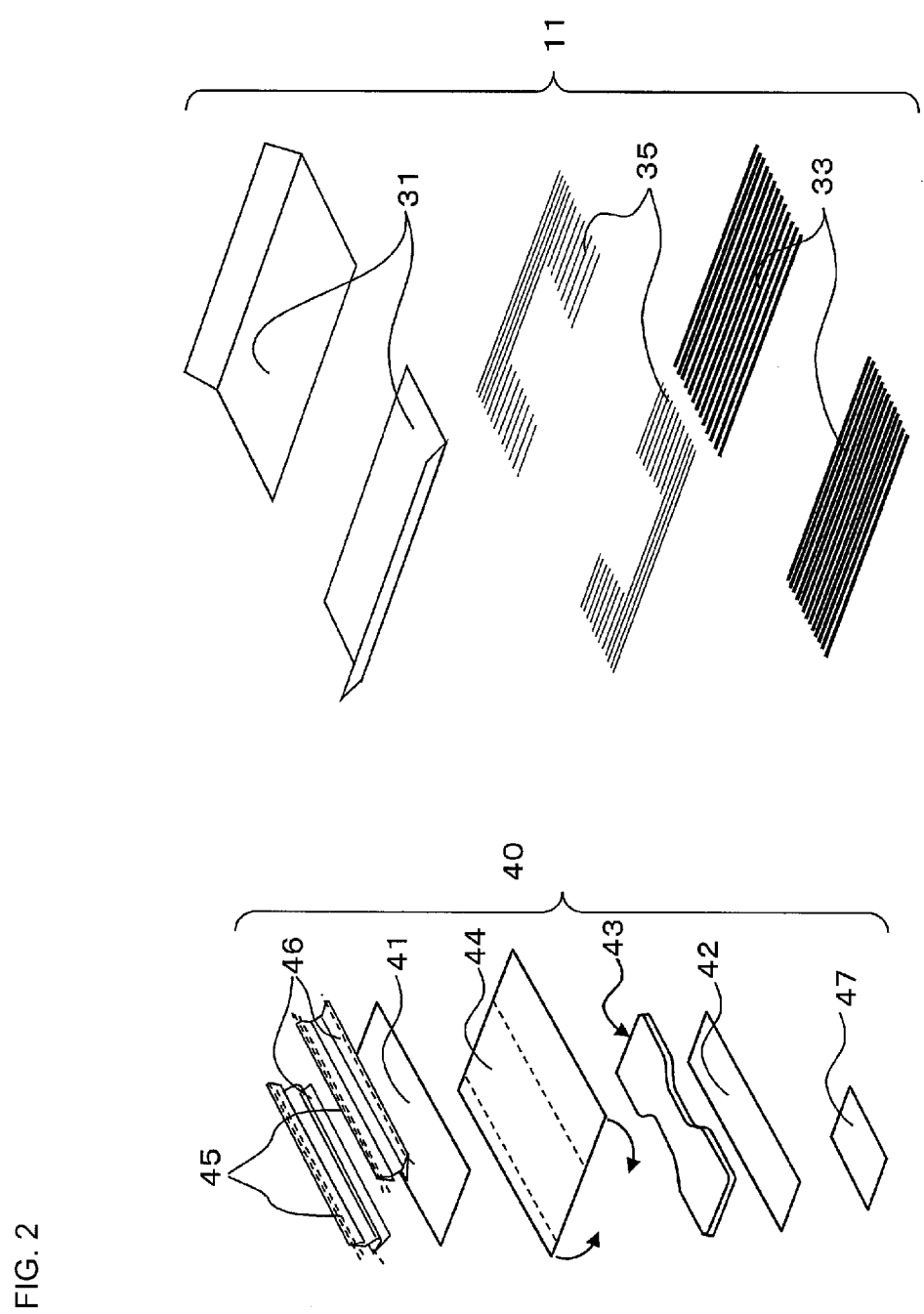
FIG. 2 is an exploded perspective view showing a preferable embodiment of the pull-on wear article of the present invention.

As shown in FIG. 1 and FIG. 2, the pull-on wear article 10 of the present embodiment is, for example, a pull-on diaper, and has a front portion 21 adapted to be worn around the front side of a wearer, a crotch portion 13 adapted to be worn along the wearer's crotch region, and a rear portion 23 adapted to be worn around the wearer's rear side. This pull-on diaper 10 will be explained in detail hereinafter.

The pull-on diaper 10 is constituted by an outer cover 11 formed by the front portion 21 and the rear portion 23, and an absorbent body 40 that forms the crotch portion 13.

The outer cover 11 is constituted into a ringed shape by bonding one lateral side edge 21A of the front portion 21 and one lateral side edge 23A of the rear portion 23, and further bonding the other lateral side edge 21B of the front portion 21 and one lateral side edge 23B of the rear portion 23. Side seal portions 25 are constituted at the bonded portion of the lateral side edges 21A and 23A and the bonded portion of the lateral side edges 21B and 23B, respectively.

Furthermore, the crotch portion 13 is constituted by an absorbent body 40 that bridges between the front portion 21 and the rear portion 23 and thus is adapted to be worn along the wearer's crotch. A pull-on (Pants) shape is constituted by the outer cover 11 formed into a ringed shape and the absorbent body 40 that bridges the crotch portion 13.

The absorbent body 40 that forms the crotch portion also extends to somewhat below a waist opening 12 of the outer cover 11 and is fixed on the outer cover 11 at the front portion 21 and the rear portion 23. By this, in the waist-surrounding area, the outer cover 11 has a central area on which the absorbent body 40 is fixed, and both lateral areas on which the absorbent body 40 is not fixed. The above-mentioned "waist-surrounding area" refers to an area almost from the upper edge of the waist opening 12 to a position downward in the direction of length (Y direction) to near where the outer top of thigh resides.

The above-mentioned outer cover 11 is constituted by laminating an inner layer material 31 and outer layer materials 33, and has plural single layer areas in which a single layer of the inner layer materials 31 is present, at intervals in the direction of length (Y direction) of the outer cover 11. In the drawing, a structure is shown in which the inner layer material 31 is present in the single layer areas and the outer layer materials 33 are laminated on the inner layer material 31 at intervals in the direction of length of the outer cover 11.

The laminate area where the inner layer material 31 and the outer layer materials 33 are laminated has elasticity in the lateral direction (X direction) of the pull-on diaper 10. The laminate area may have an elastic member 35 between the inner layer material 31 and the outer layer materials 33. In such case, each elastic member 35 is sandwiched in its extended state between the inner layer material 31 and outer layer material 33, and thus has elasticity. Alternatively, as explained below in detail, both or one of the inner layer material 31 and outer layer material 33 may be constituted of an elastic material.

Furthermore, it is preferable that the elastic member 35 be cut at plural portions so that the laminated areas of the inner layer material 31 and outer layer materials 33 do not have substantial elasticity at the central area of the outer cover 11 on which the absorbent body 40 is fixed.

As the sheets materials for the inner layer material 31 and outer layer material 33, for example, nonwoven fabrics obtained by various production methods such as air-through nonwoven fabric, heat-roll nonwoven fabric, spun-lace nonwoven fabric, spunbond nonwoven fabric and melt-blown nonwoven fabric, woven fabrics, knitted fabrics, resin films and the like may be exemplified respectively, and sheet materials formed by integrating these by lamination, and the like can also be used.

Furthermore, specifically the inner layer material 31 is preferably formed of a nonwoven fabric, from the viewpoint of improvement of the air-permeability and texture, and is preferably formed of a water-repellent nonwoven fabric, from the viewpoint of prevention of the leakage of excretory substances.

The elastic members 25 may be any of elastic materials usually used in absorbent articles, such as diapers and sanitary napkins. Examples of such elastic materials include synthetic rubbers, such as styrene-butadiene, butadiene, isoprene, and neoprene, natural rubber, EVA, elastic polyolefins, and polyurethane, and the like. Forms of the elastic members preferably include a thread or a string (a plat rubber) with a rectangular, square, circular or polygonal section, or multifilamentous yarn.

Next, the absorbent body 40 will be explained. As shown in FIG. 2, as an example, the absorbent body 40 comprises a topsheet 41, a backsheet 42, and a liquid retainable absorbent core 43 that is interposed therebetween. This absorbent core 43 is covered by a cover sheet 44, which is folded at the positions of the dotted lines shown in the drawing in the arrow directions. Furthermore, a pair of side sheets 46 and 46 that form inner three-dimensional gathers 45 are disposed on the skin-contact surface side. The above-mentioned backsheet 42 and an inseam sheet 47 are disposed in this order on the non-skin-contact surface side.

A material that is generally used for this kind of diaper can be used for this absorbent body 40, and the material is not specifically limited.

It is preferable that the topsheet 41 is formed by a hydrophilic nonwoven fabric. As the hydrophilic nonwoven fabric, nonwoven fabrics called as an air-through nonwoven fabric, a point-bond nonwoven fabric, a spunbond nonwoven fabric, a spun-lace nonwoven fabric and a three-dimensional nonwoven fabric, wherein the fibers thereof are polypropylene monofilaments, conjugate fibers of polypropylene and polyethylene, conjugate fibers of polyethylene telephthalate and polyethylene, and the like, which have undergone a hydrophilization treatment, can be preferably used. Furthermore, a sheet obtained by forming open pores on a resin film can also be used as the topsheet 41.

The backsheet 42 is not specifically limited as long as it has waterproof property and moisture permeability. For example, a porous film obtained by melt-compounding a hydrophobic thermoplastic resin, and a fine inorganic filler comprising calcium carbonate and the like or an organic polymer having no compatibility, and the like to form a film, and subjecting the film to monoaxial or biaxial stretching can be exemplified. Examples of the thermoplastic resin may include polyolefins. Examples of the polyolefins may include high- to low-density polyethylenes, linear low density polyethylenes, polypropylene, polybutene and the like, and these can be used alone or by mixing.

For the absorbent core 43, for example, those using a fiber aggregate or the fiber aggregate and an absorbent polymer in combination, and the like can be used. As the fibers that constitute the aggregate, hydrophilic natural fibers such as pulp fibers and synthetic fibers (preferably fibers undergone a hydrophilization treatment), and the like can be used. Although the basis weight is not specifically limited, it is preferably 150 g/m$^2$ to 500 g/m$^2$. Furthermore, for the cover sheet 44, thin paper (tissue paper) such as hydrophilic tissue paper, nonwoven fabrics formed of hydrophilic fibers such as cotton and rayon, nonwoven fabrics formed by subjecting synthetic resin fibers to a hydrophilization treat (composite nonwoven fabrics such as spunbond-meltblown-spunbond (SMS), spunbond-meltblown-meltblown-spunbond (SMMS) and spunbond-spunbond-meltblown-spunbond (SSMS)), and the like can be used.

It is preferable to use a water-repellent nonwoven fabric for the side sheet 46, and spunbond nonwoven fabric, spunbond-meltblown (SM) nonwoven fabric, SMS nonwoven fabric and the like are specifically used. Various nonwoven fabrics can be used for the inseam sheet 47 so as to give fabric-like appearance.

The pull-on diaper 10 of this embodiment has plural single layer areas in each of which a single layer of the inner layer material 31 is present without the outer layer material 33, at intervals in the direction of length of the outer cover 11; therefore, the air-permeability can be markedly enhanced at the portions of the single layer areas, while maintaining same elasticity to that of a conventional pull-on diaper and retaining the fittability to the body and the movability of the body. Therefore, the steaminess can be significantly reduced. Furthermore, since the use amount of the outer layer materials 33 used can be decreased, a so-called environment-friendly product is provided, and the production cost can be reduced. In addition, the softness of the outer cover 11 is improved, and the motion during wearing becomes smooth and the wearability is improved, by the presence of the single layer areas.

Next, examples of the disposition constitutions of the outer layer materials 33, inner layer material 31 and elastic members 35 for the above-mentioned preferable embodiment will be explained. First, the first example of the pull-on diaper 10 of the first embodiment will be explained, and for the other examples and the second embodiment mentioned below, different points will be explained. The points that are not specifically explained are the same as those in the first embodiment and the first example, and the described explanations are suitably applied. Furthermore, same symbols are provided to similar materials and parts.

Figure 3:
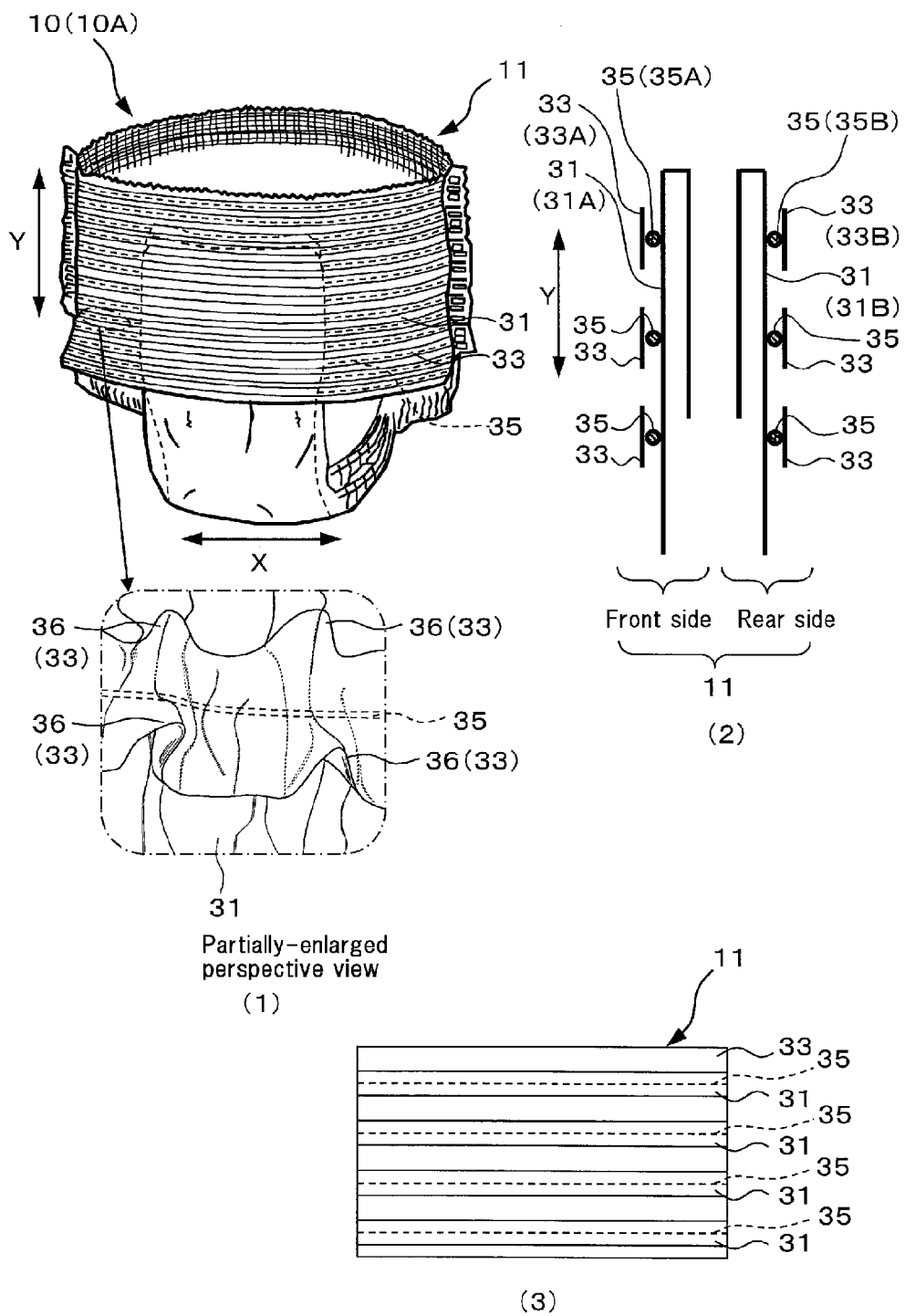
FIG. 3 shows (1) a perspective view and a partially-enlarged perspective view, (2) an enlarged cross-sectional view of the main portion, and (3) an enlarged plane view of the main portion, which show the first example of the pull-on wear article.

The first example of the pull-on diaper 10 will be explained by FIG. 3. As shown in FIG. 3, the pull-on diaper 10 (10A) of the first example has a structure in which the outer layer materials 33 are attached to the inner layer material 31 through elastic members 35 by an adhesive such as a hot-melt adhesive (not shown) at predetermined intervals in the direction of length (Y direction) of the pull-on diaper 10 in the above-mentioned pull-on diaper 10 of the first embodiment. The elastic members 35 are fixed to the outer layer materials 33 and inner layer material 31 in their extended state. Although the pull-on diaper 10 has the outer layer materials 33 of the same number as the number of the attached elastic members 35, plural pieces of the elastic members 35 may be disposed on one outer layer material 33. Meanwhile, the enlarged cross-sectional view of the main portion of FIG. 3 (2) shows the state in which the inner layer material 31 is folded back to the skin contact surface side so as to cover a portion (not shown) to which the absorbent body 40 is attached.

In the central area of the outer cover 11 on which the absorbent body 40 is fixed, the elastic members 35 are cut over at plural points, and thus the laminate areas of the inner layer material 31 and the outer layer materials 33 therein do not have substantial elasticity.

The width of the outer layer material 33 and the intervals for attaching the outer layer materials 33 are suitably decided. For example, a width of the outer layer material 33 is preferably approximately similar to or more than the width of the elastic member 35. For example, it is preferable to adjust the width of the outer layer material 33 to 0.5 mm to 60 mm, and it is preferable to adjust the attachment intervals of the outer layer materials 33 to 1 mm to 40 mm. Further preferably, the width of the outer layer material 33 is adjusted to 5 mm to 10 mm, and the attachment intervals of the outer layer materials 33 are adjusted to 5 mm to 10 mm. When the width and attachment intervals of the outer layer material 33 are adjusted as mentioned above, the wearing comfort of the pull-on diaper 10 is further improved. Furthermore, by adjusting the attachment intervals to equal intervals, an action that a stress applied to the body by the contraction of the elastic members is evenly dispersed can be obtained, and an effect that the impression on the appearance (aesthetic impression provided by regularity) is improved can also be obtained.

Since the lateral direction end portions (the end portions in the direction of length of the diaper) of the outer layer materials 33 are free ends, when the load for stretching of the elastic members 35 is released, the outer layer materials 33 contract due to the contraction of the elastic members to form frills 36 (see the enlarged perspective view). Therefore, there is an action that cuteness can be created as the entirety of the diaper. Furthermore, the position of the attachment of the outer layer material 33 to the inner layer material 31 is not limited to the central portion of the outer layer material 33 in the lateral direction (Y direction), and may be deviated to either of the lateral direction. Namely, in the lateral direction of the outer layer material 33, the distance from the position of the attachment to the inner layer material 31 to one edge may be long and the distance to the other edge may be short. By changing the distances from the position of the attachment to the edges in this way, the frills are easily formed at the longer distance.

Furthermore, the side seal portions 25 are portions where the lateral side edges of the front portion 21 of the outer cover 11 and the lateral side edges of the rear portion 23 of the outer cover 11 are respectively bonded by sealing such as embossing. For example, the inner layer material 31 (31A) of the front portion 21 and the inner layer material 31 (31B) of the rear portion 23 are bonded together in the state that the outer layer material 33 (33A) of the front portion 21 and the outer layer material 33 (33B) of the front portion 21 face each other. Therefore, in the side seal portion 25, the elastic member 35 (35A) disposed on the front portion 21 and the elastic member 35 (35B) disposed on the rear portion 23 are disposed in a state that they are facing each other through the inner layer material 31.

This structure can also be applied to an example using the elastic members 35 explained below, and to the second embodiment. Furthermore, this structure can also be applied to an example in which the elastic members 35 are not used mentioned below, except for the elastic members 35.

In the above-mentioned side seal portion 25, the portion where the inner layer material 31 and outer layer material 33 are laminated becomes a portion where bonding strength is strong, and the portion having only the inner layer material 31 becomes a portion where bonding strength is weak. Therefore, the bonded portion is easily peeled off at the area having only the inner layer material. Furthermore, since the side seal portion 25 has the areas having only the inner layer material 31, the flexibility of the side seal portion 25 is enhanced, the wearing comfort is improved, and the touch to the skin and texture on the skin-contact surface side are further improved.

As the materials for the inner layer material 31 and outer layer materials 33, the sheets explained in the above-mentioned first embodiment can be used. The elastic members 25 may be any of elastic materials of usually used in absorbent articles, such as diapers and sanitary napkins. Examples of such elastic materials include synthetic rubbers, such as styrene-butadiene, butadiene, isoprene, and neoprene, natural rubber, EVA, elastic polyolefins, and polyurethane. Forms of the elastic members preferably include a thread or a string (a plat rubber) with a rectangular, square, circular or polygonal section, or multifilamentous yarn.

In the first example of the pull-on diaper 10A, the effects mentioned for the pull-on diaper 10 in the first embodiment can be obtained. Furthermore, elasticity is imparted to the outer cover 11 at the laminate areas of the outer layer materials 33 and inner layer material 31 where the elastic members 35 are disposed. This elasticity improves the fittability of the pull-on diaper to the body. As shown in the enlarged perspective view in FIG. 3(1), Since the lateral direction end portions (the end portions in the direction of length of the diaper) of the outer layer materials 33 are free ends, when the load for stretching of the elastic members 35 is released, the outer layer materials 33 contract due to the contraction of the elastic members to form frills 36. Therefore, there is an action that cuteness can be created as the entirety of the diaper. In addition, since the elastic members 35 are covered with the outer layer materials 33, the elastic members 35 are protected by the outer layer materials 33. By this, direct application of outer force to the outer layer materials 33 is prevented, and thus the elastic members 35 become difficult to be cut.

Figure 4:
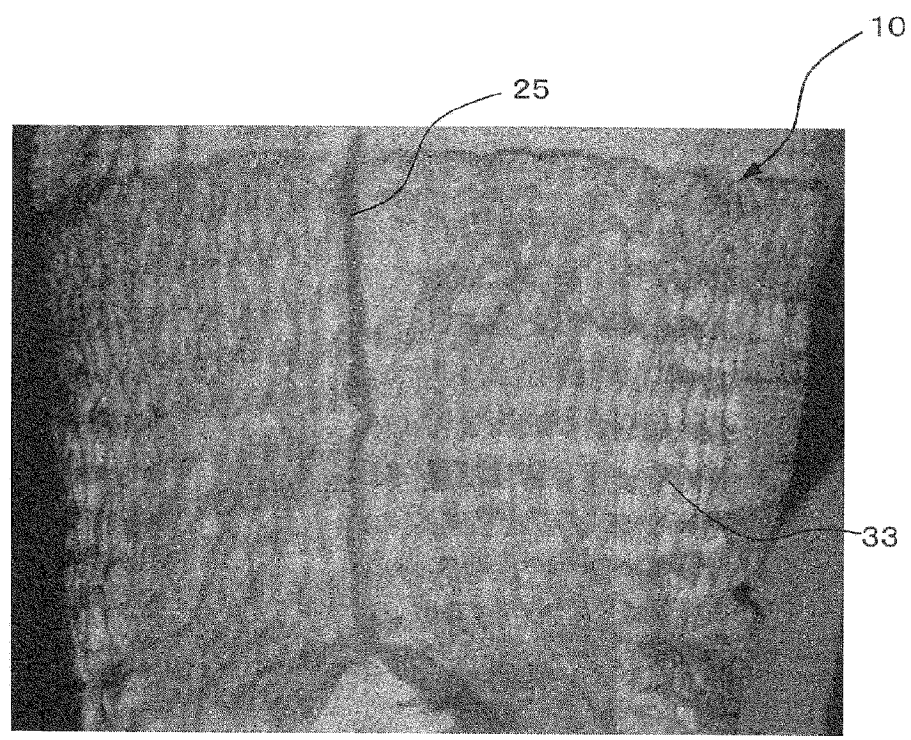
FIG. 4 shows a photograph taken from the side surface of the pull-on wear article in the state that the pull-on wear article of the first example is worn by a dummy doll.

Furthermore, as shown in FIG. 4, colored or printed sheets may be used for the outer layer materials 33. By using such sheets (the band-like sheets that are thickly photographed in the lateral direction in the photograph), the laminate areas are easily distinguished, and it becomes possible to provide the pull-on diaper 10 that is excellent in design.

Although the first example shown in FIG. 3 shows a structure in which the outer layer materials 33 are attached to the inner layer material 31 through the elastic members 35 at predetermined intervals, for example, conversely, a structure in which the slitted inner layer materials 31 are attached to the outer layer material 33 through the elastic members 35 at predetermined intervals by a hot-melt adhesive may also be used.

Figure 5:
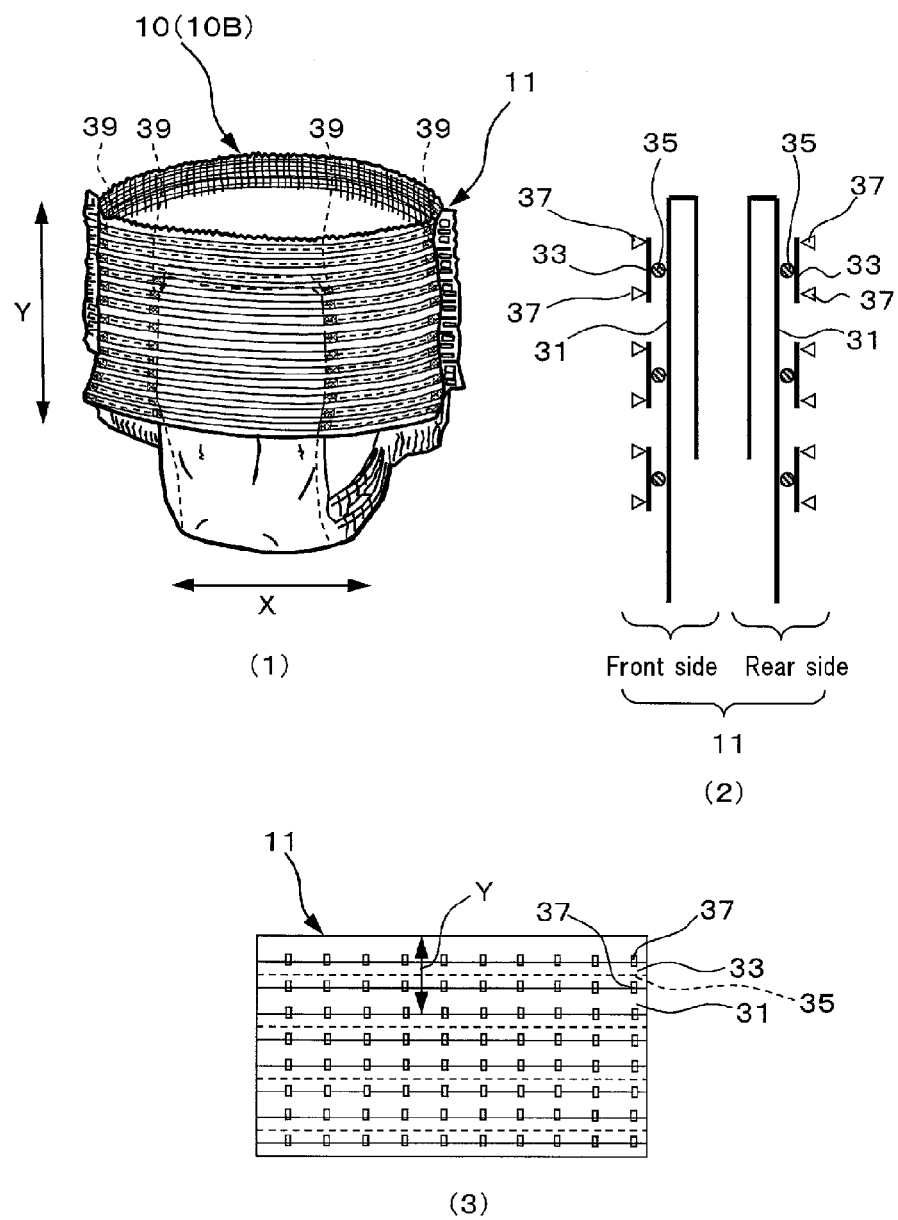
FIG. 5 shows (1) a perspective view, (2) an enlarged cross-sectional view of the main portion, and (3) an enlarged plane view of the main portion, which show the second example of the pull-on wear article.

Next, the second example of the pull-on diaper 10 will be explained by FIG. 5. As shown in FIG. 5, the pull-on diaper 10 (10B) of the second example has a structure in which the outer layer materials 33 are fixed on the inner layer material 31 through the elastic members 35 at predetermined intervals by seal portions 37 in the pull-on diaper 10 of the above-mentioned first embodiment. The width of the outer layer material 33 and the interval between the outer layer materials 33 are in accordance with the first example. In this structure, the respective elastic members 35 are in an extended state and the both ends thereof are fixed by bonding with an adhesive 39 to thereby impart elasticity to the entirety of the outer cover 11. Each elastic member 35 is not fixed to the outer layer material 33 and inner layer material 31 at the portions other than the both ends thereof. Therefore, fine elasticity can be obtained at the laminate areas of the outer layer materials 33 and inner layer material 31 without inhibiting the elasticity of the elastic members 35. At the central area of the outer cover 11 on which the absorbent body 40 is fixed, the laminate areas of the outer layer materials 33 and inner layer material 31 have elasticity.

Furthermore, in this structure, gathers can be made by disposing seal portions 37 with regularity on the portions where the inner layer material 31 and outer layer materials 33 form two layers with the elastic members 35 interposed therebetween. In this second example, the air-permeability is improved since gaps that allow ventilation toward the direction of length (Y direction) in the portions between the outer layer materials 33 and inner layer material 31 are made by the gathers. Furthermore, the gathers impart impression in design to products.

In the pull-on diaper 10 (10B) of the second example, similar effects to those in the pull-on diaper 10 of the above-mentioned first embodiment can be obtained. Furthermore, since the outer layer materials 33 are attached to the inner layer material 31 by forming the seal portions 37 at intervals on the lateral side portions in the waist-surrounding direction of the outer layer materials 33, air-permeability can also be obtained in the lateral direction (Y direction shown by an arrow in the drawing) of the outer layer materials 33 between the outer layer materials 33 and inner layer material 31. Therefore, air-permeability can also be ensured at the portions of the inner layer materials 31 with the outer layer materials 33, in addition to the air permeability at the portions of the inner layer material 31 without the outer layer materials 33. Accordingly, the pull-on diaper 10 (10B) that does not lose its softness, is excellent in elasticity, has fine air-permeability and is very difficult to become steamy can be provided, despite that the outer cover 11 has the laminate areas.

Figure 6:
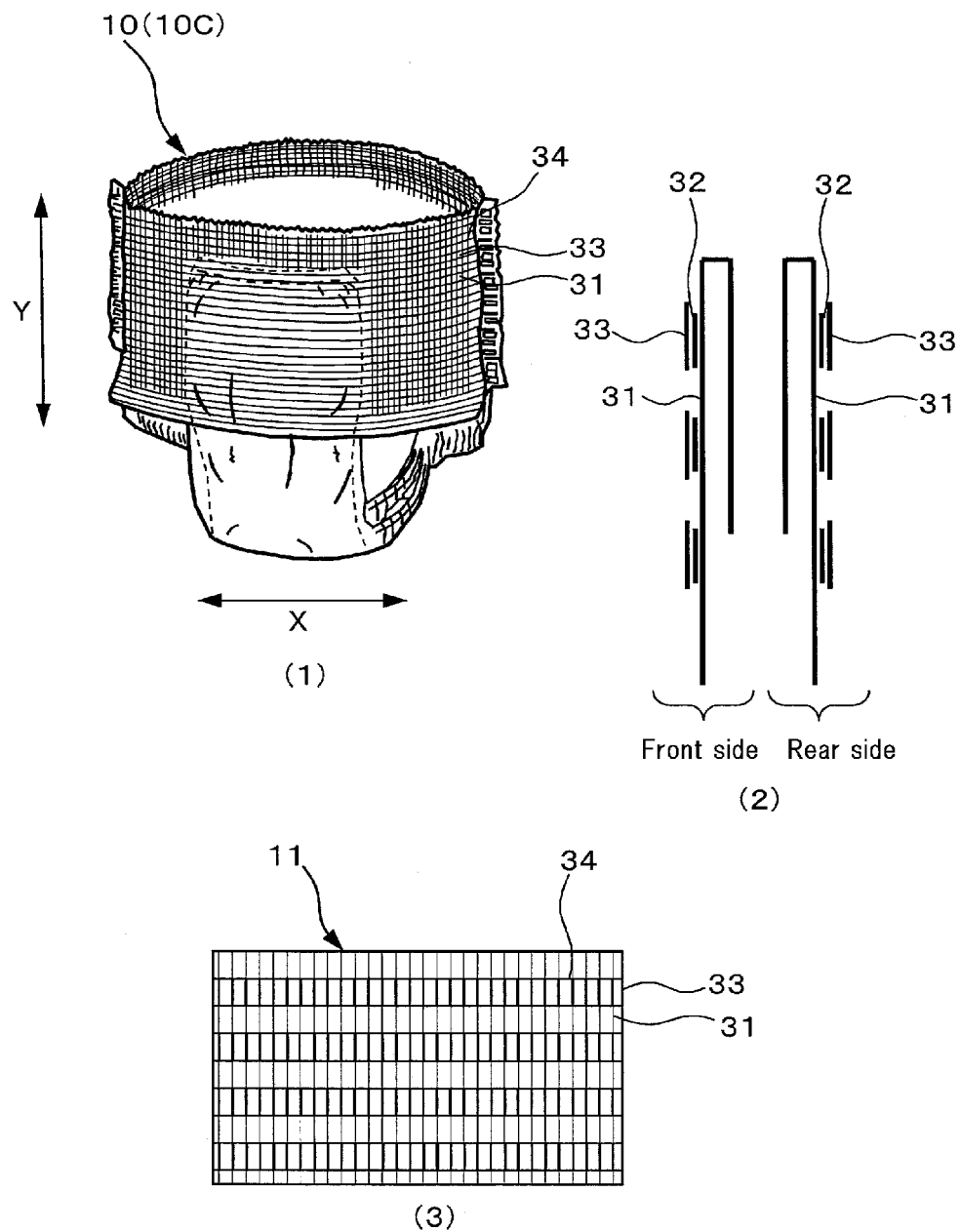
FIG. 6 shows (1) a perspective view, (2) an enlarged cross-sectional view of the main portion, and (3) an enlarged plane view of the main portion, which show the third example of the pull-on wear article.

The third example of the pull-on diaper 10 will be explained by FIG. 6. As shown in FIG. 6, the pull-on diaper 10 of the third example (10C) has a structure in which the outer layer materials 33 themselves have elasticity in the longitudinal direction (waist-surrounding direction), and these outer layer materials 33 are attached to the inner layer material 31 in an extended state by an adhesive 32, in the pull-on diaper 10 of the above-mentioned first embodiment. As the adhesive, for example, a hot-melt adhesive, a double-faced adhesive tape and the like are used.

The elasticity that the outer layer materials 33 themselves have, as used herein, refers to, for example, elasticity that can substitute for the elasticity that is imparted by the above-mentioned elastic members.

As the outer layer materials 33 having elasticity, elastic sheets such as nonwoven fabrics comprising elastic fibers and elastic films can be used. In the case where texture and fabric-like appearance are emphasized, it is preferable that these elastic sheets have a fiber layer on the surface. In the case where this fiber layer is inelastic, the fiber layer is made possible to stretch by a stretching processing or the like so that the inelastic fiber layer will not inhibit the elasticity of the elastic sheet. As the stretching processing, for example, a tooth-groove processing of cutting joins between the fibers or elongating the fibers, partially in the fiber layer is exemplified, and by this, elasticity is expressed without inhibiting the elasticity of the elastic sheet. By the tooth-groove processing, on the surface of the fiber layer, as shown in the enlarged plane view of the main portion of FIG. 6 (3), concave and convex (the concave is grooves 34) are formed on the surfaces of the outer layer materials 33.

The intervals of the above-mentioned grooves 34 are adjusted to, for example, equal intervals. In addition, in the case where the degree of imparting of elasticity is changed in every position, it is also possible to change the intervals of the grooves 34. For example, in the case where the thickness of the outer layer materials 33 is 0.01 mm to 0.2 mm, at an area where strong elasticity is desired, the intervals of the grooves 34 are adjusted to about 2 mm to 5 mm, and at an area where weak elasticity is desired, the intervals of the grooves 34 are adjusted to about 0.5 mm to 2 mm. The intervals of the grooves 34 are also changed depending on the thickness of the outer layer materials 33. The method for processing the outer layer materials 33 is not limited as long as the outer layer materials have desired elasticity by the grooves 34.

In addition, the width of the outer layer material 33, and the intervals of the outer layer materials 33 are in accordance with the first example.

In addition, a tooth-groove processing as a stretching processing is also conducted on the outer layer materials 33 on the absorbent body 40. After the stretching processing, the outer layer materials 33 are elongated and bonded to the inner layer material 31. After the bonding, the outer layer materials 33 and the inner layer material 31 are heat-sealed (the elastic members are cut) at the corresponding portions on the absorbent body 40, so that the outer layer materials 33 are made inelastic and lose their elasticity at the corresponding portions, and then the tooth-grooves formed on the outer layer materials 33 on the absorbent body 40 become less prominent.

As the above-mentioned outer layer materials having elasticity, for example, (1) a sheet comprising an elastic fiber layer and an extensible fiber layer(s) that is/are integrated with one or both surface(s) of the elastic fiber layer, (2) a sheet comprising a net-like elastic sheet and an extensible fiber layer(s) that is/are integrated with one or both surface(s) of the elastic sheet, (3) a sheet comprising an elastic sheet formed of an elastic film and an extensible fiber layer(s) that is/are integrated with one or both surface(s) of the elastic sheet, (4) an elastic sheet in which many elastic filaments disposed to be extensible in one direction without intersecting with each other are bonded to an extensible nonwoven fabric, substantially an inextensible state, over the full lengths thereof.

As the sheet of the above-mentioned (1), for example, (a) an elastic nonwoven fabric in which a substantially inelastic fiber layer is disposed on at least one surface of an elastic fiber layer, wherein the both fiber layers are bonded on the whole surface by heat-fusion bonding of the intersection points of the fibers in the state that the constitutional fibers in the elastic fiber layer retain the shapes of the fibers, and the nonwoven fabric is in either of the state in which a part of the constitutional fibers in the inelastic fiber layer has penetrated into the elastic fiber layer, and the state in which a part of the constitutional fibers in the elastic fiber layer has penetrated into the inelastic fiber layer, or in both states, can be exemplified. Furthermore, as the sheets of the above-mentioned (1) to (3), (b) an elastic sheet having an elastic layer with elastic stretchability and a substantially inelastic fiber layer, wherein the two layers are made into a laminated sheet by laminating in their thickness direction and bonding partially and a stretching is performed to the laminated sheet, and the like can be preferably used. As a means for these stretchings and for obtaining the extensible fiber layers and nonwoven fabrics of the above-mentioned (1) to (3), it is preferable to conduct the above-mentioned tooth-groove processing.

As the elastic nonwoven fabric of the above-mentioned (a), in the interface of the elastic fiber layer and non-elastic fiber layer and in the vicinity thereof, the intersection points of the constitutional fibers of the elastic fiber layer and the constitutional fibers of the non-elastic fiber layer are bonded by heat-fusion, and thus are evenly bonded on substantially the whole surface. Since the two layers are bonded on the whole surface, formation of spaces by the separation of the two layers is prevented, and an elastic nonwoven fabric having a multilayer structure that gives feeling of unity like a nonwoven fabric of a single layer is formed. The above-mentioned state that the constitutional fibers of the elastic fiber layer retains the fiber forms refers to a state that most of the constitutional fibers in the elastic fiber layer are not deformed into a film shape, or a film structure comprising fibers, even in the case where heat, pressure or the like is applied. Furthermore, in the elastic fiber layer, the intersection points of the constitutional fibers are bonded by heat-fusion in the layer. Similarly, also in the non-elastic fiber layer, the intersection points of the constitutional fibers are heat-fusion bonded in the layer.

In the case where the inelastic fiber layers are disposed on the both surfaces of the elastic fiber layer, at least either one surface is in the state in which a part of the constitutional fibers thereof has penetrated into the elastic fiber layer, or the state in which a part of the constitutional fibers in the elastic fiber layer has penetrated into at least one of the inelastic fiber layers, or in both states.

The elastic fiber layer has a property that it can be stretched, and has a property to contract when it is released from load for stretching. Furthermore, it is an aggregate of fibers having elasticity. Moreover, the elastic fiber layer may be in the form of a web or nonwoven fabric formed of fibers having elasticity. For example, it may be a nonwoven fabric formed by a spinning blown process, a spunbond process, a meltblown process or the like. Specifically, a web obtained by a spinning blown process is preferable. As the constitutional fibers for the elastic fiber layer, for example, fibers obtained from raw materials such as thermoplastic elastomers and rubbers can be used. Specifically, fibers obtained from thermoplastic elastomers as raw materials are preferable for the stretchable nonwoven fabric in the embodiment comprising an air-through nonwoven fabric as a basic constitution, since melt spinning using an extruder as same as in general thermoplastic resins is possible, and fibers obtained by such way are easily heat-fusion bonded. Examples of the thermoplastic elastomers may include styrene-based elastomers such as SBS, SIS, SEBS and SEPS, olefin-based elastomers, polyester-based elastomers, and polyurethane-based elastomers. These can be used by one kind alone or by a combination of two or more kinds.

The inelastic fiber layer has extensibility, but is substantially inelastic. The extensibility as used herein may be either of the case where the constitutional fibers themselves elongate, and the case where the constitutional fibers themselves do not elongate, but the entirety of the fiber layer elongates due to a separation of the fibers that are heat-fusion bonded at the intersection points of the fibers, a structure change in the three-dimensional structure formed of plural pieces of fibers by the heat-fusion bonding of the fibers and the like, or a tear of constitutional fibers. Examples of the fibers that constitute the inelastic fiber layer may include fibers formed of polyethylene (PE), polypropylene (PP), polyesters (PET and PBT), polyamides and the like. The fibers that constitute the inelastic fiber layer may be either short fibers or long fibers, and may be either hydrophilic or water-repellent. Furthermore, core-sheath type or side-by-side conjugate fibers, splittable fibers, modified cross-sectional surface fibers, crimped fibers, heat-shrinkable fibers and the like can also be used. These fibers can be used alone by one kind or as a combination of two or more kinds. The non-elastic fiber layer may be a web or nonwoven fabric of continuous filaments or short fibers.

The elastic sheet of the above-mentioned (b) is obtained by conducting a stretching processing on a laminated sheet comprising an elastic layer having elastic stretchability and substantially inelastic fiber layer(s) that is/are laminated on one or both surface(s) of the elastic layer, wherein the inelastic fiber layer(s) is/are partially bonded in a regulated pattern.

The effects of the pull-on diaper 10 (10C) of the third example are as mentioned in the pull-on diaper 10 of the above-mentioned first embodiment. In this example, since the outer layer materials 33 are subjected to a stretching processing so as to have concave and convex, without requiring elastic members that are disposed between the inner layer material 31 and outer layer materials 33, soft appearance and touch are provided, and frills can also be formed on the outer layer materials 33 by narrowing the application width of the adhesive 32 than the width of the outer layer material 33. In addition, the materials for the elastic members can be decreased.

Furthermore, by changing the widths of the outer layer materials 33, the elastic force is also changed and can be adjusted to a suitable constriction pressure corresponding to each site such as waist portion, on portion on ilium and lumbar. For example, by increasing width more on the waist portion and the portion on ilium than those on the other sites, the elastic force can be enhanced and the constriction pressure can be increased.

In the pull-on diaper 10 of the third Example, in the case where the elasticity of the laminated areas is weak, the elastic member 35 of the first Example may be interposed between the outer layer materials 33 and the inner layer material 31 as necessary.

Figure 7:
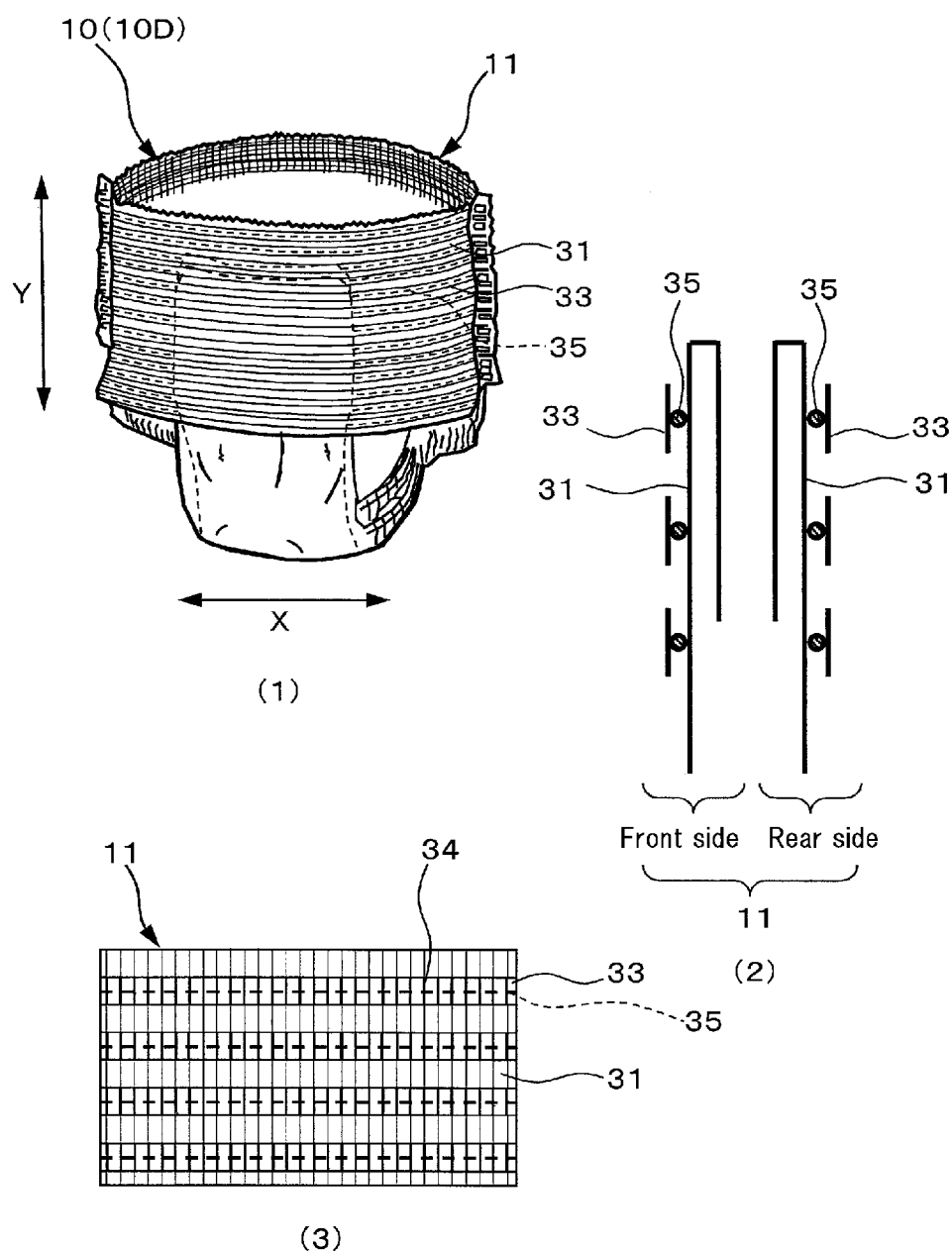
FIG. 7 shows (1) a perspective view, (2) an enlarged cross-sectional view of the main portion, and (3) an enlarged plane view of the main portion, which show the fourth example of the pull-on wear article.

The fourth example of the pull-on diaper 10 will be explained by FIG. 7. In the fourth example of the pull-on diaper 10 (10D), similar materials to those in the pull-on diaper 10A of the above-mentioned first example are used in the pull-on diaper 10 of the above-mentioned first embodiment. In the pull-on diaper 10 of the above-mentioned first example, as shown in FIG. 7, the outer layer materials 33 and the inner layer material 31 fixed by an adhesive such as a hot-melt adhesive (not shown) through the elastic members 35 have undergone a stretching processing (such as a tooth-groove processing) in the waist-surrounding direction (X direction). By this, the outer layer materials 33 and inner layer material 31 have extensibility. The elastic members 35 are fixed on the outer layer materials 33 and inner layer material 31 in their extended state. As mentioned above, the processing method for the stretching processing is not limited as long as it is a method that makes the outer layer materials 33 and inner layer material 31 extensible.

Furthermore, the width of the outer layer material 33, and the intervals between the outer layer materials 33 are in accordance with the above-mentioned first example.

In the fourth example of the pull-on diaper 10 (10D), similar effects to those in the pull-on diaper 10A of the above-mentioned first example can be obtained. Furthermore, by conducting a tooth-groove processing as a stretching processing, the outer layer materials 33 and inner layer material 31 can be made extensible. By this, elasticity is expressed without inhibiting the elasticity of the elastic members 35, and thus the fittability of the pull-on diaper 10D can be enhanced.

Figure 8:
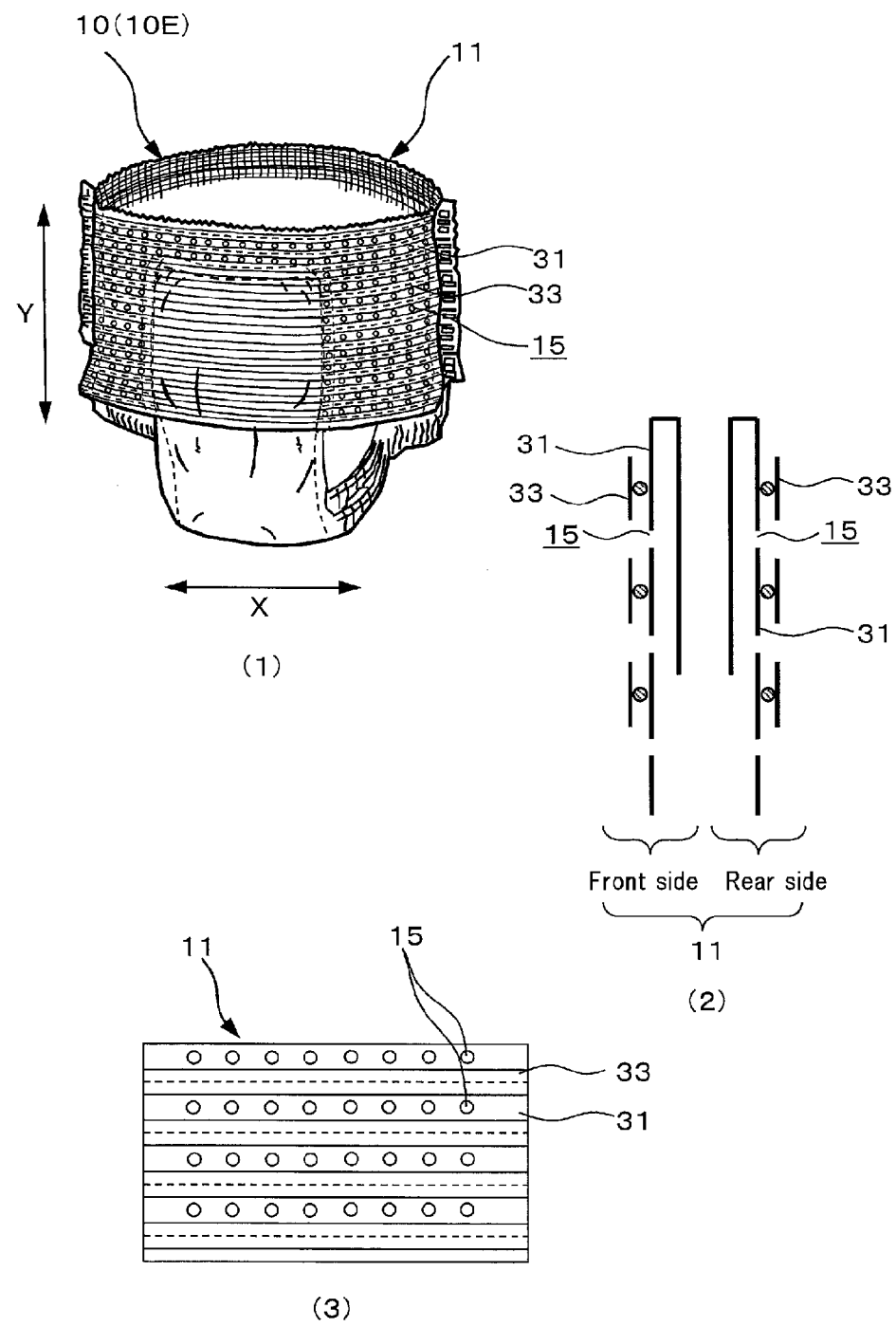
FIG. 8 shows (1) a perspective view, (2) an enlarged cross-sectional view of the main portion, and (3) an enlarged plane view of the main portion, which show the fifth example of the pull-on wear article.

The fifth example of the pull-on diaper 10 will be explained by FIG. 8. As shown in FIG. 8, the pull-on diaper 10 (10E) of the fourth example has a constitution in which pores 15 are formed on an outer cover 11 of the portion of the inner layer material 31 on which the outer layer materials 33 are not disposed in the pull-on diaper 10 of the above-mentioned first embodiment. This constitution can be applied to the pull-on diapers 10 of all of the constitutions that are explained in the description. The pores 15 are formed at predetermined intervals. For example, it is preferable that the pores each has a diameter that is smaller than at least the disposition interval between the outer layer materials 33, depending on the disposal intervals of the outer layer materials 33, and that the interval between pores is adjusted to, for example, 101% or more and 500% or less of the diameter of the pore 15. More preferably, the pore interval is adjusted to 200% or more and 300% or less of the diameter of the pore 15. The pores 15 can be formed by a heated needle, a laser processing or the like.

The pull-on diaper 10 of the fifth example (10E) also exhibits similar effects to those of the pull-on diaper 10 of the above-mentioned first embodiment. In this example, since the pores 15 are formed on the inner layer material 31, the air-permeability is further enhanced.

Next, the second embodiment of the pull-on diaper of the present invention will be explained with referring to FIG. 9.

Figure 9:
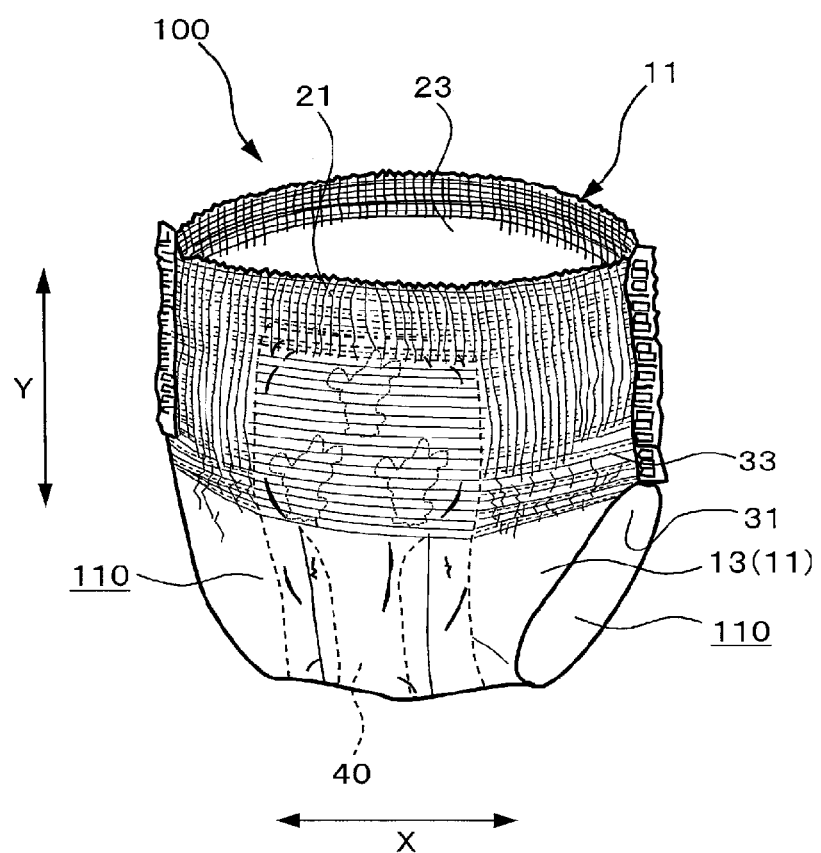
FIG. 9 is a perspective view showing the second embodiment of the pull-on wear article.
Figure 10:
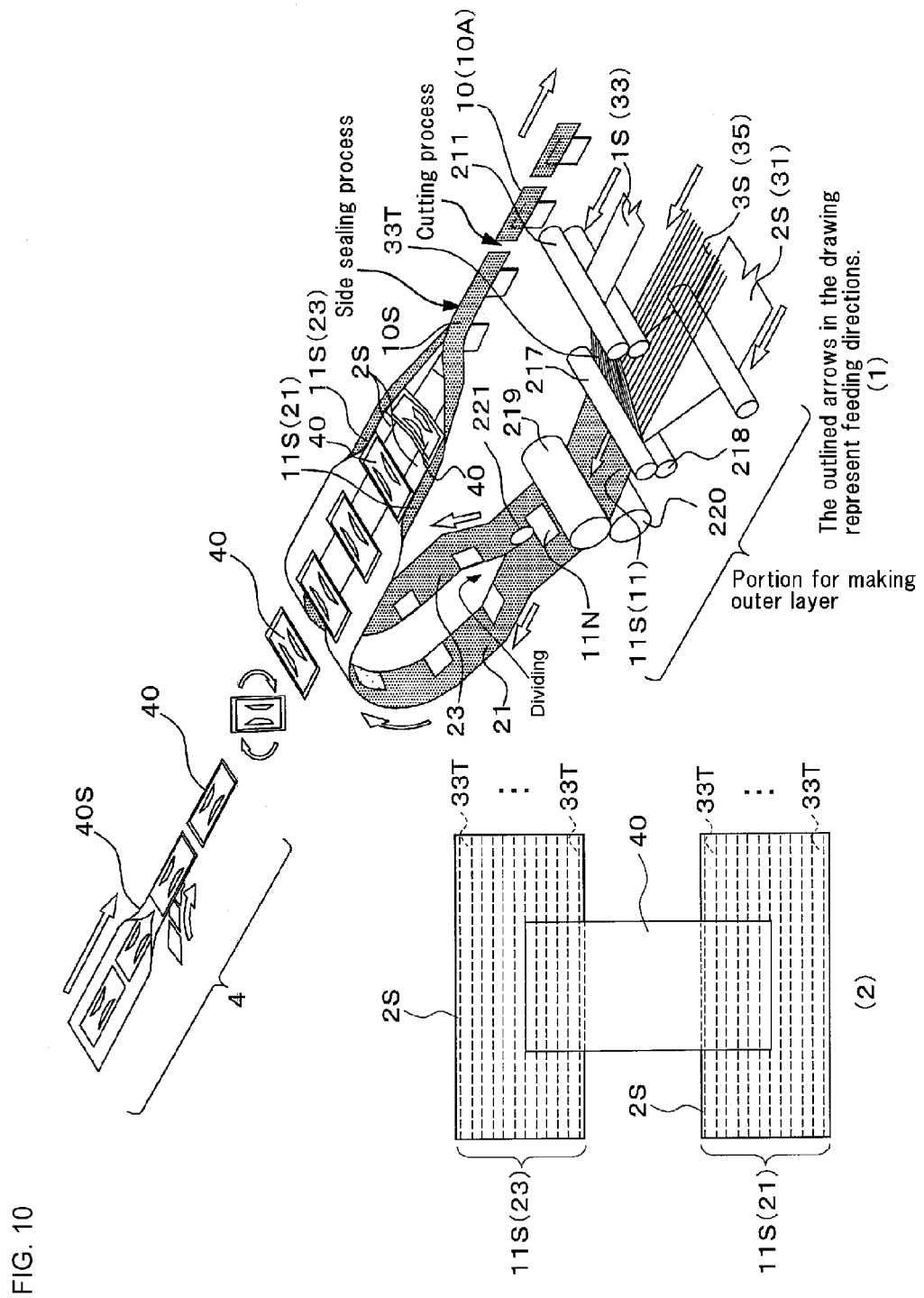
FIG. 10 is a drawing showing the overview of the production steps of the first aspect according to a preferable embodiment (the first embodiment) of the method for producing a pull-on wear article of the present invention, in which (1) is a perspective view showing the entirety of the production steps, and (2) is a top view showing the state in which the absorbent body is laminated.
Figure 11:
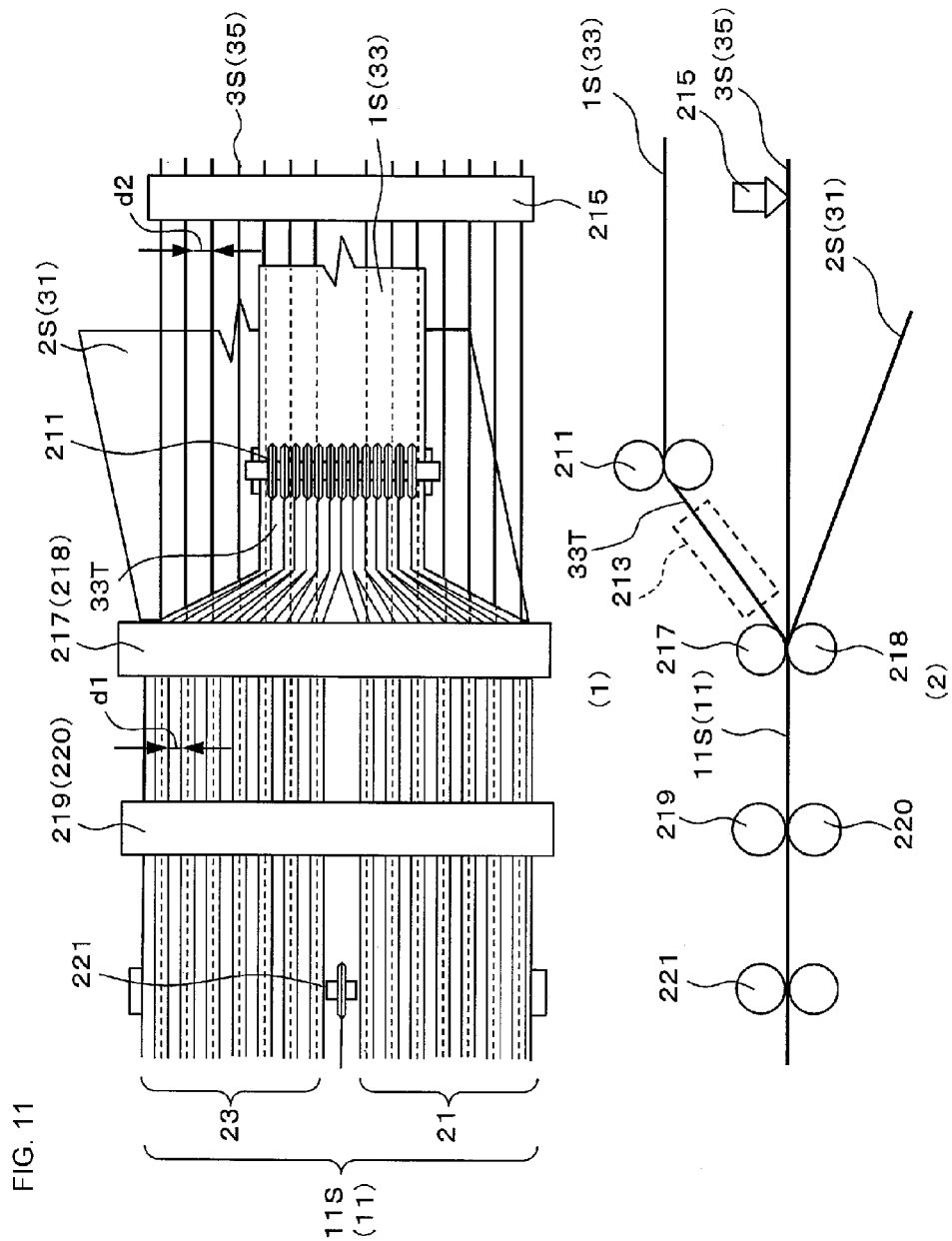
FIG. 11 shows (1) a plane view and (2) a front view, which schematically show the main portion of the first aspect.
Figure 12:
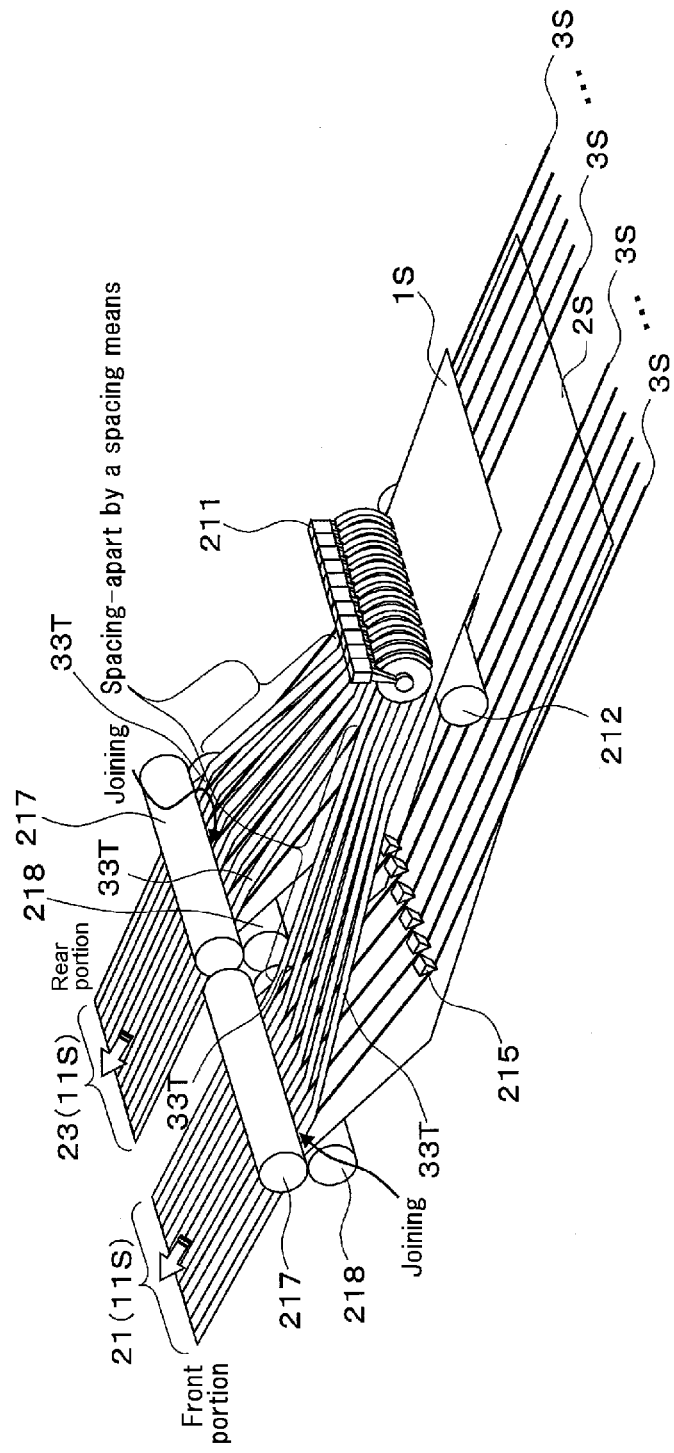
FIG. 12 shows a perspective view of the main portion showing an example of the method for producing the pull-on wear article shown in FIG. 10.
Figure 13:
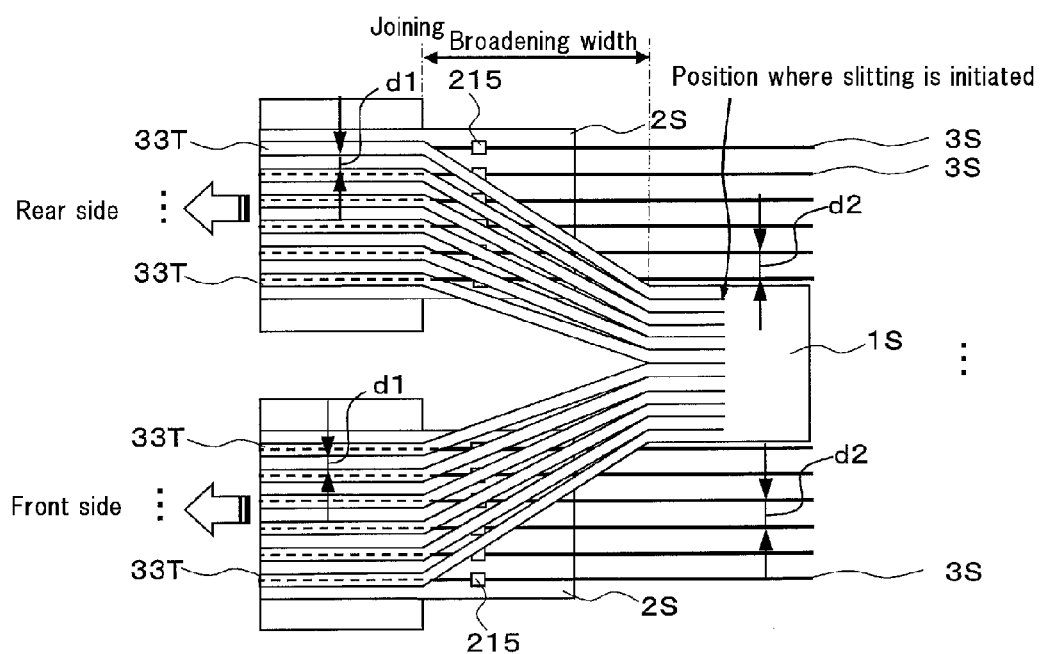
FIG. 13 shows a plane view of the main portion showing an example of the method for producing the pull-on wear article shown in FIG. 10.

As shown in FIG. 9, the pull-on diaper 100 as an example of a pull-on diaper has a constitution in which an outer cover 11 is also formed on a crotch portion 13, and an absorbent body 40 is disposed inside (skin-contact surface side) of the outer cover 11 formed on the crotch portion 13. Specifically, the pull-on diaper 100 has the crotch portion 13 that is formed so as to continuously bridge the front portion 21 and the rear portion 23 as to the outer cover 11 in the above-mentioned first embodiment. The inner layer material 31 is formed on the rear portion 23, front portion 21 and crotch portion 13 of the above-mentioned outer cover 11, and outer layer materials 33 are laminated at intervals on the inner layer material 31 of the rear portion 23 and front portion 21 along the waist-surrounding direction (X direction). Therefore, the outer layer materials 33 are not laminated on the inner layer material 31 in the crotch portion 13.

As mentioned above, the constitution of the outer layer materials 33 according to the present invention can also be applied to the pull-on diaper 100 having the outer cover that is continuously formed from the front side to the rear side through the crotch, and can improve the air-permeability of the pull-on diaper. Furthermore, the materials used for the outer layer materials 33 can be reduced, and thus the production cost can be reduced.

Next, the first aspect of a preferable embodiment (the first embodiment) of the method for producing a pull-on diaper of the present invention will be explained below, referring to FIG. 10 to FIG. 13. The first aspect of the production method is a method for producing the above-mentioned pull-on diaper 10 (10A). For the points that are not specifically explained in the other aspects mentioned below, the explanations that are mentioned in detail with respect to the first aspect are suitably applied.

As shown in FIG. 10 to FIG. 13, for example, a first sheet material 1S is fed from the upper side, a second sheet material 2S is fed from the lower side, and an elastic member continuous element 3S, which becomes elastic members 35, is fed to the gap between the first sheet material 1S and second sheet material 2S. The first sheet material 1S forms outer layer materials 33, and the second sheet material 2S forms an inner layer material 31. For these first sheet material 1S (outer layer materials 33), second sheet material 2S (inner layer material 31) and elastic member continuous element 3S (elastic members 35), similar materials to those respectively mentioned above in the pull-on diaper 10 are used.

At first, the above-mentioned first sheet material 1S is divided into plural pieces in the lateral direction by an outer layer material slit cutter 211 to thereby form narrow tape-type sheet materials 33T. The tape-type sheet materials 33T and 33T are then spaced apart at predetermined intervals d1 by a spacing means 213. The width of the tape-type sheet material 33T (the divided portion of first sheet material 1S) is formed into the width of each outer layer material 33 (33A, 33B) in the above-mentioned pull-on diaper 10A, and the interval by the spacing is also formed into the interval of the outer layer materials 33 in the above-mentioned pull-on diaper 10A.

Although not shown in the drawing, the above-mentioned spacing means comprises a means equipped with guide rolls to the respective tape-type sheet materials, which is configured to widen the intervals to predetermined intervals by the angles and positions of the disposition of the rolls to thereby converge the tape-type sheet materials and the second sheet material 2S, or a means equipped with guides for adjusting sheet flow (an equipment for correcting snaking) to the respective tape-type sheet materials, which is configured to converge the tape-type sheet materials and the second sheet material 2S.

Furthermore, plural pieces of elastic member continuous elements 3S are prepared in parallel, and fed together with the second sheet material 2S in the state that the respective elastic member continuous elements are extended and an adhesive (not shown) fed by an adhesive coating apparatus 215 is applied thereto. The respective elastic member continuous elements 3S are fed at predetermined intervals d2. At this time, it is preferable that they are fed so that the center of the lateral direction of the elastic member continuous element 3S is positioned on the center of the lateral direction of the above-mentioned tape-type sheet material 33T. For example, a hot-melt gun is used as the above-mentioned adhesive coating apparatus 215, and a hot-melt adhesive is used as the adhesive in this case.

By this, the elastic member continuous elements 3S at the predetermined intervals d2 are fed to the gap between nip rolls 217 and 218 in their extended state on the second sheet material 2S. At the same time, each tape-type sheet material 33T is fed onto each elastic member continuous element in such a manner that the elastic member continuous element 3S is positioned on the center of the lateral direction of the tape-type sheet materials 33T.

Furthermore, the second sheet material 2S, elastic member continuous elements 3S and tape-type sheet materials 33T are passed between the nip rolls 217 and 218, and the second sheet material 2S and tape-type sheet materials 33T are adhered through the elastic member continuous elements 3S by the hot-melt adhesive applied to the elastic member continuous elements 3S by the pressure between the rolls to thereby give an outer cover continuous element 11S that is to be an outer cover 11. Meanwhile, by feeding the adhesive onto either one or both of the tape-type sheet materials 33T and second sheet material 2S by the adhesive coating apparatus 215, the elastic member continuous elements are adhered to the material(s).

Next, an elastic member-cutting step for disabling the expression of the elastic function of the elastic member continuous elements 3S on the portion of the second sheet material 2S in which the absorbent body 40 is fixed is conducted. In this elastic member cutting process, for example, a non-functionalized area 11N can be formed on the outer cover continuous element 11S by using a cut roll 219 with a non-functionalized area-forming portion (not shown) that disables the expression of the contraction force of the elastic member continuous elements 3S. The non-functionalized area-forming portion is constituted by many convex portions or cutter blades that are configured to cut the elastic member continuous elements 3S, or many emboss pins that are configured to cure the elastic member continuous elements 3S by heat sealing, or the like.

A roll 220 corresponding to the cut roll 219 is a receiving roll of the cut roll, and the periphery surface thereof is a smooth surface.

Next, the outer cover continuous element 11S are cut at the central portion in the lateral direction thereof using an outer cover slit cutter 221, and spaced at a predetermined interval so that the front portion 21 and rear portion 23 are formed. The size and the like of the pull-on diaper 10 including this predetermined interval are suitably selected depending on the size and intended use.

Next, the absorbent body 40, which is obtained by cutting an absorbent body continuous body 40S fed from an absorbent body-forming portion 4, is disposed on the predetermined positions of the front portion 21 and rear portion 23 of the outer cover continuous element 11S. At this time, the absorbent body 40 is disposed so that the longitudinal direction thereof becomes, for example, at right angles to the front portion 21 and rear portion 23. The absorbent body 40 is fixed onto the outer cover continuous element 11S while maintaining the extended state of the outer cover continuous element 11S. For example, the absorbent body 40 is fixed while maintaining the outer cover continuous element 11S so as to not shrink by the contraction force of the elastic member continuous element 3S. Generally, an elastic element that contracts in the longitudinal direction of the absorbent body 40 is also disposed on the absorbent body 40, and also in such case, the absorbent body 40 is fixed to the outer cover continuous element 11S while maintaining the absorbent body 40 to not contract. At that time, an adhesive is applied in advance to the absorbent body 40 or outer cover continuous element 11S.

Subsequently, the end portions of the lateral direction outer side of the outer cover continuous element 11S are folded back so as to cover the both end portions in the longitudinal direction of the absorbent body 40, and the absorbent body 40 is fixed on the folded-back portions. In so doing, an adhesive is applied in advance to the predetermined positions of the inner sides of the folded-back portions, the absorbent body 40 and the like.

Next, the longitudinal direction of the absorbent body 40 is folded in two, and the front portion 21 of the outer cover continuous element 11S and the rear portion 23 of the outer cover continuous element 11S are superposed while orienting the second sheet materials 2S to face inward. Subsequently, a side seal step for bonding the front portion 21 and rear portion 23 in the lateral direction thereof at a predetermined interval is conducted. The predetermined interval in this side seal step determines the length in the lateral direction of the pull-on diaper 10. By this, a pull-on diaper continuous body 10S is obtained.

Subsequently, the pull-on diaper continuous body 10S is cut in the lateral direction at the bonded portions obtained by the side sealing. As a result, a pull-on diaper 10 (10A) is completed, and thus the constitution as explained in the first example of the above-mentioned pull-on diaper can be obtained.

In the above-mentioned first aspect of the production method, a single layer regions formed of the inner layer material 31 is formed by laminating the plural pieces of tape-type sheet materials 33T, which are formed by slitting the first sheet material 1S, with the second sheet material 2S in the state that the respective tape-type sheet materials 33T are spaced apart. By this, the air-permeability is markedly increased at the single layer area, and thus the pull-on diaper 10 (10A) in which the steaminess is significantly reduced can be provided.

Furthermore, since the use amount of the outer layer materials 33 can be decreased, a so-called environment-friendly product can be produced in a disposable-type pull-on diaper. In addition, since the use amount of the outer layer materials 33 can be decreased, the production cost can be reduced.

Next, the second aspect of the production method of the present invention will be explained below, referring to the plane view (1) and the front view (2) showing the main portion of FIG. 14. The second aspect is a method for producing the above-mentioned pull-on diaper 10 (10B).

Figure 14:
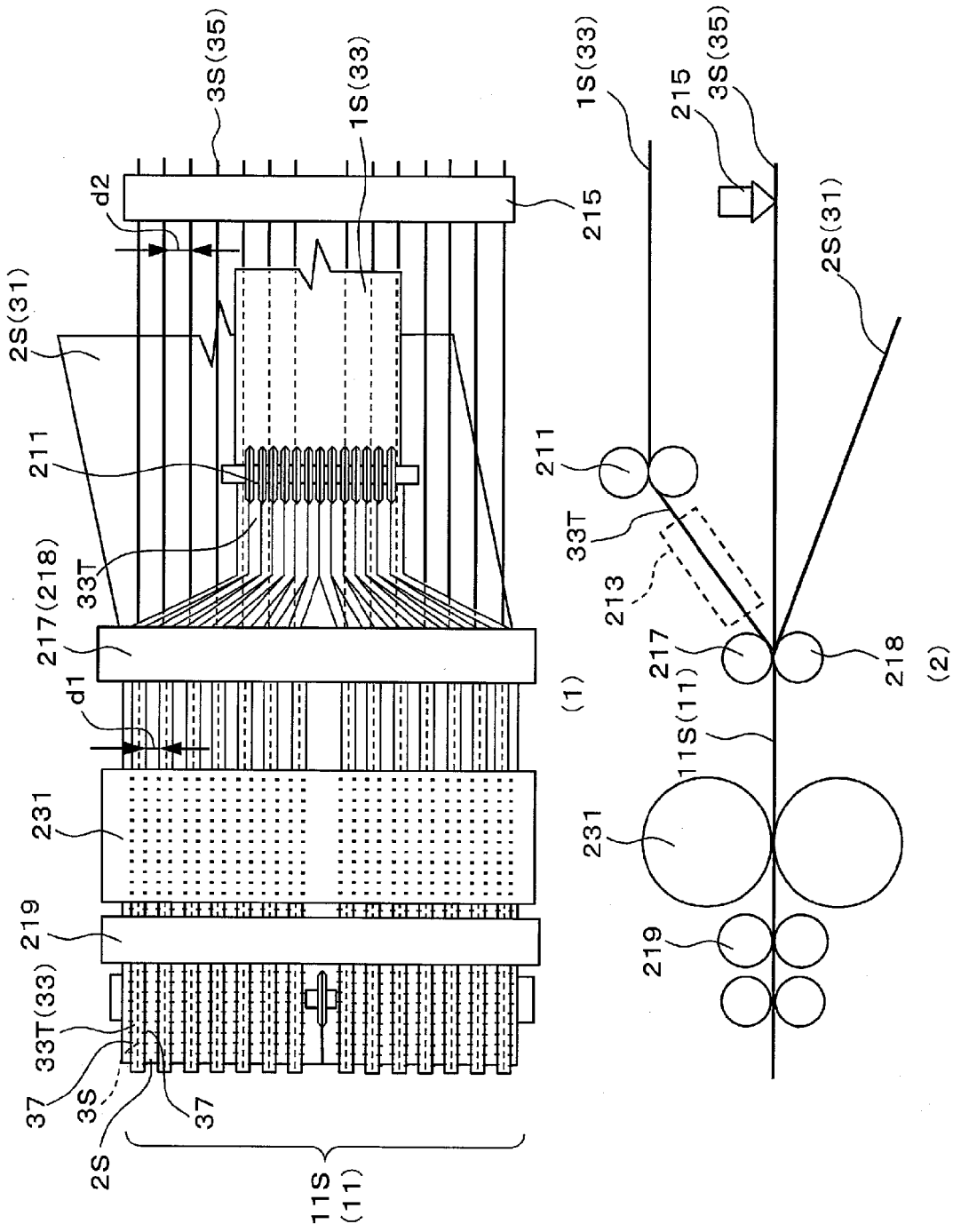
FIG. 14 shows (1) a plane view and (2) a front view, which schematically show the main portions of the production steps of the second aspect according to the method for producing a pull-on wear article of the present invention.

As shown in FIG. 14, for example, a first sheet material 1S is fed from the upper side, a second sheet material 2S is fed from the lower side, and an elastic member continuous element 3S, which becomes elastic members 35, is fed to the gap between the first sheet material 1S and second sheet material 2S. The first sheet material 1S forms outer layer materials 33, and the second sheet material 2S forms an inner layer material 31. For these first sheet material 1S (outer layer materials 33), second sheet material 2S (inner layer material 31) and elastic member continuous element 3S (elastic members 35), similar materials to those respectively mentioned above in the pull-on diaper 10 are used.

At first, the above-mentioned first sheet material 1S is divided into plural pieces in the lateral direction by an outer layer material slit cutter 211 to form narrow tape-type sheet materials 33T, and the tape-type sheet materials 33T and 33T are spaced apart at predetermined intervals d1 by a spacing means 213 that is similar to that explained in the above-mentioned first aspect. The width of the tape-type sheet material 33T (the divided first sheet material 1S) is similar to the width of the outer layer material 33 of the above-mentioned pull-on diaper 10A, and the intervals thereof are similar to the intervals of the outer layer materials 33 in the above-mentioned pull-on diaper 10A.

Furthermore, plural pieces of elastic members 35 are prepared in parallel, and fed together with the second sheet material 2S in their extended state, and in the state that an adhesive (not shown) fed by an adhesive coating apparatus 215 is applied thereto. The respective elastic member continuous elements 3S are fed at predetermined intervals d2. This adhesive is intermittently fed. For example, as shown in the above-mentioned FIG. 5, the adhesive is applied to the portions of the elastic member continuous elements 3S (the elastic members 35) that are disposed on the respective positions of: the outer edge portions of the absorbent body 40 fixed to the front portion 21 and rear portion 23 of the outer cover 11 that is formed by the second sheet material 2S; the both ends of the waist-surrounding direction of the front portion 21; and the both end portions in the waist-surrounding direction of the rear portion 23. At this time, the elastic member continuous elements 3S are fed so that the center of the lateral direction of the elastic member continuous element 3S corresponds with the center of the lateral direction of the tape-type sheet material 33T.

As the above-mentioned adhesive coating apparatus 215, a hot-melt gun or the like is used, and a hot-melt adhesive is used as the adhesive in this case.

By this, the second sheet material 2S, elastic member continuous elements 3S and tape-type sheet materials 33T are passed between nip rolls 217 and 218. Furthermore, the second sheet material 2S and tape-type sheet materials 33T are partially adhered through the elastic member continuous elements 3S by the hot-melt adhesive applied to the elastic member continuous elements 3S by the pressure between the rolls. The width of the above-mentioned tape-type sheet material 33T, and the intervals of the tape-type sheet materials 33T are in accordance with the above-mentioned pull-on diaper 10A.

Next, a seal processing in which the first sheet material 1S, elastic member continuous elements 3S and second sheet material 2S that are partially adhered are passed through seal rolls 231 in a superposed state is conducted. By these seal rolls 231, sealed portions 37 are formed at intervals on the both sides in the lateral direction of the tape-type sheet materials 33T, and the tape-type sheet materials 33T are fixed on the second sheet material 2S. It is preferable to use emboss bonding for the formation of the sealed portions 37. By using emboss bonding, the drape of the sheet material is not lost by the curing of the adhesive and the like, and thus fine texture can be maintained.

Furthermore, the elastic member continuous elements 3S are present between the tape-type sheet materials 33T and second sheet material 2S and between the seal portions 37 and 37, and are also intermittently fixed to the tape-type sheet materials 33T and second sheet material 2S by the adhesive in the above-mentioned step. Therefore, the major portion of the elastic member continuous elements 3S is free to the tape-type sheet materials 33T and second sheet material 2S. By this, the air-permeability of the tape-type sheet materials 33T (the outer layer materials 33) in the lateral direction can be improved.

Furthermore, in the above-mentioned seal step, the sealed portions 37 are formed in a regulated manner on the portions of the nonwoven fabric where the tape-type sheet materials 33T and the second sheet material 2S form two layers by interposing therebetween the elastic member continuous elements 3S in their extended state, so that gathers (not shown) can be formed by the tape-type sheet materials 33T (outer layer materials 33) when the elastic member continuous elements (the elastic members 35) contract. Namely, the portions between intermittently fixed portions in the tape-type sheet materials 33T are raised outward (the non-skin contact surface side) by the contraction of the elastic members formed of the elastic member continuous elements 3S. By this, the above-mentioned gathers are formed.

By this, the outer cover continuous element 11S that is to be the outer cover 11 is obtained.

Next, the steps on and after the elastic member cutting step using cut rolls 219 as explained in the above-mentioned first aspect are subsequently conducted to thereby complete the pull-on diaper 10 (10B) (for example, see the above-mentioned FIG. 5). In this aspect, in the elastic member cutting step, the elastic members 35 are each cut at one portion on the central position of the area on which the absorber is to be disposed. Alternatively, since the elastic member cutting step is not essential, it is not necessary to cut the elastic members 35.

In the second aspect of the production method of the present invention, similar effects to those of the above-mentioned first aspect can be obtained, and the air-permeability of the areas on which the tape-type sheet materials 33T (the outer layer materials 33) are formed can be improved. Furthermore, gathers can be formed in the lateral direction of the outer layer materials 33 simultaneously with the fixing of the tape-type sheet materials 33T. By this, decorative aesthetic impression can be provided.

Furthermore, in the fixing of the elastic member continuous elements to the first sheet material 1S or second sheet material 2S, and the fixing of the first sheet material 1S and second sheet material 2S, more adhesive becomes unnecessary, and thus it becomes possible to reduce environmental load, and the cost is reduced, as compared to the first aspect.

Next, the third aspect of the production method of the present invention will be explained below, referring to the plane view (1) and the front view (2) showing the main portion of FIG. 15. The third aspect is a method for producing the above-mentioned pull-on diaper 10 (10C).

Figure 15:
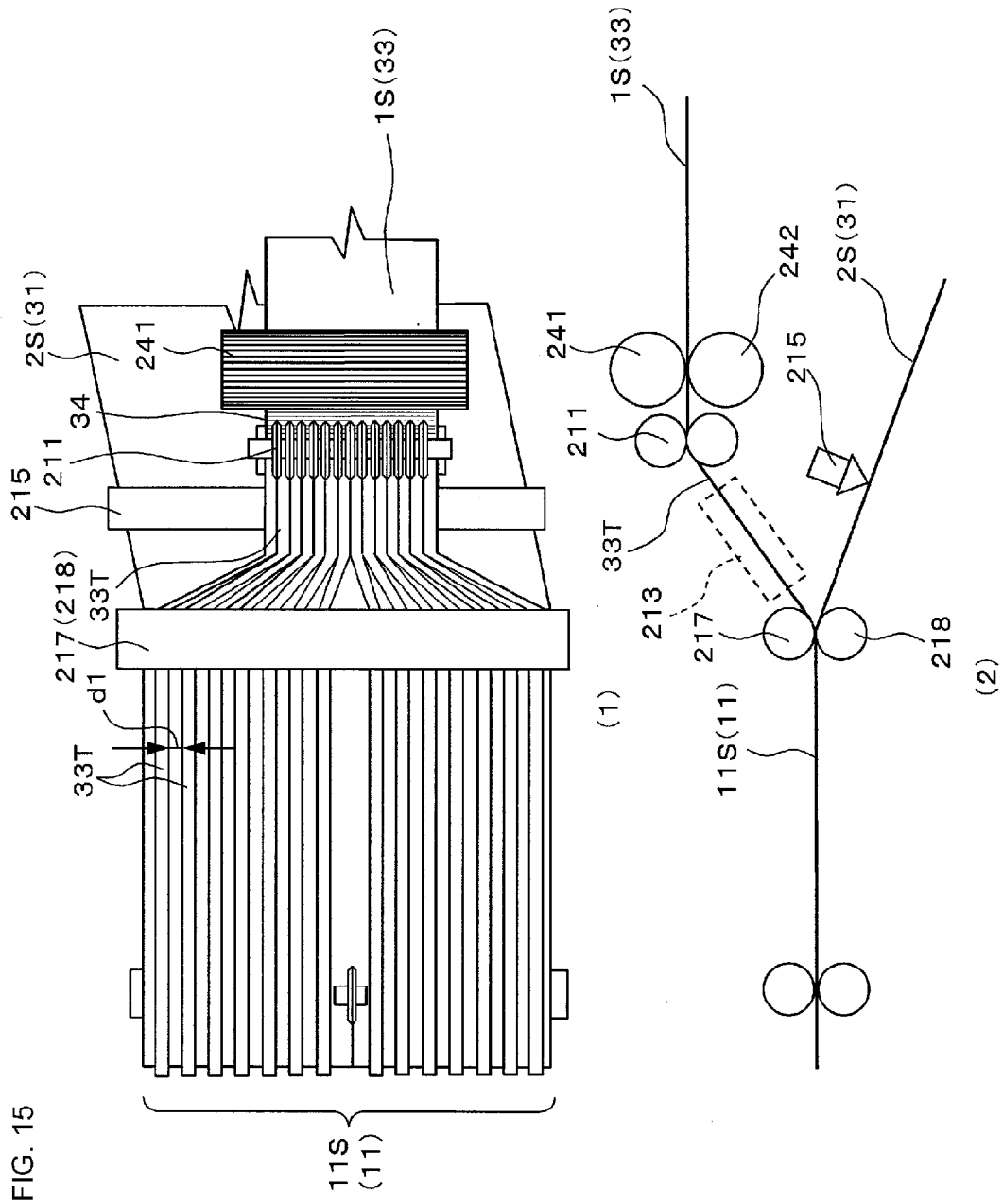
FIG. 15 shows (1) a plane view and (2) a front view, which schematically show the main portions of the production steps of the third aspect according to the method for producing a pull-on wear article of the present invention.

As shown in FIG. 15, a first sheet material 1S is fed from the upper side, and a second sheet material 2S is fed from the lower side. The first sheet material 1S forms outer layer materials 33 and itself has elasticity in the longitudinal direction (waist-surrounding direction). An example is one having a fiber layer on the surface of an elastic sheet. Therefore, as different from the above-mentioned first aspect, elastic members 35 are not used. The second sheet material 2S forms an inner layer material 31.

First, the whole area of the surface of the above-mentioned first sheet material 1S is subjected to a tooth-groove processing as a stretching processing, by using a concavo-convex roll 241. As a result, grooves 34 (illustration after the slitting of the first sheet material 1S is omitted) are imparted to the first sheet material 1S in the lateral direction. By this tooth-groove processing, extensibility is imparted to the fiber layer in the first sheet material 1S in the longitudinal direction thereof, without inhibiting the elasticity of the elastic sheet, to thereby allow the first sheet material 1S to express elasticity. The intervals of the grooves 34 are adjusted depending on the thickness of the nonwoven fabric of the first sheet material 1S, and for example, adjusted to intervals that are in accordance with the above-mentioned pull-on diaper 10C. Furthermore, a concavo-convex roll 242 that engages with the concavo-convex roll 241 is disposed on the position corresponding to the roll 241.

Next, the first sheet material 1S that has undergone the above-mentioned tooth-groove processing is divided into plural pieces by an outer layer material slit cutter 211 to give tape-type sheet materials 33T. Furthermore, the tape-type sheet materials 33T and 33T are spaced apart at predetermined intervals d1 by a similar spacing means 213 to that explained in the above-mentioned first aspect. The width of the tape-type sheet material 33T, and the intervals of the tape-type sheet materials 33T are in accordance with the above-mentioned pull-on diaper 10A. In addition, the above-mentioned tooth-groove processing can be conducted after dividing the first sheet material 1S into plural pieces by the outer layer material slit cutter 211.

On the other hand, the second sheet material 2S is fed in the state that the adhesive (not shown) fed by the adhesive coating apparatus 215 is applied thereto. It is preferable that the adhesive is fed to approximately the center portion of the position to which each of the tape-type sheet materials 33T is attached in the subsequent step, and the method for feeding may be continuous or intermittent.

By this, the tape-type sheet materials 33T are fed with predetermined intervals onto the second sheet material 2S between the nip rolls 217 and 218. Furthermore, by passing the above-mentioned second sheet material 2S and tape-type sheet materials 33T between the nip rolls 217 and 218, the second sheet material 2S and tape-type sheet materials 33T are adhered by the adhesive applied to the second sheet material 2S by the pressure between the rolls.

As a result, an outer cover continuous element 11S that is to be an outer cover 11 is obtained.

Next, the steps on and after the step of cutting the outer cover using the outer cover slit cutter 221 explained in the first aspect of the above-mentioned production method of present invention are subsequently conducted to thereby complete the pull-on diaper 10 (10C) (for example, see the above-mentioned FIG. 6).

In the third aspect of the production method of the present invention, similar effects to those in the above-mentioned first aspect can be obtained. Furthermore, since elasticity is imparted to the tape-type sheet materials 33T themselves, it is not necessary to dispose elastic members between the first sheet material 1S (the outer layer materials 33) and the second sheet material 2S (the inner layer material 31), and this enables reduction of the materials and reduction of the material costs.

Figure 16:
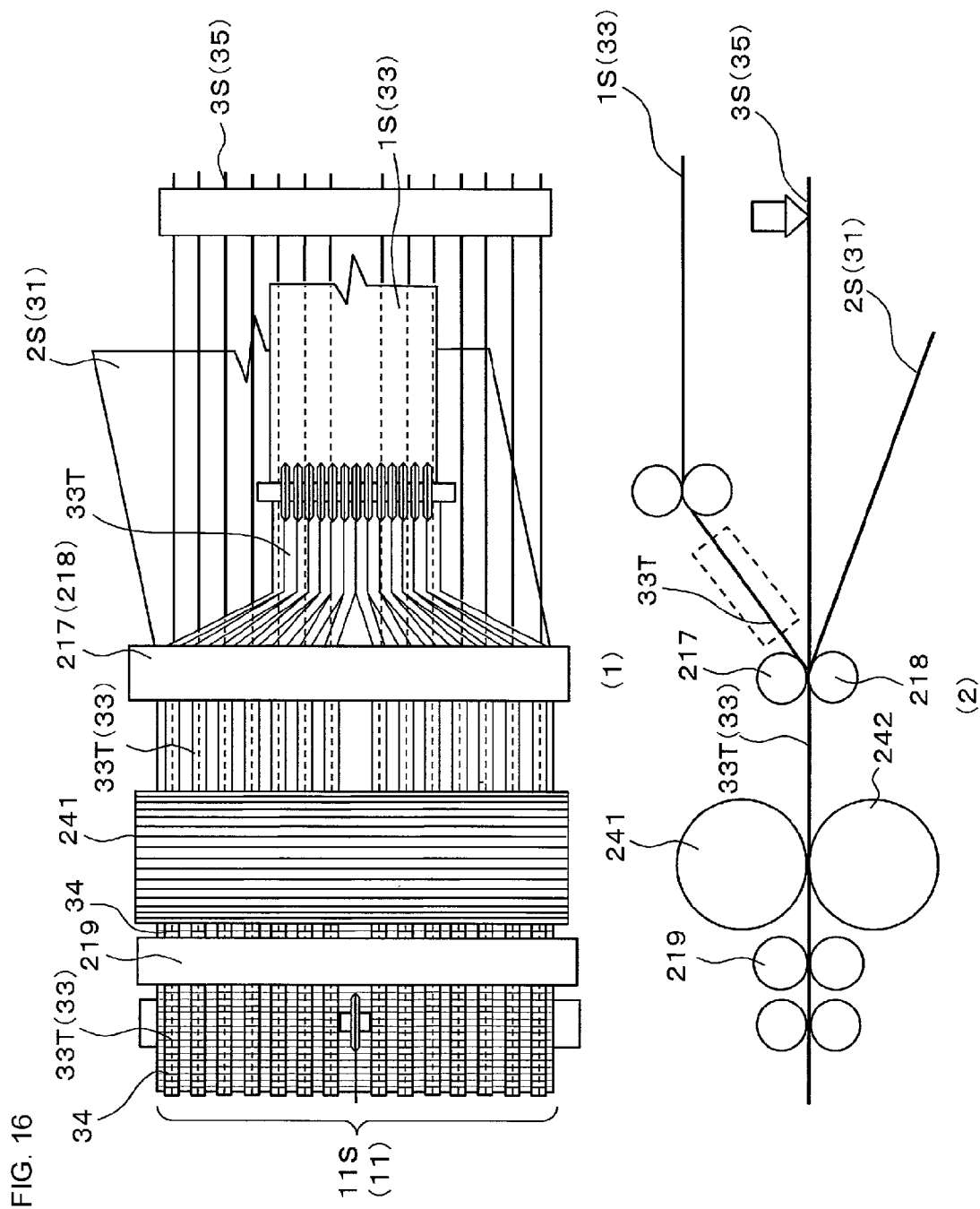
FIG. 16 shows (1) a plane view and (2) a front view, which schematically show the main portions of the production steps of the fourth aspect according to the method for producing a pull-on wear article of the present invention.

Next, the fourth aspect of the production method of the present invention will be explained below, referring to the plane view (1) and the front view (2) showing the main portion of FIG. 16. The fourth aspect is a method for producing the above-mentioned pull-on diaper 10 (10D).

The fourth aspect is a production method comprising conducting a tooth-groove processing as a stretching step, between the step of adhering the second sheet material 2S to be the second sheet material 2S and the tape-type sheet materials 33T (the first sheet material 1S) to be the outer layer materials 33, through the elastic member continuous elements 3S by the nip rolls 217 and 218, and the step of cutting the elastic members by the cut roll 219, in the above-mentioned first aspect. The fourth aspect is similar to the above-mentioned first aspect except that the tooth-groove processing is conducted. The tooth-groove processing as used herein is a step of imparting extensibility to the fiber layer without inhibiting, for example, the extensibility of the extensible sheet constituting the outer layer materials 33, by pressing the blades of the concavo-convex roll 241 against the tape-type sheet materials 33T and inner layer material 31. As a result, grooves 34 are imparted to the tape-type sheet materials 33T at intervals. It is preferable that the intervals of the grooves 34 are adjusted to, for example, similar intervals to those of the grooves of the above-mentioned pull-on diaper 10C. Furthermore, a concavo-convex roll 242 that engages with the concavo-convex roll 241 is disposed on the position corresponding to the roll 241.

At first, in a similar manner to the above-mentioned first aspect, narrow tape-type sheet materials 33T, which are obtained by dividing a first sheet material 1S into plural pieces, are attached to the second sheet material 2S (the inner layer material 31). For example, the tape-type sheet materials 33T are inelastic nonwoven fabric. Subsequently, the tape-type sheet materials 33T and inner layer material 31, which are adhered through intervening the elastic member continuous elements 3S, are subjected to a tooth-groove processing as a stretching processing by a concavo-convex roll 241. By this, extensibility is exhibited in the longitudinal direction of the tape-type sheet material 33T and inner layer material 31 so that the elasticity of the elastic member continuous elements 3S is not inhibited. The tooth-groove processing does not affect the elasticity of the elastic member continuous elements 3S. As a result of conducting this tooth-groove processing, concavo-convex (the concave is grooves 34) is imparted to the surfaces of the above-mentioned tape-type sheet materials 33T in the lateral direction. The intervals of the grooves 34 are adjusted depending on the thickness of the nonwoven fabric of the first sheet material 1S, and for example, adjusted to intervals in accordance with the case of the above-mentioned pull-on diaper 10C. In addition, in the above-mentioned stretching processing, the method of processing is not limited to the tooth-groove processing as long as it is a method to make the tape-type sheet materials 33T and inner layer material 31 extensible.

In the above-mentioned fourth aspect, similar effects to those in the above-mentioned first aspect can be obtained. Furthermore, since extensibility is exhibited in the tape-type sheet materials 33T (the outer layer materials 33) and inner layer material 31, elasticity can be imparted to the waist-surrounding direction of an outer cover 11 (see the above-mentioned FIG. 7) of the pull-on diaper. Furthermore, gathers are easily formed by forming the grooves 34 on the tape-type sheet materials 33T.

Next, the fifth aspect of the production method will be explained below, referring to the schematic perspective view of FIG. 17. The fifth aspect is another production method for producing the above-mentioned pull-on diaper 10 (10A).

Figure 17:
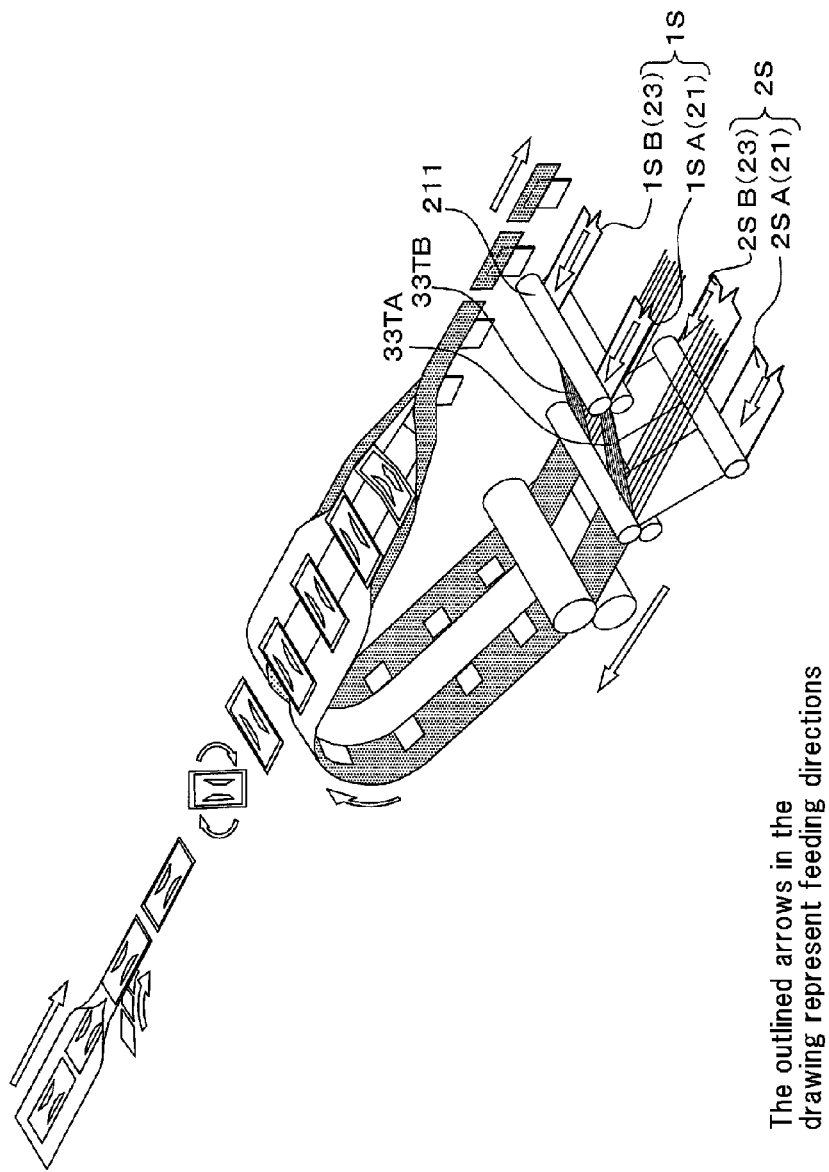
FIG. 17 shows a perspective view showing the overview of the production steps of the fifth aspect according to the method for producing a pull-on wear article of the present invention.

As shown in FIG. 17, in the fifth aspect, a first sheet material 1S is fed in the state of being divided in advance into a first sheet material 1SA to form a front portion 21 of an outer cover 11 and a first sheet material 1SB to form a rear portion 23. Similarly, a second sheet material 2S is fed in the state of being divided into a second sheet material 2SA to form the front portion 21 and a front portion 21 to form the rear portion 23. Furthermore, the above-mentioned first sheet materials 1SA and S1B are respectively divided into plural pieces by an outer layer material slit cutter 211 to thereby give tape-type sheet materials 33TA and 33TB. Furthermore, the tape-type sheet materials 33TA and 33TA, and the tape-type sheet materials 33TB and 33TB are respectively spaced apart at predetermined intervals by a spacing means 213. The widths of the tape-type sheet materials 33TA and 33TB (the divided first sheet materials 1SA and 1SB) are similar to the width of the outer layer material 33 of the above-mentioned pull-on diaper 10A, and the intervals thereof are also similar to the intervals of the outer layer materials 33 of the above-mentioned pull-on diaper 10A.

The subsequent steps are similar to those in the above-mentioned first aspect except that a step of cuffing the outer cover continuous element 11S using an outer cover slit cutter is not conducted.

In the above-mentioned fifth aspect, similar effects to those of the above-mentioned first aspect can be obtained. In addition, since the first sheet material 1S is fed in the state of being divided in advance into the first sheet materials 1SA and 1SB, and the second sheet material 2S is fed in the state of being divided into the second sheet materials 2SA and 2SB, it is not necessary to install an outer cover slit cutter. Therefore, the production facilities can be reduced, and the production cost can be reduced.

The method comprising feeding the first sheet material 1SA and first sheet material 1SB in the divided state as in the fifth aspect of the production method can be applied to the above-mentioned second to fourth aspects. In either case, the subsequent steps are similar to those of the above-mentioned second to fourth aspects, respectively, except that the step of cutting the outer cover continuous element 11S using an outer cover slit cutter is not conducted.

Next, a preferable embodiment (the second embodiment) of the method for producing a pull-on diaper according to the present invention will be explained below, referring to the schematic perspective view of FIG. 18. The second embodiment is an example in which the production method of the present invention is applied to a method for producing a conventional pull-on diaper having leg holes, and is a method for producing the above-mentioned pull-on diaper 100.

Figure 18:
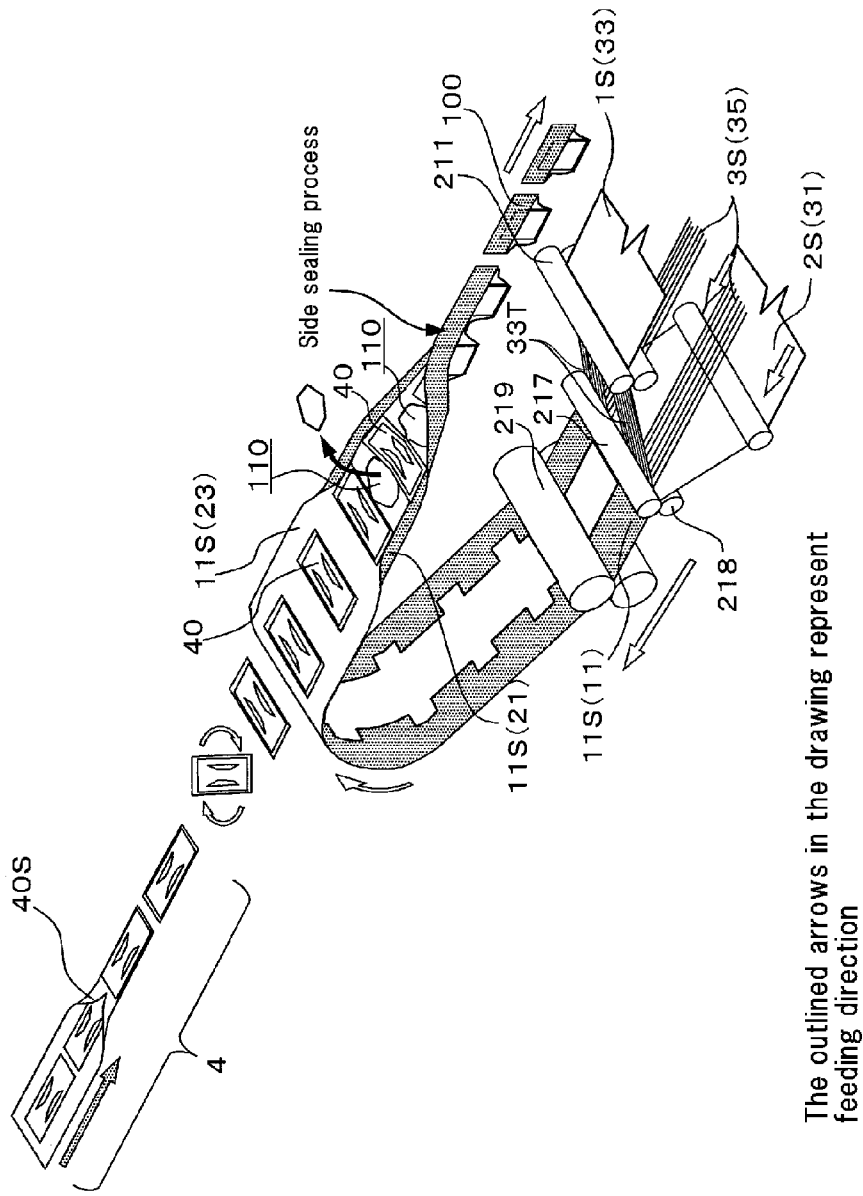
FIG. 18 shows a perspective view showing the overview of the production steps according to a preferable embodiment (the second embodiment) of the method for producing a pull-on wear article of the present invention.

As shown in FIG. 18, a first sheet material 1S is fed from the upper side and a second sheet material 2S is fed from the lower side, and elastic member continuous elements 3S that are to be elastic members 35 are simultaneously fed to the gap between the first sheet material 1S and second sheet material 2S. The first sheet material 1S forms outer layer materials 33, and the second sheet material 2S forms an inner layer material 31. For these first sheet material 1S (outer layer materials 33), second sheet material 2S (inner layer material 31) and elastic member continuous elements 3S (elastic members 35), similar materials to those respectively explained in the first example of the pull-on diaper are used.

At first, the first sheet material 1S is divided into plural pieces by an outer layer material slit cutter 211 to form tape-type sheet materials 33T. Next, the tape-type sheet materials 33T and 33T are spaced apart at predetermined intervals d1 by a similar spacing means (not shown) to that in the above-mentioned first aspect of the first embodiment. The width of the tape-type sheet material 33T (the divided first sheet material 1S) is formed into a similar width to that of the outer layer material 33 in the above-mentioned pull-on diaper 10A, and the intervals during the spacing are also formed into similar intervals to those of the outer layer materials 33 of the above-mentioned pull-on diaper 10A.

Furthermore, plural pieces of elastic member continuous elements 3S are prepared in parallel, and fed to the gap between the second sheet material 2S and respective spaced tape-type sheet materials 33T in the state that the respective elastic member continuous elements 3S are elongated, and in the state that an adhesive (not shown) fed by a similar adhesive coating apparatus (not shown) as explained in the above-mentioned first aspect is applied. At this time, it is preferable that the tape-type sheet materials 33T and elastic member continuous elements 3S are fed so that the center of the lateral direction of the elastic member continuous element 3S correspond with the center of the lateral direction of the above-mentioned tape-type sheet material 33T. For example, a hot-melt gun is used as the above-mentioned adhesive coating apparatus (not shown), and a hot-melt adhesive is used as the adhesive in this case.

By this, the second sheet material 2S, elastic member continuous elements 3S and tape-type sheet materials 33T are passed between nip rolls 217 and 218. Furthermore, the second sheet material 2S and tape-type sheet materials 33T are adhered through elastic member continuous elements 3S by the hot-melt adhesive attached to the elastic member continuous elements 3S by the pressure between the rolls to thereby give an outer cover continuous element 11S that is to be an outer cover 11.

Subsequently, a step of cutting the elastic members, which disables the exhibition of the elastic function of the elastic member continuous elements 3S on the area to which an absorbent body 40 is to be attached in the following step, is conducted by a cut roll 219. The method for cutting is similar to that in the above-mentioned first aspect.

Next, in a similar manner to the above-mentioned first aspect, the absorbent body 40, which is obtained by cutting an absorbent body continuous material 40S that is fed from an absorbent body forming portion 4, is disposed on the predetermined positions of the front portion 21 and rear portion 23 of the outer cover continuous element 11S. Subsequently, the both ends of the lateral direction of the outer cover continuous element 11S are folded back so as to cover the both end portions of the longitudinal direction of the absorbent body 40, and the absorbent body 40 is fixed on the folded-back portions.

Next, leg holes 110 are opened at the portions of the both lateral side of the absorbent body 40 fixed on the outer cover continuous element 11S.

Next, the longitudinal direction of the absorbent body 40 is folded in the two and the front portion 21 of the outer cover continuous element 11S and the rear portion 23 of the outer cover continuous element 11S are superposed by orienting the second sheet material 2S to face inward, and the steps on and after the side seal step for bonding the front portion 21 and rear portion 23 at predetermined intervals in the lateral direction thereof are conducted to thereby complete the pull-on diaper 100.

In the above-mentioned second embodiment of the production method, since single layer regions formed of the inner layer material 31 are formed on a part of the outer cover 11 in a similar manner to the above-mentioned first aspect, the air permeability at the single layer area is markedly increased, and thus the pull-on diaper 100 in which the steaminess is significantly reduced can be provided.

Furthermore, since the use amount of the outer layer materials 33 can be decreased, a so-called environment-friendly product can be produced in a disposable-type pull-on diaper. In addition, since the use amount of the outer layer materials 33 can be decreased, the production cost can be reduced.

As explained above, according to the pull-on wear article and the method for producing the pull-on wear article of the present invention, the air permeability of the pull-on wear articles 10 and 100 can be markedly improved since the inner layer material 31 forms single layer areas at the portions without the outer layer materials 33 by disposing the outer layer materials at intervals in the direction of length.

In the above-mentioned production method, a production method in which the tape-type sheet materials 33T are adhered to the second sheet material 2S at the adhered positions with higher precision is expected. Such production method includes a method for producing the pull-on wear article of the present invention as mentioned below. Hereinafter the production method will be explained as a method for producing a pull-on diaper.

The first aspect of a preferable embodiment (the first embodiment) of the method for producing a pull-on diaper of present invention will be explained below, referring to FIG. 19 to FIG. 23. This first aspect is a method for producing the above-mentioned pull-on diaper 10. For the points that are not specifically explained in the other aspects mentioned below, the explanations described in detail in the first aspect are suitably applied.

Figure 20:
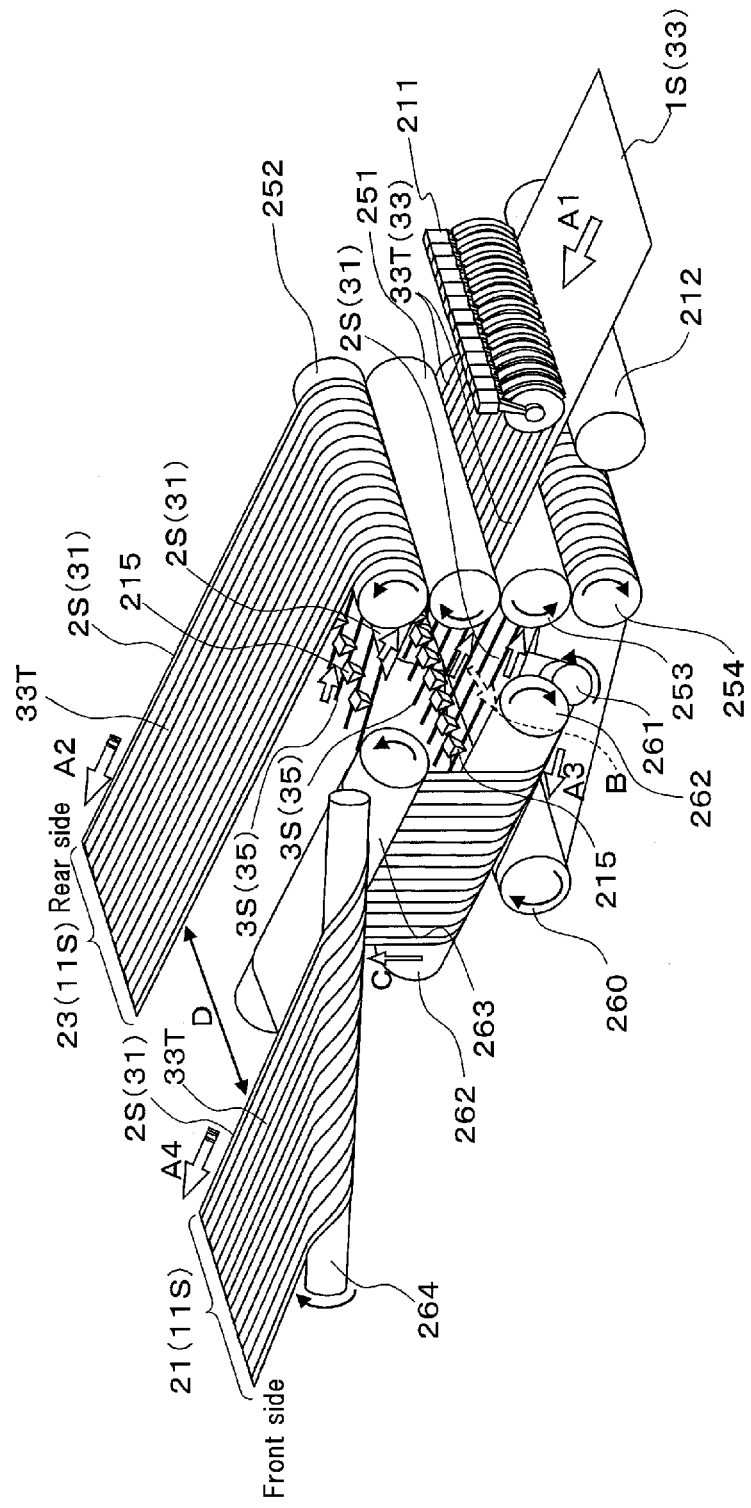
FIG. 20 shows a perspective view of the main portion showing the method for producing of the pull-on wear article of the first aspect of the third embodiment.
Figure 21:
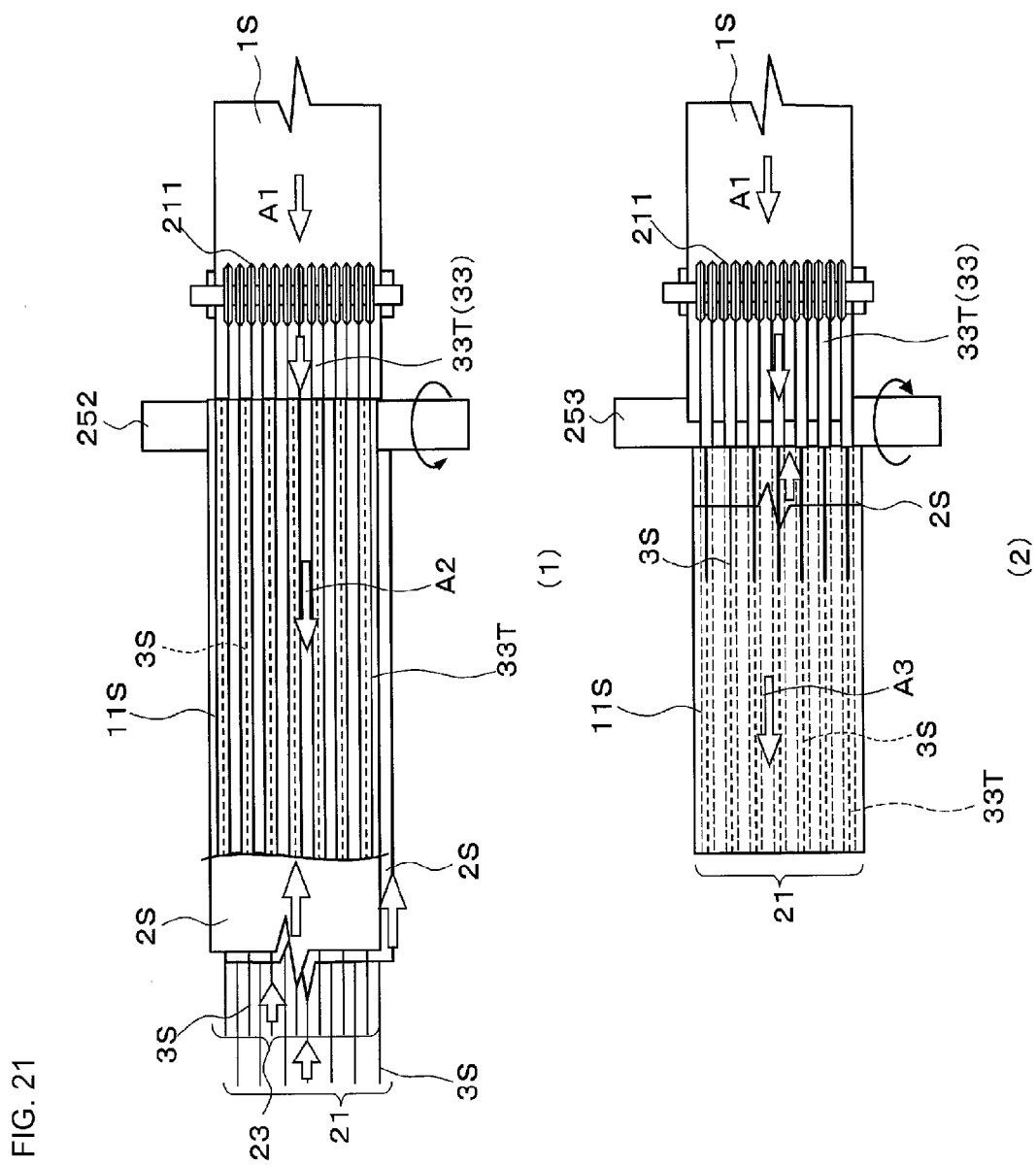
FIG. 21 shows plane views of the main portions of the method for producing a pull-on wear article of the first aspect of the third embodiment, in which (1) is a plane view of the main portion, wherein the first sheet material and the second sheet material to be disposed on the rear portion are seen from the upper side, and (2) is a plane view of the main portion, wherein the first sheet material and the second sheet material to be disposed on the front portion, which is positioned below the lower side of first separation roll, are seen from the upper side.
Figure 22:
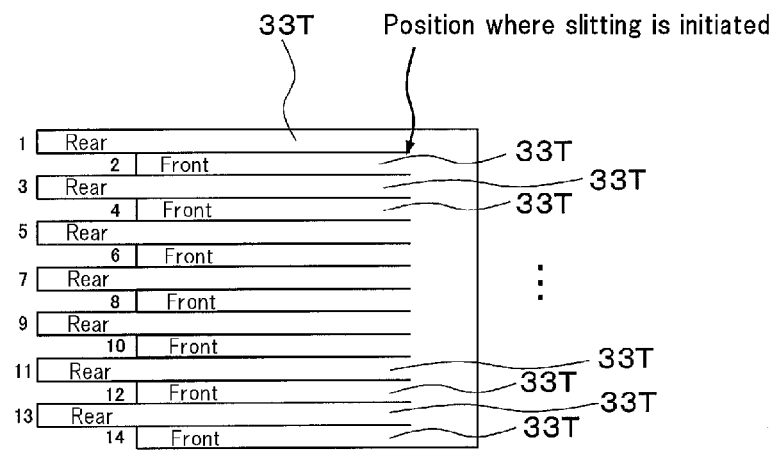
FIG. 22 shows a top view showing the slit state of the tape-type sheet materials of the first aspect of the third embodiment.
Figure 23:
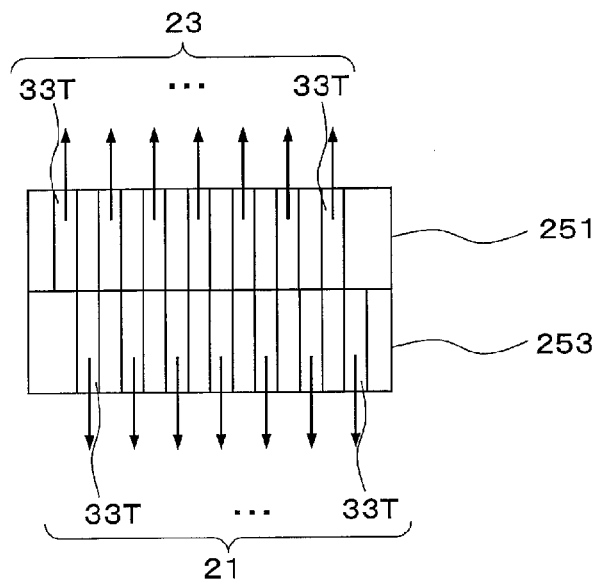
FIG. 23 shows a side view showing the separation state of the tape-type sheet materials on the separation roll of the first aspect of the third aspect.

FIG. 21 is a drawing showing plane views of the main portions in FIG. 20, wherein FIG. 21 (1) is a plane view of the main portion of the first sheet material 1S and the second sheet material 2S to be disposed on the rear portion 23, which is seen from the upper side, and FIG. 21 (2) is a plane view of the main portion of the first sheet material 1S and the second sheet material 2S to be disposed on the front portion 21 which is at the lower side than a lower side first separation roll 253, which is seen from the upper side. By this FIG. 21, the dispositional relationship between the second sheet material 2S and tape-type sheet materials 33T and the dispositional relationship between the tape-type sheet materials 33T and elastic member continuous element 3S are clarified. The tape-type refers to a state of a narrow and long band-like sheet, and the slitting refers to dividing the sheet material plurally in the lateral direction to give a form of plural pieces of tapes. In the present invention, the sheet material is cut along the feeding direction (the direction of arrow A1 mentioned below) to thereby be divided into plural pieces in the lateral direction of the sheet material.

Figure 19:
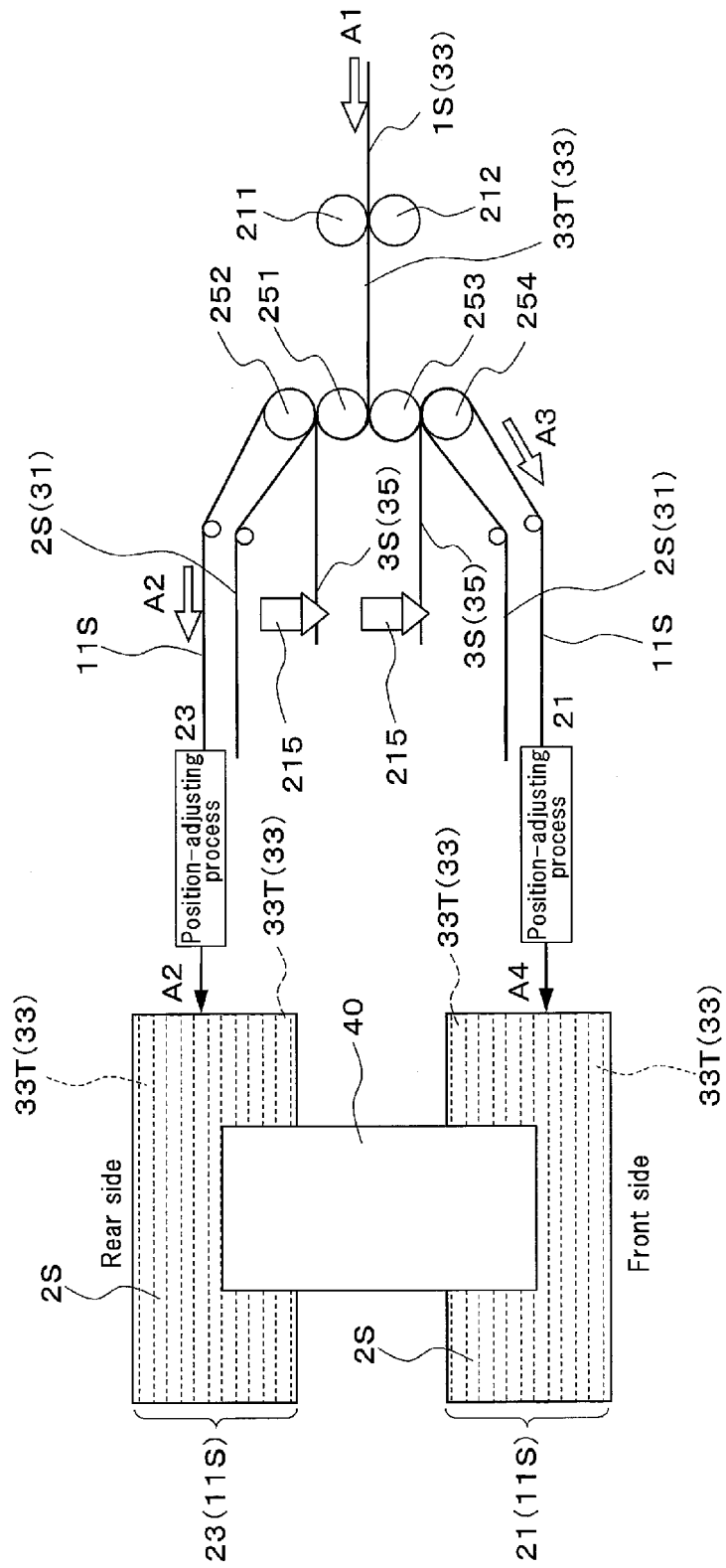
FIG. 19 shows a schematic view of the production steps showing the first aspect of a preferable embodiment (the third embodiment) of the method for producing a pull-on wear article of the present invention.

As shown in FIG. 19 to FIG. 21, the first sheet material 1S is fed in the direction of the arrow A1. This first sheet material 1S constitutes outer layer materials 33. This first sheet material 1S is slitted by an outer layer material slit cutter 211 and divided into plural pieces to form narrow tape-type sheet materials 33T (outer layer materials 33). For example, the respective tape-type sheet materials 33T are slitted into even widths (see FIG. 22 for the specifics).

Furthermore, the respective tape-type sheet materials 33T are fed to the gap between an upper-side first separation roll 251 and the lower-side first separation roll 253 in the state that the positions in the lateral direction of the respective tape-type sheet materials 33T during the slitting are maintained. The plural pieces of tape-type sheet materials 33T fed to the gap of the rolls are alternately selected one by one and wound around the upper-side first separation roll 251 and lower-side first separation roll 253 to be separated into different directions (for example, upper direction and lower direction). Specifically, the plural pieces of tape-type sheet materials 33T are alternately separated one by one into tape-type sheet materials for the front side and for the rear side (see FIG. 23 for the specifics). The above-mentioned different directions refer to a direction that gets away from the first sheet material 1S at the side of the first surface that is one of the two surfaces possessed by the first sheet material 1S, and a direction that gets away from the first sheet material 1S at the side of the second surface that is opposite to the first surface, with respect to the first sheet material 1S fed to the separation position. In other words, the different directions may be two directions that get away from the both surfaces of the first sheet material 1S toward each opposite direction across the first sheet material 1S, and the directions are not necessarily directly opposite directions. Therefore, the directions are not limited to the above-mentioned upper direction and lower direction, and can also be different two directions in a plane that is orthogonal to the respective rotation axes of the upper-side first separation roll 251 and lower-side first separation roll 253. Furthermore, the disposition directions of the respective rotation axes of the upper-side first separation roll 251 and lower-side first separation roll 253 each may have an angle such as 90° with respect to the horizontal direction. In the case, the upper side and lower side change into the right side and left side, but in the present embodiment they are referred to as the upper side and lower side for the sake of convenience. In the present embodiment, the different directions refer to the directions that go toward the respective rolls of the upper-side first separation roll 251 and lower-side first separation roll 253.

When the tape-type sheet materials 33T for the rear side, which have wound around the upper-side first separation roll 251 and have been separated toward the upper direction, wind around an upper-side second separation roll 252, the second sheet material 2S is fed, from fed from the direction opposite to the feeding direction of the first sheet material 1S (the direction of an arrow A), to the gap between the upper-side first separation roll 251 and upper-side second separation roll 252 so as to directly wind around the upper-side second separation roll 252. This second sheet material 2S constitutes the inner layer material 31. Furthermore, plural pieces of elastic member continuous elements 3S are prepared in parallel, and fed together with the second sheet material 2S in the state that the respective elastic member continuous elements are extended, and in the state that an adhesive (not shown) fed by an adhesive coating apparatus 215 is applied thereto. At this time, for example, they are fed so that the center of the lateral direction of the elastic member continuous elements 3S is positioned on the center of the lateral direction of the tape-type sheet material 33T. The elastic member continuous elements 3S constitute elastic members 35. For example, a hot-melt gun is used as the above-mentioned adhesive coating apparatus 215, and a hot-melt adhesive is used as the adhesive in this case.

By this, a pressure is applied between the upper-side first separation roll 251 and upper-side second separation roll 252, and the tape-type sheet materials 33T are adhered onto the second sheet material 2S through the elastic member continuous elements 3S by the adhesive applied to the elastic member continuous elements 3S. At this time, the tape-type sheet materials 33T are conveyed while winding around the roll surface of the upper-side first separation roll 251 without slipping, and thus the positions in the lateral direction of the respective tape-type sheet materials 33T during the slitting are maintained. In this state, the tape-type sheet materials 33T are adhered to the second sheet material 2S without getting away from the upper-side first separation roll 251. As a result, an outer cover continuous element 11S that is to be the rear portion 23 formed of the second sheet material 2S to which the tape-type sheet materials 33T are adhered through the elastic member continuous elements 3S, is constituted. Furthermore, the both sides of the outer cover continuous element 11S for the rear portion 23 are inverted in the state that the outer cover continuous element 11S is winding around the upper-side second separation roll 252, and the outer cover continuous element 11S is fed in the direction of an arrow A2.

On the other hand, when the tape-type sheet materials 33T for the front side, which have wound around the lower-side first separation roll 253 and have been separated toward the lower direction, wind around a lower-side second separation roll 254, the second sheet material 2S is fed, from the direction opposite to the feeding direction of the first sheet material 1S (the direction of an arrow A1), to the gap between the lower-side first separation roll 253 and lower-side second separation roll 254 so as to directly wind around the lower-side second separation roll 254. Furthermore, plural pieces of elastic member continuous elements 3S are prepared in parallel, and fed together with the second sheet material 2S in the state that the respective elastic member continuous elements are extended, and in the state that an adhesive (not shown) that is fed by an adhesive coating apparatus 215 is applied thereto. At this time, it is preferable that they are fed so that the center of the lateral direction of the elastic member continuous element 3S is positioned on the center of the lateral direction of the above-mentioned tape-type sheet material 33T. For example, a hot-melt gun is used as the above-mentioned adhesive coating apparatus 215, and a hot-melt adhesive is used as the adhesive in this case.

In the adhesive coating apparatus 215, although individual hot-melt guns are used for the respective elastic member continuous elements 3S, it is also preferable to use an integrated-type hot-melt gun (not shown) having plural nozzles from which an adhesive is ejected to the positions corresponding to the elastic continuous elements 3S.

Furthermore, the adhesive may be applied to the surface of the second sheet material 2S on the positions where the elastic member continuous elements 3S are disposed rather than being applied to the elastic member continuous elements 3S. The application may be continuous or intermittent.

Furthermore, the upper-side first and second separation rolls 251 and 252, and the lower-side first and second separation rolls 253 and 254 are rotatable rolls, and the upper-side first separation roll 251 and lower-side first separation roll 253 are made rotatable by a rotation driving means that is not depicted. Examples of the rotation driving means may include a motor. Furthermore, it is preferable that the rotatable rolls each has a surface with a large friction force such as a roughened surface or rubber on the circumferential surface of the roll so that the sheet is fed at the circumferential velocity thereof.

In addition, the upper-side second separation roll 252 and lower-side second separation roll 254 may be rolls that are rotated by a rotation driving means. In this case, the rotation driving means is rotated at an equivalent circumferential velocity to the circumferential velocities of the upper-side first separation roll 251 and lower-side first separation roll 253.

By this, a pressure is applied between the lower-side first separation roll 253 and lower-side second separation roll 254, and the tape-type sheet materials 33T are adhered onto the second sheet material 2S through the elastic member continuous elements 3S by the adhesive applied to the elastic member continuous elements 3S. At this time, the tape-type sheet materials 33T are conveyed by winding around the rolling surfaces of the lower-side first separation roll 253 without slipping, and thus are adhered to the second sheet material 2S in the state that the positions in the lateral direction of the respective tape-type sheet materials 33T during the slitting are maintained. As a result, an outer cover continuous element 11S that is to be the front portion 21 formed of the second sheet material 2S to which the tape-type sheet materials 33T are adhered through the elastic member continuous elements 3S, is constituted. Furthermore, the both sides of the outer cover continuous element 11S for the front portion 21 are inverted in the state that outer cover continuous element 11S is winding around the lower-side second separation roll 254, and the outer cover continuous element 11s is fed in the direction of an arrow A3. Since the tape-type sheet materials 33T are alternately separated in the upper and lower directions, the positional relationships of the respective dispositions of the tape-type sheet materials 33T separated in the upper direction and the tape-type sheet materials 33T separated in the lower direction on the second sheet material 2S are different. Therefore, in the case where the positions of the tape-type sheet materials 33T disposed on the second sheet material 2S for the rear side and the positions of the tape-type sheet materials 33T disposed on the second sheet material 2S for the front side are mated on the rear side and front side, the feeding positions of the tape-type sheet materials 33T to be disposed on the second sheet material 2S for the rear side and the feeding positions of the tape-type sheet materials 33T to be disposed on the second sheet material 2S for the front side are different. Therefore, by adjusting at least either one of the feeding positions of the second sheet materials 2S (for example, by displacing either one of the second sheet materials 2S in the lateral direction thereof), the positional relationship of the tape-type sheet materials 33T disposed on the second sheet material 2S for the rear side and the positional relationship of the tape-type sheet materials 33T that are disposed on the second sheet material 2S for the front side can be conformed.

Furthermore, in the respective second sheet materials 2S for the rear side and front side to which the tape-type sheet materials 33T are adhered, the positions of the tape-type sheet materials 33T disposed in the lateral directions of the respective second sheet materials 2S may differ in case of applying to a diaper.

As explained above, in order for the tape-type sheet materials 33T to be adhered to the second sheet material 2S through the elastic member continuous elements 3S to which the adhesive is applied, it is necessary that the second sheet material 2S, elastic member continuous elements 3S and tape-type sheet materials 33T are laminated from the same direction in this order, and fed to the gap between the upper-side first and second separation rolls 251 and 252 and the gap between the lower-first and second separation rolls 253 and 254. By feeding in such way, attachment of the adhesive applied to the elastic member continuous elements 3S to the roll surfaces can be prevented.

Next, the positions of the respective outer cover continuous elements 11S on the front portion 21 and rear portion 23 are adjusted to give a predetermined interval D. In this step of adjusting the positions, for example, the position of the outer cover continuous element 11S for the front portion 21 is adjusted. Specifically, the feed direction of the outer cover continuous element 11S for the front portion 21 is adjusted to the direction (the direction of the arrow A4) that is in parallel to the feed direction (the direction of the arrow A2) of the outer cover continuous element 11S for the rear portion 23, and the surface on the side of the second sheet material 2S of the outer cover continuous element 11S for the front portion 21 and the surface on the side of the second sheet material 2S of the outer cover continuous element 11S for the rear portion 23 are adjusted to be in the same planar direction (for example, the upper surface) and at the same height.

At first, the both surfaces of the outer cover continuous element 11S for the front portion 21 are inverted by an invert roll 260 whose roll axis is disposed in the direction at right angles to the feed direction (the direction of an arrow A3) of the outer cover continuous element 11S of the front portion 21. By this inversion, the feed direction is also inverted. Subsequently, in order that the feed direction become the direction of the arrow B that is changed to the lateral direction (preferably the 90° direction) with respect to the inverted feed direction, the both surface of the outer cover continuous element 11S for the front portion 21 are inverted by a first roll 261 whose roll axis is disposed at a predetermined angle (for example, 30° to 60°, preferably 45°) with respect to the above-mentioned inverted feed direction, and the feed direction is adjusted to the direction of an arrow B. Subsequently, the feed direction of the outer cover continuous element 11S for the front portion 21 is changed from the horizontal direction to the vertical direction of an arrow C by a second roll 262. Subsequently, the feed direction of the outer cover continuous element 11S for the front portion 21 is changed from the vertical direction to the horizontal direction by a third roll 263. Next, the both surfaces of the outer cover continuous element 11S for the front portion 21 are inverted by a fourth roll 264 whose roll axis is disposed at a predetermined angle (for example, 30° to 60°, preferably 45°) with respect to the feed direction of the outer cover continuous element 11S for the front portion 21, to thereby direct the surface on the side of the second sheet material 2S of the outer cover continuous element 11S for the front portion 21 and the surface on the side of the second sheet material 2S of the outer cover continuous element 11S for the rear portion 23 toward the same planar direction (the upper surface), and the surfaces are positioned at the same height, and the feed direction is changed to the lateral direction (for example, the 90° direction is preferable) to thereby give the feed direction in the direction of an arrow A4, which is in parallel to the outer cover continuous element 11S for the rear portion 23.

In the first and third rolls 261 and 263, the surfaces on the side of the second sheet material 2S of the respective outer cover continuous elements 11S on the front portion 21 and rear portion 23 are adjusted to be at the same height, by adjusting the interval of the respective outer cover continuous elements 11S on the front portion 21 and rear portion 23 to a predetermined interval D, and adjusting the interval of the second and fourth roll 262 and 264 with consideration for the roll diameters of the first and third rolls 261 and 263. Furthermore, since the first and fourth rolls 261 and 264 are so-called turn rolls, they do not rotate, and have such roll surfaces that the sheet slides thereon. The invert roll 260, second roll 262 and third roll 263 are rotatable rolls, and may also be rolls that are rotation-driven by a rotation driving means that is not depicted. Examples of the rotation driving means may include a motor. Furthermore, it is preferable that the rotatable rolls each has a surface with a large friction force such as a roughened surface or rubber on the circumferential surface of the roll so that the sheet is fed at the circumferential velocity thereof. Furthermore, it is preferable that the circumferential velocity of each roll is a constant velocity so that the sheet would not be extremely drawn or slacked off.

The roll constitution of the above-mentioned invert roll 260 and first to fourth rolls 261 to 264 is an example, and another roll constitution can also be adopted as long as the surfaces on the side of the second sheet material 2S of the respective outer cover continuous element 11S for the front portion 21 and rear portion 23 can be directed toward the same planar direction and positioned at the same height, to thereby obtain the feed direction in the direction that the respective outer cover continuous elements 11S on the front portion 21 and rear portion 23 are in parallel.

Besides the above-mentioned method by only the combination of the rolls, the following is exemplified as a method for adjusting the positions of the respective outer cover continuous elements 11S to be disposed on the front portion 21 and rear portion 23 at the predetermined interval D: the both surfaces of the second sheet material 2S to which the tape-type sheet materials 33T on the front side are attached are inverted, and the second sheet 2S disposed on the rear side and the second sheet 2S disposed on the front side are adjusted by using a spacing means (not shown) to be in the state that the tape-type sheet materials 33T are disposed on the surface side (or the rear surface side) and to be fed in parallel to each other in a planar view, in a similar manner to the method for producing the pull-on diaper 10 as explained by the above-mentioned FIGS. 10 to 13. Furthermore, the height of the second sheet material 2S disposed on the rear side and the height of the second sheet material 2S disposed on the front side may be adjusted to the same height by using rolls (not shown).

Subsequently, in similar manners to the steps as explained in the above-mentioned example of the production method, the steps on and after the lamination step of an absorbent body 40 so as to bridge between the second sheet materials 2S of the respective outer cover continuous elements 11S on the front portion 21 and rear portion 23 are conducted. In addition, prior to the lamination of the absorbent body 40, a step of cutting the elastic members that disables the expression of the elastic function of the elastic member continuous elements 3S on the portion of the second sheet material 2S to which the absorbent body 40 is attached may also be conducted, in a similar manner to that explained in the example of the above-mentioned production method.

As a result, a pull-on diaper 10 (see the above-mentioned FIG. 1) is completed, and thus the constitution as explained in the example of the above-mentioned pull-on diaper can be obtained.

It is preferable that the tape-type sheet materials 33T has a width that is approximately similar to or more than the width of the elastic member continuous elements 3S. For example, it is preferable to adjust the width of the tape-type sheet materials 33T to 0.5 mm to 60 mm, and it is preferable to adjust the attachment intervals of the tape-type sheet materials 33T to 1 mm to 40 mm. Further preferably, the width of the tape-type sheet materials 33T is adjusted to 3 mm to 30 mm, and the attachment intervals of the tape-type sheet materials 33T are adjusted to 3 mm to 30 mm. Further preferably, the width of the tape-type sheet materials 33T is adjusted to 5 mm to 10 mm, and the attachment intervals of the tape-type sheet materials 33T are adjusted to 5 mm to 10 mm.

Furthermore, since the lateral direction end portions (the end portions in the direction of length of the diaper) of the tape-type sheet materials 33T are free ends, when the load for stretching of the elastic member continuous elements 3S is released, the tape-type sheet materials 33T contract due to the contraction of the elastic members to form frills (not shown). Therefore, there is an action that cuteness can be created as the entirety of the diaper. Furthermore, the position of the attachment of the tape-type sheet materials 33T to the second sheet material 2S is not limited to the central portion of the tape-type sheet materials 33T in the lateral direction (Y direction), and may be deviated to either of the lateral direction. Namely, in the lateral direction of the tape-type sheet materials 33T, the distance from the position of the attachment to the second sheet material 2S to one edge may be long and the distance to the other edge may be short. By changing the distances from the position of the attachment to the edges in this way, the frills are easily formed at the longer distance. Furthermore, application of the elastic member continuous elements 3S to the tape-type sheet materials 33T by biasing the attachment positions of the elastic member continuous elements 3S against the tape-type sheet materials 33T becomes more easy by using the production method of the present invention that gives high accuracy of the feeding positions of the tape-type sheet materials 33T.

In the production method of the above-mentioned first aspect, the outer cover continuous element 11S for the front portion 21 may be made in the step of preparing the outer cover continuous element 11S for the rear portion 23, and the outer cover continuous element 11S for the rear portion 23 may be made in the step of preparing the outer cover continuous element 11S for the front portion 21.

In the method for producing a pull-on diaper of the above-mentioned first aspect, single layer areas formed of the inner layer material 31 are formed while maintaining similar elasticity to that of a conventional pull-on diaper and retaining the fittability to the body and the movability of the body, by laminating the plural pieces of tape-type sheet materials 33T formed by slitting the first sheet material 1S, with the second sheet material 2S, in the state that the positions in the lateral direction of the tape-type sheet materials 33T during the slitting are respectively maintained. By this, the air-permeability is markedly increased in the single layer area, and thus the pull-on diaper 10 in which the steaminess is significantly reduced can be provided.

Furthermore, since the use amount of the outer layer materials 33 can be decreased, a so-called environment-friendly product can be produced in a disposable-type pull-on diaper. In addition, since the use amount of the outer layer materials 33 can be decreased, the production cost can be reduced. In addition, the softness of the outer cover 11 is improved, and the motion during wearing becomes smooth and the wearing comfort is improved, by having the single layer areas.

In addition, since the tape-type sheet materials 33T for the front side and rear side are laminated and fixed on the second sheet material 2S while they are in the state of being winding on the rolls to thereby maintaining the respective positions in the lateral direction during slitting, the tape-type sheet materials 33T can be disposed on the second sheet material 2S with high precision. It is preferable to suppress the misalignment in the lateral direction of the tape-type sheet materials 33T in a range of the width thereof or less, and for example, in the case where the width of the tape-type sheet material 33T is 3 mm, the misalignment can be suppressed to 2 mm or less in the lateral direction. Although the details will be mentioned below, by doing so, it becomes easy to dispose and adhere the plural pieces of elastic member continuous elements 3S on one piece of tape-type sheet material 33T, and thus it becomes possible to easily change the strength of elasticity by the sites in the direction of length, and a pull-on wear article having excellent fittability can be provided.

Furthermore, since the tape-type sheet materials 33T for the front side and rear side are laminated and fixed on the second sheet materials 2S in the state that the respective positions in the lateral direction during the slitting are maintained, and in the state that the tape-type sheet materials are winding around the upper-side first separation roll 251 and lower-side first separation roll 253, the tension of the tape-type sheet materials 33T can be stabilized. Specifically, since the tape-type sheet materials 33T can be adhered to the second sheet materials 2S in the state that the tape-type sheet materials 33T have constant tension, the entirety of the outer cover of the pull-on diaper 10 is put into an even tension state, and thus the wearability is improved.

In addition, the tape-type sheet materials 33T do not waver in the lateral direction during the conveying, the accuracy of the attachment positions of the tape-type sheet materials 33T on the second sheet material 2S can further be improved.

Furthermore, since the spacing interval of the tape-type sheet materials 33T is the same as the width of the tape-type sheet material 33T, the tape-type sheet materials 33T are laminated and fixed on the second sheet material 2S at equal intervals. By this, when the pull-on diaper 10 is made, the tape-type sheet materials 33T adhered through the elastic member continuous elements 3S are uniformly and evenly disposed on the whole surface of the outer cover 10 of the pants, and thus the pull-on diaper 10 with fine wearability can be provided. Furthermore, by adjusting the attachment intervals of the tape-type sheet materials 33T to equal intervals, an action that the stress applied to the body by the contraction of the elastic member continuous elements 3S (the elastic members 35) is evenly dispersed can be obtained, and an effect that the aesthetic impression in appearance (aesthetic impression provided by regularity) is also enhanced can be obtained.

The feed direction of one of the outer cover continuous elements 11S is transferred in a parallel fashion by the two rolls (the first and fourth rolls 261 and 264) whose roll axes are disposed at a predetermined angle $\theta(0°<\theta<90°)$ with respect to the direction of the arrow A1, and the height of the outer cover continuous element 11S can be adjusted by the two rolls (the second and third rolls 262 and 263) whose roll axes are disposed in parallel with respect to the sheet feed direction (for example, the direction of the arrow A1). By this, the interval of the respective outer cover continuous elements 11S on the front portion 21 and rear portion 23 can be easily adjusted to the predetermined interval D, and furthermore, the surfaces on the side of the second sheet materials 2S of the respective outer cover continuous elements 11S on the front portion 21 and rear portion 23 can be easily positioned on the same height. As a result, when the absorbent body 40 is laminated on the respective outer cover continuous elements 11S on the front portion 21 and rear portion 23, it is not necessary to match the heights of the respective outer cover continuous elements 11S, and thus the step of laminating the absorbent body 40 becomes easy.

Furthermore, depending on the constitution of the production equipment and the space for disposing the production equipment, it is difficult in some cases to feed the respective elastic member continuous elements 3S and the respective second sheet materials 2S for the front side and for the rear side from the same direction to the gaps of the pair of the upper-side first and second separation rolls 251 and 252, and the gaps of the lower-side first and second separation rolls 253 and 254, respectively. In such cases, the feed direction of the elastic member continuous elements 3S may be inverted, or the feed directions of both of the elastic member continuous elements 3S and second sheet materials 2S may be inverted. The production methods in these constitutions will be explained below.

Next, the second aspect of the first embodiment will be explained below, referring to FIG. 24. The second aspect is a method for producing the above-mentioned pull-on diaper 10, which is a production method in which elastic member continuous elements 3S is fed from opposite directions to those in the first aspect.

Figure 24:
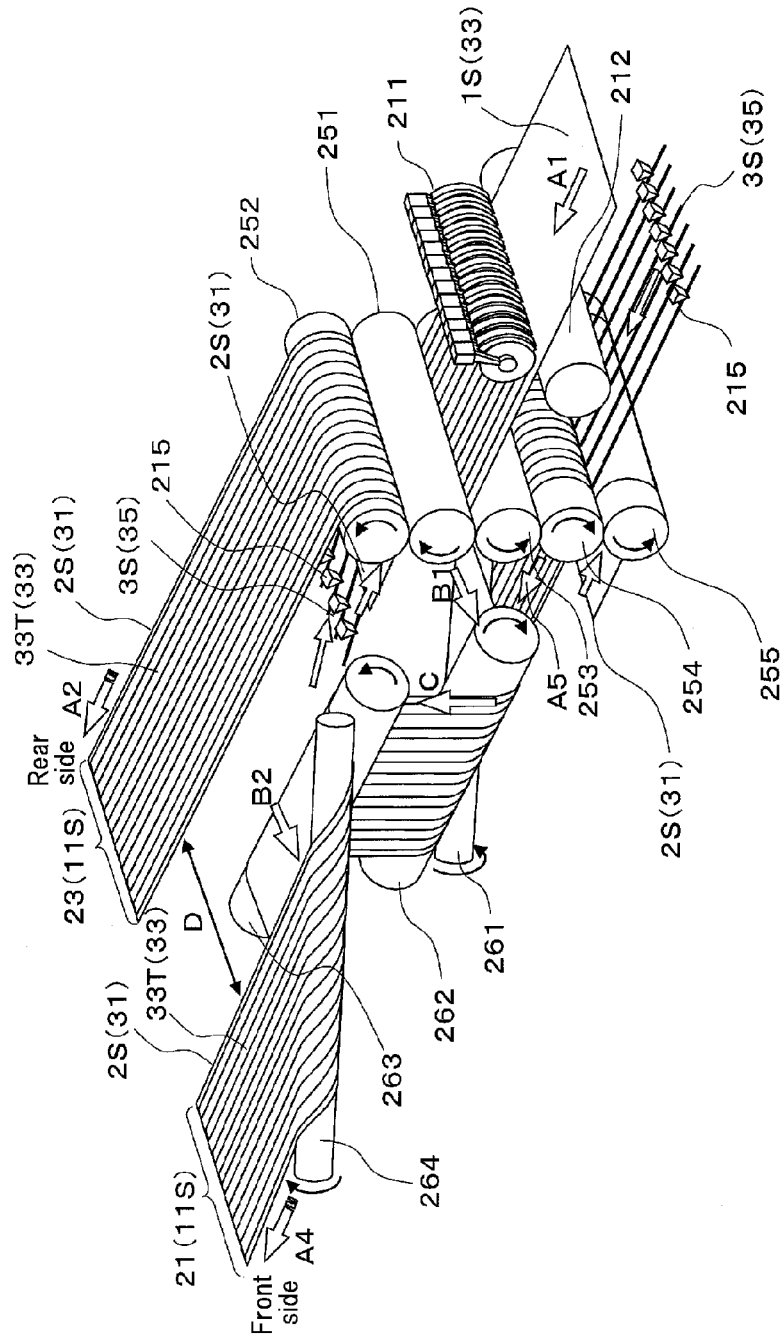
FIG. 24 shows a perspective view of the main portion showing the second aspect of the third embodiment according to the method for producing a pull-on wear article of the present invention.

As shown in FIG. 24, in a similar manner to the above-mentioned first aspect, a first sheet material 1S (outer layer materials 33) is fed in the direction of an arrow A1, plurally slitted in the lateral direction by an outer layer material slit cutter 211, and divided into plural pieces of narrow tape-type sheet materials 33T (the outer layer materials 33). Furthermore, the respective tape-type sheet materials 33T are fed to the gap between an upper-side first separation roll 251 and a lower-side first separation roll 253 in the state that the positions in the lateral direction during the slitting are maintained. Then, and the tape-type sheet materials 33T are wound around the upper-side first separation roll 251 and lower-side first separation roll 253 in an alternate manner, so that the tape-type sheet materials 33T are separated into different two directions (for example, the upper direction and lower direction).

Furthermore, in a similar manner to the above-mentioned first aspect, a second sheet material 2S (an inner layer material 31) is fed, from the direction opposite to the feed direction (the direction of the arrow A1) of the first sheet material 1S, to the gap between the upper-side first separation roll 251 and upper-side second separation roll 252, so that the second sheet material 2S directly winds around the upper-side second separation roll 252. In addition, plural pieces of elastic member continuous elements 3S (elastic members 35) are fed in parallel together with the second sheet material 2S, in the state that the respective elastic member continuous elements 3S are extended, and in the state that an adhesive (not shown) fed by an adhesive coating apparatus 215 is applied thereto.

By this, a pressure is applied between the upper-side first separation roll 251 and upper-side second separation roll 252, and thus an outer cover continuous element 11S that is to be a rear portion 23 that is formed of the second sheet material 2S to which the tape-type sheet materials 33T are adhered through the elastic member continuous elements 3S, is constituted. Furthermore, the both sides of the outer cover continuous element 11S for the rear portion 23 are inverted in the state that the outer cover continuous element 11S is winding around the upper-side second separation roll 252, and the outer cover continuous element 11S is fed in the direction of an arrow A2.

On the other hand, the tape-type sheet materials 33T for the front side wind around the lower-side first separation roll 253 and are separated in the lower direction, and further wind around the lower-side second separation roll 254 and are conveyed. A guide roll 255, which is disposed on the lower portion of the lower-side second separation roll 254, feeds the second sheet material 2S for the front side from the direction opposite to the feed direction of the first sheet material 1S, and the second sheet material 2S directly winds around the guide roll 255 from the lower-side of the guide roll and is fed to the gap between the guide roll 255 and lower side second separation roll 254. Furthermore, in the gap between the guide roll 255 and lower-side second separation roll 254, the plural pieces of elastic member continuous elements 3S, which to be the elastic members 35 for the front side, are fed in parallel onto the second sheet material 2S wound around the guide roll 255, from the same direction to the feed direction (the direction of the arrow A1) of the first sheet material 1S. The respective elastic member continuous elements 3S are fed in the state that the respective elements are extended and in the state that an adhesive (not shown) fed from the adhesive coating apparatus 215 is applied thereto, and the tape-type sheet materials 33T conveyed while winding around the lower-side second separation roll 254 and the second sheet material 2S are adhered through these elastic member continuous elements 3S. The above-mentioned guide roll 255 is preferably a rotatable roll that is rotated by a similar rotation driving means (not shown) to that mentioned above. In this case, it is preferable that the circumferential velocity of the guide roll 255 corresponds to the circumferential velocity of the lower-side second separation roll 254. Furthermore, it is preferable that the guide roll 255 has a surface with a large friction force such as a roughened surface or rubber on the circumferential surface of the roll so that the sheet would not slip on the circumferential surface of the roll.

By this, a pressure is applied between the lower-side second separation roll 254 and the guide roll 255, and the tape-type sheet materials 33T are adhered onto the second sheet material 2S through the elastic member continuous elements 3S by the adhesive applied to the elastic member continuous elements 3S. At this time, the tape-type sheet materials 33T are conveyed by winding around the rolling surfaces of the lower-side first separation roll 253 and lower-side second separation roll 254 without slipping, and thus are adhered to the second sheet material 2S in the state that the positions in the lateral direction during the slitting are maintained. Furthermore, the tape-type sheet materials 33T are adhered to the second sheet material 2S without getting away from the respective roll surfaces of the lower-side first separation roll 253 and lower-side second separation roll 254. As a result, an outer cover continuous element 11S that is to be the rear portion 21 made of the second sheet material 2S to which the tape-type sheet materials 33T are adhered through the elastic member continuous elements 3S is constituted. Furthermore, the outer cover continuous element 11S for the front portion 21 is fed in the direction of an arrow A5 from the gap between the lower-side second separation roll 254 and guide roll 255.

As explained above, in order for the tape-type sheet materials 33T to be adhered to the second sheet material 2S through the elastic member continuous elements 3S to which the adhesive is applied, it is necessary that the second sheet material 2S, elastic member continuous elements 3S and tape-type sheet materials 33T are laminated from the same direction in this order, and fed to the gap between the lower-side second separation rolls 254 and the guide roll 255. By feeding in such way, attachment of the adhesive applied to the elastic member continuous elements 3S to the roll surfaces can be prevented.

Next, the positions of the respective outer cover continuous elements 11S on the front portion 21 and rear portion 23 are adjusted to give a predetermined interval D. In this step of adjusting the positions, the feed direction of the outer cover continuous element 11S for the front portion 21 is adjusted to the direction (the direction of the arrow A4) that is in parallel to the feed direction (the direction of the arrow A2) of the outer cover continuous element 11S for the rear portion 23, and the surface on the side of the second sheet material 2S of the outer cover continuous element 11S for the front portion 21 and the surface on the side of the second sheet material 2S of the outer cover continuous element 11S for the rear portion 23 are adjusted to be in the same planar direction (for example, the upper surface) and at the same height.

First, the both surfaces of the outer cover continuous element 11S for the front portion 21 are inverted by a first roll 261 whose roll axis is disposed at a predetermined angle (for example, 30° to 60°, preferably 45°) with respect to the feed direction (the direction of an arrow A5) of the outer cover continuous element 11S for the front portion 21, and the feed direction is changed to the direction of an arrow B1. Subsequently, the feed direction of the outer cover continuous element 11S for the front portion 21 is changed from the horizontal direction to the vertical direction (the direction of an arrow C) by a second roll 262. Subsequently, the feed direction of the outer cover continuous element 11S for the front portion 21 is changed from the vertical direction to the horizontal direction (the direction of an arrow B2) by a third roll 263. Next, the both surfaces of the outer cover continuous element 11S for the front portion 21 are inverted by a fourth roll 264 whose roll axis is disposed at a predetermined angle (for example, 30° to 60°, preferably 45°) with respect to the feed direction of the outer cover continuous element 11S for the front portion 21 to thereby direct the surface on the side of the second sheet material 2S of the outer cover continuous element 11S for the front portion 21 and the surface on the side of the second sheet material 2S of the outer cover continuous element 11S for the rear portion 23 toward the same planar direction (the upper surface) and positioned at the same height, and the feed direction becomes the feed direction (the direction of an arrow A4) that is in parallel to the outer cover continuous element 11S for the rear portion 23.

Therefore, by the first and third rolls 261 and 263, the surfaces on the side of the second sheet material 2S of the respective outer cover continuous elements 11S on the front portion 21 and rear portion 23 are adjusted to be at the same height, by adjusting the interval of the respective outer cover continuous elements 11S on the front portion 21 and rear portion 23 to a predetermined interval D, and adjusting the interval of the second and fourth roll 262 and 264 with consideration for the roll diameters of the first and third rolls 261 and 263.

Subsequently, the production steps are similar to those in the production method as explained in the above-mentioned first aspect.

Next, the third aspect of the first aspect will be explained below, referring to FIG. 25. The third aspect is a method for producing the above-mentioned pull-on diaper 10, which is a production method in which elastic member continuous elements 3S and second sheet material 2S are fed from opposite directions to those in the first aspect.

Figure 25:
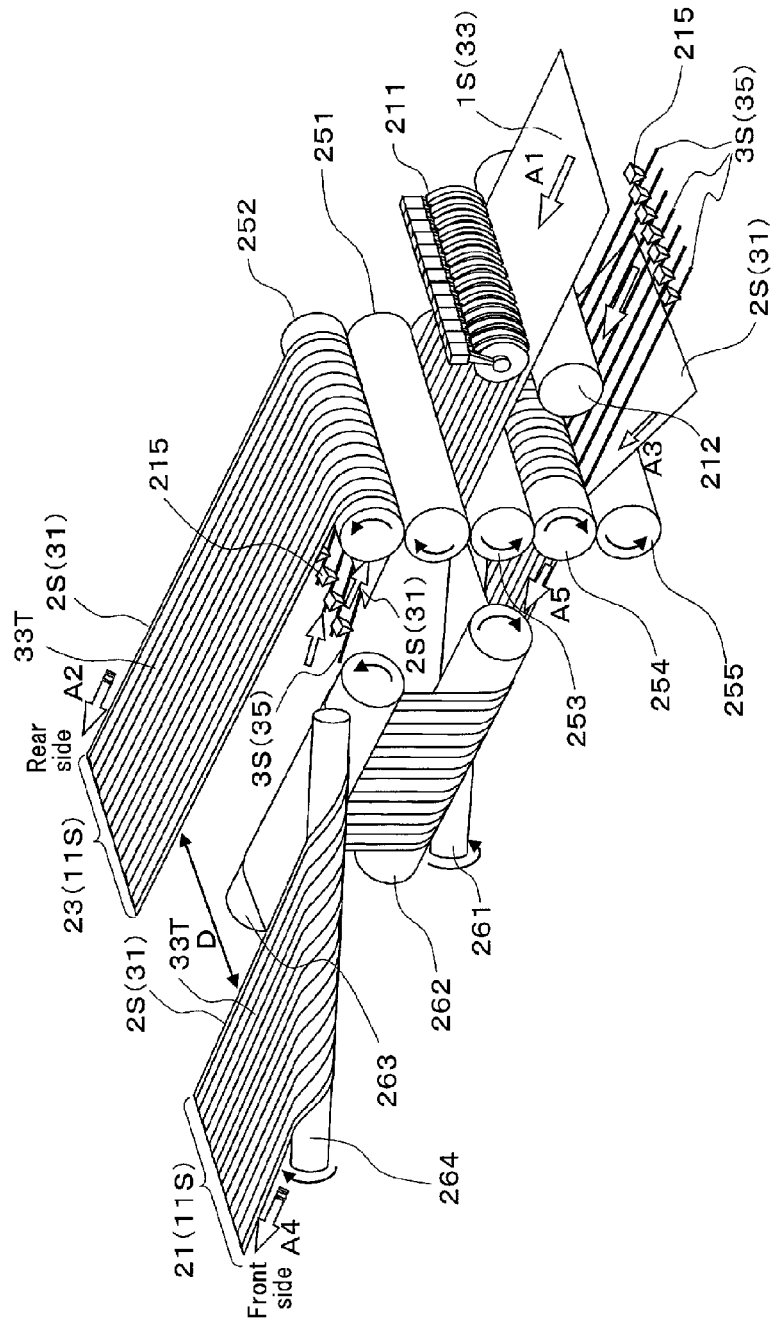
FIG. 25 shows a perspective view of the main portion showing the third aspect of the third embodiment according to the method for producing a pull-on wear article of the present invention.

As shown in FIG. 25, an outer cover continuous element 11S to be disposed on a rear portion 23 is constituted in a similar manner to the above-mentioned first aspect, the both surfaces are inverted in the state that the outer cover continuous element 11S is winding around an upper-side second separation roll 252, and the outer cover continuous element 11S is fed in the direction of an arrow A2.

On the other hand, the tape-type sheet materials 33T for the front side wind around the lower-side first separation roll 253 and are separated in the lower direction, and further wind around the lower-side second separation roll 254 and are conveyed. A guide roll 255 is disposed on the lower portion of the lower-side second separation roll 254, and the second sheet material 2S for the front side is fed from the direction of the arrow A3 that is similar to the feed direction of the first sheet material 1S and sent to the gap between the lower-side second separation roll 254 and guide roll 255. Furthermore, in the gap between the guide roll 255 and lower-side second separation roll 254, the plural pieces of elastic member continuous elements 3S that are to be the elastic members 35 for the front side are fed in parallel onto the second sheet material 2S from the same direction to the feed direction (the direction of the arrow A1) of the first sheet material 1S. The respective elastic member continuous elements 3S are fed in the state that the respective elements are extended and in the state that an adhesive (not shown) fed from the adhesive coating apparatus 215 is applied thereto, and the tape-type sheet materials 33T conveyed while winding around the lower-side second separation roll 254 is adhered through these elastic member continuous elements 3S.

By this, a pressure is applied between the lower side second separation roll 254 and the guide roll 255, and the tape-type sheet materials 33T are adhered onto the second sheet material 2S through the elastic member continuous elements 3S by the adhesive applied to the elastic member continuous elements 3S. At this time, the tape-type sheet materials 33T are conveyed by winding around the rolling surfaces of the lower-side first separation roll 253 without slipping, and thus are adhered to the second sheet material 2S in the state that the positions in the lateral direction during the slitting are maintained. Furthermore, the tape-type sheet materials 33T are adhered to the second sheet material 2S without getting away from the respective roll surfaces of the lower-side first separation roll 253 and lower-side second separation roll 254. As a result, an outer cover continuous element 11S that is to be the rear portion 21 made of the second sheet material 2S to which the tape-type sheet materials 33T are adhered through the elastic member continuous elements 3S is constituted. Furthermore, the outer cover continuous element 11S for the front portion 21 is fed in the direction of an arrow A5 from the gap between the lower-side second separation roll 254 and guide roll 255.

Next, the positions of the respective outer cover continuous elements 11S on the front portion 21 and rear portion 23 are adjusted to give a predetermined interval D. This method for the adjusting the positions of is similar to that of the above-mentioned second aspect. As a result thereof, the surface on the side of the second sheet material 2S of the outer cover continuous element 11S for the front portion 21 and the surface on the side of the second sheet material 2S of the outer cover continuous element 11S for the rear portion 23 are directed toward the same planar direction (the upper surface) and positioned at the same height, and the feed direction becomes the feed direction (the direction of an arrow A4) that is in parallel to the outer cover continuous element 11S for the rear portion 23 is obtained.

Subsequent production steps are similar to those in the production method as explained in the above-mentioned first aspect.

Similar action and effect to those in the above-mentioned first aspect can also be obtained in the second and third aspects. Further, in order for the tape-type sheet materials 33T to be adhered to the second sheet material 2S through the elastic member continuous elements 3S to which the adhesive is applied, it is necessary that the second sheet material 2S, elastic member continuous elements 3S and tape-type sheet materials 33T are laminated from the same direction in this order, and fed to the gap between the lower side second separation rolls 254 and the guide roll 255. By feeding in such way, attachment of the adhesive applied to the elastic member continuous elements 3S to the roll surfaces can be prevented.

Next, the second embodiment of the production method of the present invention will be explained below, referring to FIG. 26. The second embodiment is a preferable example of a method for producing a pull-on diaper in which elastic member continuous elements 3S are not used in the above-mentioned pull-on diaper 10.

Figure 26:
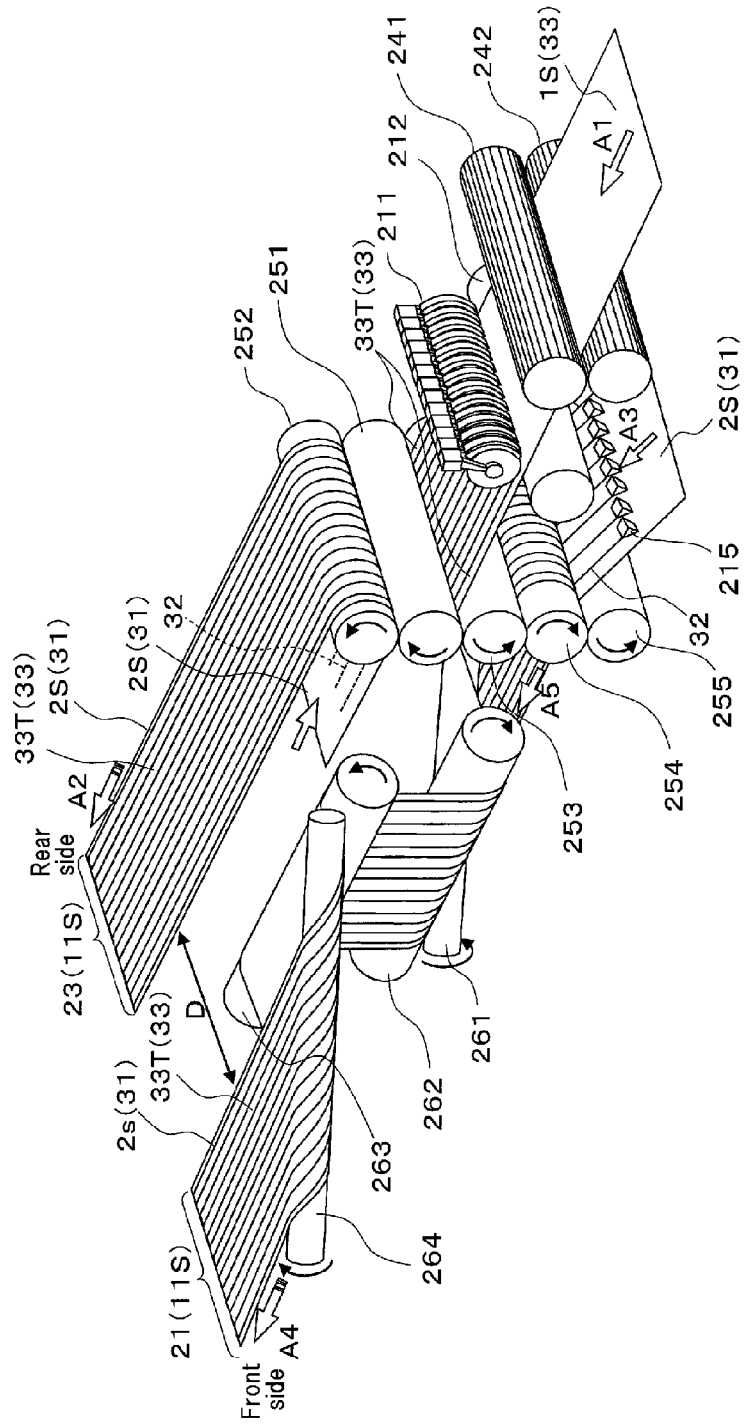
FIG. 26 shows a perspective view of the main portion showing the fourth embodiment according to the method for producing a pull-on wear article of the present invention.

As shown in FIG. 26, a first sheet material 1S having elasticity (outer layer materials 33) is fed in the direction of an arrow A1 in a similar manner to that in the first aspect of the first embodiment.

As the first sheet material 1S (the outer layer materials 33) having elasticity, elastic sheets such as nonwoven fabrics comprising elastic fibers and elastic films or the like can be used. In the case where texture and fabric-like appearance are emphasized, it is preferable that these stretchable sheets have a fiber layer on the surface. In the case where this fiber layer is inelastic, the fiber layer becomes extensible by a stretching processing or the like so that the inelastic fiber layer will not inhibit the elasticity of the elastic sheet. As the stretching processing, for example, a tooth-groove processing in which the bonding between the fibers are cut or the fibers are elongated in the fiber layer is exemplified, and by this way, elasticity is exhibited without inhibiting the elasticity of the elastic sheet having the fiber layer.

The whole area of the surface of the first sheet material 1S is subjected to the tooth-groove processing as a stretching processing by a concavo-convex roll 241 having a roll surface on which concavo-convex is formed. Furthermore, a concavo-convex roll 242 that engages with the concavo-convex roll 241 is disposed on the position corresponding to the concavo-convex roll 241. As a result, grooves (illustration is omitted) are imparted to the first sheet material 1S in the lateral direction. By this tooth-groove processing, extensibility is imparted to the fiber layer in the first sheet material 1S in the longitudinal direction thereof, without inhibiting the elasticity of the elastic sheet, to thereby allow the first sheet material 1S to exhibit elasticity. These intervals of the grooves depends on the thickness of the nonwoven fabric of the first sheet material 1S, and, for example, are formed into equal intervals. In addition, in the case where the degree of imparting of elasticity is changed in every position, it is also possible to change the intervals of the grooves. For example, in the case where the thickness of the first sheet material 1S is 0.01 mm to 0.2 mm, at an area where strong elasticity is desired, the intervals of the grooves are adjusted to about 2 mm to 5 mm, and at an area where weak elasticity is desired, the intervals of the grooves are adjusted to about 0.5 mm to 2 mm. The intervals of the grooves are also changed depending on the thickness of the first sheet material 1S.

The elasticity that the first sheet material 1S as used herein refers to, for example, elasticity that can substitute for the elasticity imparted by the above-mentioned elastic member continuous elements 3S. The method for processing the first sheet material 1S is not limited as long as the outer layer materials have desired elasticity by the grooves.

As the above-mentioned first sheet material 1S having elasticity, for example, (1) a sheet comprising an elastic fiber layer and an extensible fiber layer(s) that is/are integrated with one or both surface(s) of the elastic fiber layer, (2) a sheet comprising a net-like elastic sheet and an extensible fiber layer(s) that is/are integrated with one or both surface(s) of the elastic sheet, (3) a sheet comprising an elastic sheet made of an elastic film and an extensible fiber layer(s) that is/are integrated with one or both surface(s) of the elastic sheet, (4) a elastic sheet in which many elastic filaments disposed to be extensible in one direction without intersecting with each other are bonded to an extensible nonwoven fabric, substantially in a inextensible state, over the full lengths thereof.

As the sheet of the above-mentioned (1), for example, (a) an elastic nonwoven fabric in which a substantially inelastic fiber layer is disposed on at least one surface of an elastic fiber layer, wherein the both fiber layers are bonded on the whole surface by heat-fusion bonding of the intersection points of the fibers in the state that the constitutional fibers in the elastic fiber layer retain the shapes of the fibers, and the nonwoven fabric is in either of the state in which a part of the constitutional fibers in the inelastic fiber layer has penetrated into the elastic fiber layer, and the state in which a part of the constitutional fibers in the elastic fiber layer has penetrated into the non-elastic fiber layer, or in both states, can be exemplified. Furthermore, as the sheets of the above-mentioned (1) to (3), (b) a elastic sheet having an elastic layer with elastic stretchability and a substantially inelastic fiber layer, wherein the two layers are made into a laminated sheet by laminating in their thickness direction and bonding partially and a stretching is performed to the laminated sheet, and the like can be preferably used. As a means for these stretching and for obtaining the extensible fiber layers and nonwoven fabrics of the above-mentioned (1) to (3), it is preferable to conduct the above-mentioned tooth-groove processing.

As the elastic nonwoven fabric of the above-mentioned (a), in the interface of the elastic fiber layer and inelastic fiber layer and in the vicinity thereof, the intersection points of the constitutional fibers of the elastic fiber layer and the constitutional fibers of the non-elastic fiber layer are bonded by heat-fusion, and thus are evenly bonded on substantially the whole surface. Since the two layers are bonded on the whole surface, formation of spaces by the separation of the two layers is prevented, and an elastic nonwoven fabric having a multilayer structure that gives feeling of unity like a nonwoven fabric of a single layer is formed. The above-mentioned state that the constitutional fibers of the elastic fiber layer retains the fiber forms refers to a state that most of the constitutional fibers in the elastic fiber layer are not deformed into a film shape, or a film structure comprising fibers, even in the case where heat, pressure or the like is applied. Furthermore, in the elastic fiber layer, the intersection points of the constitutional fibers are bonded by heat-fusion in the layer. Similarly, also in the inelastic fiber layer, the intersection points of the constitutional fibers are heat-fusion bonded in the layer.

In the case where the inelastic fiber layers are disposed on the both surfaces of the elastic fiber layer, at least either one surface is in either of the state in which a part of the constitutional fibers thereof has penetrated into the elastic fiber layer, and the state in which a part of the constitutional fibers in the elastic fiber layer has penetrated into at least one of the non-elastic fiber layers, or in both states.

The elastic fiber layer has a property that it can be stretched, and has a property to contract when it is released from load for stretching. Furthermore, it is an aggregate of fibers having elasticity. Moreover, the elastic fiber layer may be in the form of a web or nonwoven fabric formed of fibers having elasticity. For example, it may be a nonwoven fabric formed by a spinning blown process, a spunbond process, a meltblown process or the like. Specifically, a web obtained by a spinning blown process is preferable. As the constitutional fibers for the elastic fiber layer, for example, fibers obtained from raw materials such as thermoplastic elastomers and rubbers can be used. Specifically, fibers obtained from thermoplastic elastomers as raw materials are preferable for the elastic non-woven fabric in the embodiment comprising an air-through nonwoven fabric as a basic constitution, since melt spinning using an extruder as same as in general thermoplastic resins is possible, and fibers obtained by such way are easily heat-fusion bonded. Examples of the thermoplastic elastomers may include styrene-based elastomers such as SBS, SIS, SEBS and SEPS, olefin-based elastomers, polyester-based elastomers, and polyurethane-based elastomers. These can be used by one kind alone or by a combination of two or more kinds.

The inelastic fiber layer has extensibility, but is substantially inelastic. The extensibility as used herein may be either of the case where the constitutional fibers themselves elongate, and the case where the constitutional fibers themselves do not elongate, but the entirety of the fiber layer elongates due to a separation of the fibers that are heat-fusion bonded at the intersection points of the fibers, a structure change in the three-dimensional structure formed of plural pieces of fibers by the heat-fusion bonding of the fibers and the like, or a tear of constitutional fibers. Examples of the fibers that constitute the inelastic fiber layer may include fibers formed of polyethylene (PE), polypropylene (PP), polyesters (PET and PBT), polyamides and the like, and the like. The fibers that constitute the inelastic fiber layer may be either short fibers or long fibers, and may be either hydrophilic or water-repellent. Furthermore, core-sheath type or side-by-side conjugate fibers, splittable fibers, modified cross-sectional surface fibers, crimped fibers, heat-shrinkable fibers and the like can also be used. These fibers can be used by one kind alone or by a combination of two or more kinds. The inelastic fiber layer may be a web or nonwoven fabric of continuous filaments or short fibers.

The elastic sheet of the above-mentioned (b) is obtained by conducting a stretching processing on a laminate sheet comprising an elastic layer having elastic stretchability and substantially inelastic fiber layer(s) that is/are laminated on one or both surface(s) of the elastic layer, wherein the inelastic fiber layer(s) is/are partially bonded in a regulated pattern.

Next, the first sheet material 1S that has undergone the above-mentioned tooth-groove processing is plurally slit in the lateral direction by an outer layer material slit cutter 211 and divided into plural pieces to produce narrow tape-type sheet materials 33T (outer layer materials 33). For example, the respective tape-type sheet materials 33T are slitted into even widths.

Furthermore, the respective tape-type sheet materials 33T are fed to the gap between an upper-side first separation roll 251 and a lower-side first separation roll 253 in the state that the positions in the lateral direction during the slitting are maintained in a similar manner to the above-mentioned first aspect. The plural tape-type sheet materials 33T fed to the gap of the rolls are wound around the upper-side first separation roll 251 and lower-side first separation roll 253 in an alternate manner to separate the tape-type sheet materials 33T into different two directions for the front side and for the rear side.

When the tape-type sheet materials 33T for the rear side, which have wound around the upper-side first separation roll 251 and have been separated in the upper direction, wind around an upper-side second separation roll 252, the second sheet material 2S is fed from the direction opposite to the feeding direction of the first sheet material 1S (the direction of an arrow A1) so as to directly wind around the upper-side second separation roll 252, to the gap between the upper-side first separation roll 251 and upper-side second separation roll 252. At this time, the adhesive 32 is applied in advance by an adhesive coating apparatus 215 to the positions to which the tape-type sheet materials 33T are to be adhered.

Furthermore, a pressure is applied between the upper-side first separation roll 251 and upper-side second separation roll 252, and the tape-type sheet materials 33T are adhered by an adhesive 32 applied onto the lower surface side of the second sheet material 2S by an adhesive application apparatus (illustration is omitted). At this time, the tape-type sheet materials 33T are adhered to the second sheet material 2S in the state that the positions in the lateral direction during the slitting are maintained. Further, the tape-type sheet materials 33T are adhered to the second sheet material 2S without getting away from the upper-side first separation roll 251. Thus, an outer cover continuous element 11S that is to be the rear portion 23 made of the second sheet material 2S to which the tape-type sheet materials 33T are adhered is constituted. Furthermore, the both sides of the outer cover continuous element 11S for the rear portion 23 are inverted in the state that the outer cover continuous element 11S is winding around the upper-side second separation roll 252, and the outer cover continuous element 11S is fed in the direction of an arrow A2.

On the other hand, the tape-type sheet materials 33T for the front side wind around the lower-side first separation roll 253 and are separated in the lower direction, and further wind around the lower-side second separation roll 254 and are conveyed. A guide roll 255, which is disposed on the lower portion of the lower-side second separation roll 254, feeds the second sheet material 2S (the inner layer material 31) for the front side from the direction of the arrow A3 that is the same feed direction to that of the first sheet material 1S. At this time, the adhesive 32 is applied in advance by an adhesive coating apparatus 215 to the positions to which the tape-type sheet materials 33T are to be attached of the second sheet material 2S.

Further, a pressure is applied between the lower-side second separation roll 254 and the guide roll 255, and the tape-type sheet materials 33T are adhered onto the second sheet material 2S by the adhesive 32. At this time, the tape-type sheet materials 33T are conveyed by winding around the rolling surfaces of the lower-side first separation roll 253 and lower-side second separation roll 254 without slipping, and thus are attached to the second sheet material 2S in the state that the positions in the lateral direction during the slitting are maintained. Furthermore, the tape-type sheet materials 33T are adhered to the second sheet material 2S while maintaining approximately constant tension without getting away from the respective roll surfaces of the lower-side first separation roll 253 and lower-side second separation roll 254. As a result, an outer cover continuous element 11S that is to be the rear portion 21 made of the second sheet material 2S to which the tape-type sheet materials 33T are adhered is constituted. Furthermore, the outer cover continuous element 11S for the front portion 21 is fed in the direction of an arrow A5 from the gap between the lower-side second separation roll 254 and guide roll 255.

The adhesive 32 fed to the respective second sheet materials 2S is fed to a predetermined position (for example, approximately the central portion or one side of the lateral direction) on which each tape-type sheet material 33T is adhered, and the method for the feeding may be continuous or intermittent. As the adhesive 32, for example, a hot-melt adhesive, a double-faced adhesive tape and the like are used.

As explained above, in order for the tape-type sheet materials 33T to be adhered to the second sheet material 2S to which the adhesive 32 is applied, it is necessary that the second sheet material 2S and tape-type sheet materials 33T are laminated from the same direction, and fed to the gap between the upper-side first and second separation rolls 251 and 252 and the gap between the lower-second separation rolls and the guide roll 254 and 255. By feeding in such way, attachment of the adhesive 32 applied to the second sheet material 2S to the roll surfaces can be prevented.

Next, the positions of the respective outer cover continuous elements 11S on the front portion 21 and rear portion 23 are adjusted to give a predetermined interval D in a similar manner to the second aspect of the above-mentioned first embodiment. In this step of adjusting the positions, the feed direction of the outer cover continuous element 11S for the front portion 21 is adjusted to the parallel direction of an arrow A4 that is in parallel to the feed direction (the direction of the arrow A2) of the outer cover continuous element 11S for the rear portion 23, and the surface on the side of the second sheet material 2S of the outer cover continuous element 11S for the front portion 21 and the surface on the side of the second sheet material 2S of the outer cover continuous element 11S for the rear portion 23 are adjusted to be in the same planar direction (for example, the upper surface) and at the same height. Subsequently, the production steps are similar to those in the production method as explained in the above-mentioned first embodiment.

In this second embodiment of the production method of the present invention, similar effects to those in the above-mentioned first embodiment can be obtained. Furthermore, since elasticity is imparted to the tape-type sheet materials 33T themselves, it is not necessary to dispose elastic members between the first sheet material 1S (the outer layer materials 33) and the second sheet material 2S (the inner layer material 31), and this enables reduction of the materials and reduction of the material costs.

Further, since the first sheet material 1S are subjected to a stretching processing so as to have concave and convex, soft appearance and touch are provided, and frills can also be formed on the tape-type sheet materials 33T by narrowing the application width of the adhesive 32 than the width of the tape-type sheet materials 33T.

Furthermore, by changing the widths of the tape-type sheet materials 33T, the elastic force is also changed and adjusted to a suitable constriction pressure corresponding to each site such as waist portion, portion on ilium and lumbar. For example, by increasing width more on the waist portion and the portion on ilium than those on the other sites, the elastic force can be enhanced and the constriction pressure can be increased.

Furthermore, in the pull-on diaper 10 on which the elastic members are not disposed, in the case where the elasticity of the laminated areas is weak, the elastic member continuous elements 3S in the first embodiment may be interposed between the first sheet material 1S and second sheet material 2S as necessary.

Next, the first aspect of the third embodiment of the production method according to the present invention will be explained below, referring to FIG. 27 and FIG. 28. The first aspect of the third embodiment is a method for producing a pull-on diaper having a constitution in which tape-type sheet materials 33T having different widths are partially used in the above-mentioned pull-on diaper 10.

Figure 27:
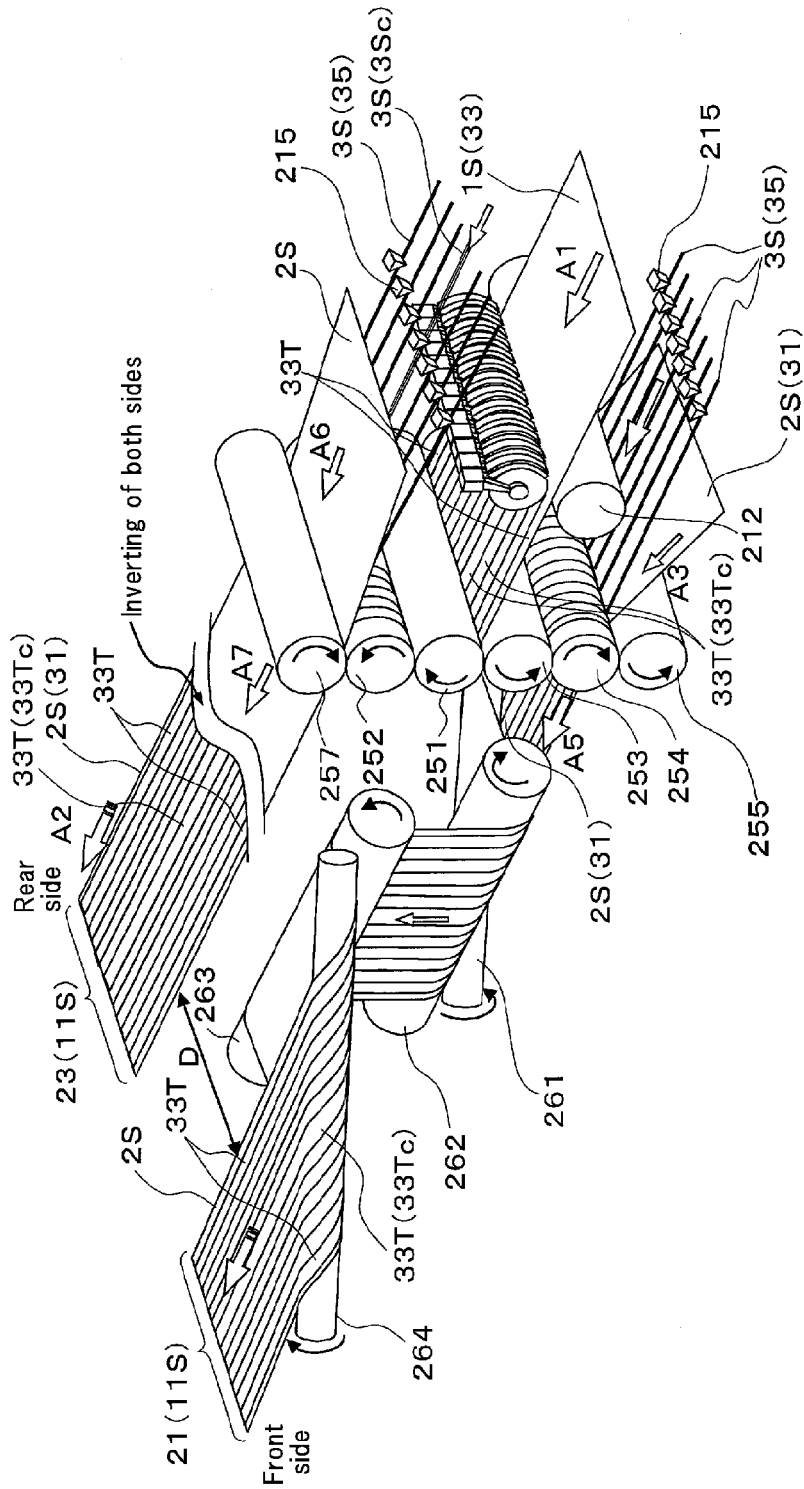
FIG. 27 shows a perspective view of the main portion showing the first aspect of the fifth embodiment according to the method for producing a pull-on wear article of the present invention.
Figure 28:
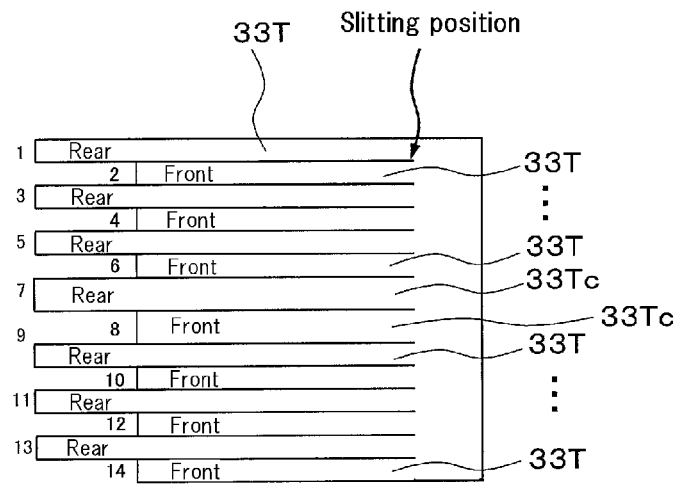
FIG. 28 shows a plane view showing the slit state of the tape-type sheet materials of the first aspect of the fifth embodiment.

As shown in FIG. 27 and FIG. 28, in a similar manner to the above-mentioned first embodiment, a first sheet material 1S (outer layer materials 33) is fed in the direction of an arrow A1 and is slitted in the feed direction by using outer layer material slit cutter 211 to give narrow tape-type sheet materials 33T (the outer layer materials 33). At this time, for example, the tape-type sheet materials 33T (33Tc) to be disposed on the ilium bones are made wide, and the other tape-type sheet materials 33T are made so as to have equal widths. For example, the tape-type sheet materials 33Tc are formed to be about 1.05 times to 3 times, preferably about 1.1 times to 2 times wider than the other tape-type sheet materials 33T. Furthermore, the respective tape-type sheet materials 33T are fed to the gap between an upper-side first separation roll 251 and a lower-side first separation roll 253 in the state that the positions in the lateral direction during the slitting are maintained.

The plural pieces of tape-type sheet materials 33T are wound around the upper-side first separation roll 251 and lower-side first separation roll 253 in an alternate manner to thereby be separated into different two directions (for example, the upper direction and lower direction). Specifically, the plural pieces of tape-type sheet materials 33T are separated into the tape-type sheet materials for the front side and for the rear side.

The tape-type sheet materials 33T for the rear side wind around the upper-side first separation roll 251 and are separated in the upper direction, and further wind around the upper-side second separation roll 252 and are conveyed in the upper direction. On the other hand, a pressing roll 257 is disposed on the upper portion of the upper-side second separation roll 252. The second sheet material 2S for the rear side from the similar direction (the direction of an arrow A6) is fed to the feed direction of the first sheet material 1S (the direction of the arrow A1) and is sent to the gap between the upper-side second separation roll 252 and pressing roll 257. Furthermore, in the gap between the pressing roll 257 and upper-side second separation roll 252, elastic member continuous elements 3S (elastic members 35) for the front side to which an adhesive (not shown) is applied in advance by an adhesive coating apparatus 215 are fed to the lower side of the second sheet material 2S from the direction that is similar to the feed direction of the first sheet material 1S (the direction of the arrow A1), and the tape-type sheet materials 33T conveyed while winding around the upper-side second separation roll 252 are laminated and adhered through the elastic member continuous elements 3S.

Therefore, a pressure is applied between the upper-side second separation roll 252 and pressing roll 257, and the tape-type sheet materials 33T are adhered onto the second sheet material 2S through the elastic member continuous elements 3S by the adhesive applied to the elastic member continuous elements 3S. At this time, the tape-type sheet materials 33T are adhered to the second sheet material 2S in the state that the positions in the lateral direction during the slitting are maintained. Furthermore, the tape-type sheet materials 33T are adhered to the second sheet material 2S without getting away from the respective roll surfaces of the upper-side first separation roll 251 and upper-side second separation roll 252. Each elastic member continuous element 3S for the rear side is fed, for example, so as to be disposed on the center of the lateral direction of each tape-type sheet material 33T for the rear side.

Furthermore, the plural pieces (for example, three pieces in the illustration) of the elastic member continuous elements 3S (3Sc) to be disposed on the ilium bones are fed without running over the width of the tape-type sheet material 33T (33Tc) since the tape-type sheet material 33Tc is formed to be wide at the position.

By this, the outer cover continuous element 11S that is to be the rear portion 23, which is formed of the second sheet material 2S to which the tape-type sheet materials 33T are adhered through the elastic member continuous elements 3S, is constituted. Furthermore, the outer cover continuous element 11S for the rear portion 23 is fed in the direction of an arrow A7 in the state that the tape-type sheet materials 33T are on the lower side.

Furthermore, the both sides of the outer cover continuous element 11S for the rear side are inverted, and the outer cover continuous element 11S is fed in the direction of an arrow A2. For inverting the both surfaces, although not illustrated, as an example, a horizontal roll is disposed on the upper surface side (the side of the second sheet material 2S) of the outer cover continuous element 11S, the outer cover continuous element 11S is turned by 90° around the feed direction as an axis, and the side of the second sheet material 2S surface of the outer cover continuous element 11S that has turned is received once by a vertical roll. Furthermore, the outer cover continuous element 11S is turned by 90° around the feed direction as an axis, and the side of the upper surface of the outer cover continuous element 11S that has turned is received by another horizontal roll. By this, the both surfaces of the outer cover continuous element 11S can be stably inverted around the feed direction as an axis without wavering in the lateral direction and height direction. As a result, in the outer cover continuous element 11S for the rear portion 23, the sites where plural pieces of the elastic member continuous elements 3Sc are adhered to one piece of the tape-type sheet material 33T are disposed on the height of the ilium bones in the pull-on diaper continuous body in the subsequent steps.

On the other hand, for the front side, in a similar manner to the third aspect of the above-mentioned first embodiment, a pressure is applied between the lower side second separation roll 254 and guide roll 255, and the tape-type sheet materials 33T are adhered onto the second sheet material 2S through the elastic member continuous elements 3S by the adhesive applied to the elastic member continuous elements 3S. At this time, the tape-type sheet materials 33T are adhered to the second sheet material 2S in the state that the positions in the lateral direction during the slitting are maintained. By this, the outer cover continuous element 11S that is to be the front portion 21, which is formed of the second sheet material 2S to which the tape-type sheet materials 33T are adhered through the elastic member continuous elements 3S, is constituted. Furthermore, the outer cover continuous element 11S for the front portion 21 is fed in the direction of an arrow A5. As a result, in the outer cover continuous element 11S for the front portion 21, the sites where the plural pieces of elastic member continuous elements 3Sc are adhered to one piece of tape-type sheet material 33T are disposed on the height of the ilium bones in the pull-on diaper continuous body in the subsequent steps.

Next, the positions of the respective outer cover continuous elements 11S on the front portion 21 and rear portion 23 are adjusted to give a predetermined interval D in a similar manner to the second aspect of the above-mentioned first embodiment. In this position-adjusting step, the feed direction of the outer cover continuous element 11S for the front portion 21 is adjusted to the direction of the arrow A4 that is in parallel to the feed direction (the direction of the arrow A2) of the outer cover continuous element 11S for the rear portion 23, and the surface of the side of the second sheet material 2S of the outer cover continuous element 11S for the front portion 21 and the surface of the side of the second sheet material 2S of the outer cover continuous element 11S for the rear portion 23 are disposed in the same planar direction (for example, the upper surface) and at the same height.

By the above-mentioned steps, the outer cover continuous element 11S for the front portion 21 and the outer cover continuous element 11S for the rear portion 23, on which the wide tape-type sheet materials 33Tc are disposed on outer side, can be obtained.

The subsequent steps are similar to the steps as explained in the above-mentioned first embodiment.

In the production method of the first aspect of the above-mentioned third embodiment, similar action and effect to those of the above-mentioned first embodiment can be obtained. Furthermore, since plural pieces of the elastic member continuous element 3Sc can be adhered to one piece of the tape-type sheet material 33Tc by widely making the tape-type sheet material 33Tc to be disposed on the ilium bones, an advantage that the elastic force can be strengthen and the constriction force on the ilium bones is strengthen, and thus the pull-on diaper becomes difficult to fall off during motion and the like, can be obtained.

Next, the second aspect of the third aspect will be explained, referring to FIG. 29. When the tape-type sheet materials 33Tc to be widely made each on the front portion 21 and rear portion 23 are continuously taken on the first sheet material 1S, the interval with the other tape-type sheet materials 33T are opened at interval equivalent to the width of a wide tape-type sheet material 33Tc on one side of the lateral direction of one wide tape-type sheet material 33Tc on the outer cover continuous element 11S. Therefore, in the second aspect, a production method comprising making the intervals with the adjacent tape-type sheet materials 33T on the both sides of the wide tape-type sheet material 33Tc to be equivalent to the intervals between the other tape-type sheet materials 33T will be explained below, referring to FIG. 29.

Figure 29:
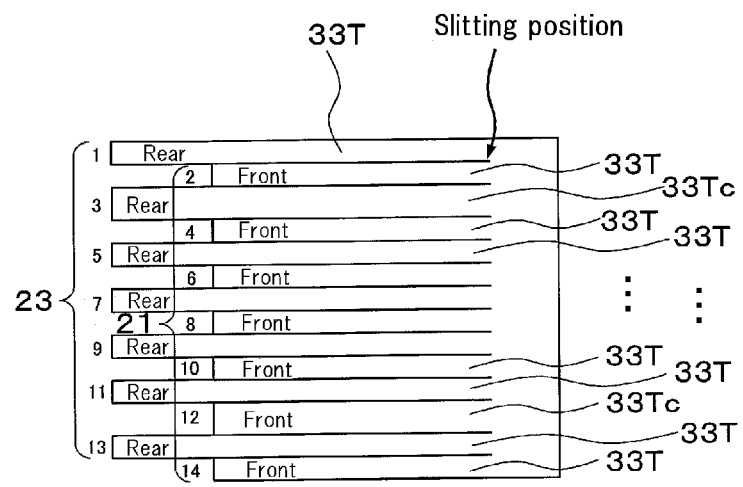
FIG. 29 shows a plane view showing the slit state of the tape-type sheet materials of the second aspect of the fifth embodiment.

As shown in FIG. 29, in the first sheet material 1S, the wide tape-type sheet materials 33Tc on the front portion 21 are taken on one side, and the wide tape-type sheet materials 33Tc on the rear portion 23 are taken on the other side. By this, in the front portion 21, the intervals with the other tape-type sheet materials 33T on the both sides of the wide tape-type sheet material 33Tc become equivalent to the intervals between many other tape-type sheet materials 33T. Furthermore, also in the rear portion 23, the intervals with the other tape-type sheet materials 33T on the both sides of the wide tape-type sheet material 33Tc become equivalent to the intervals between many other tape-type sheet materials 33T. By this, it becomes possible to make the widths of a part of the tape-type sheet materials 33T wide in the state that the intervals of the tape-type sheet materials 33T are made equivalent.

In this case, for attachment of the tape-type sheet materials 33T to a second sheet material 2S, which is not illustrated, through the elastic member continuous elements 3Sc, the production methods in the above-mentioned first and second embodiments can be applied.

Although, in the above-mentioned third aspect, two pieces of tape-type sheet materials 33Tc are made wide and plural pieces of elastic member continuous elements 3S that correspond to the tape-type sheet materials 33T are disposed, the number of the elastic member continuous elements 3S corresponding to the tape-type sheet materials 33Tc on the front portion 21 and the number of the elastic member continuous elements 3S corresponding to the tape-type sheet materials 33Tc on the rear portion 23 may be different. Furthermore, the elastic member continuous elements 3S having different sizes may be disposed.

For example, in the cases when the elastic member continuous elements 3S are disposed on the waist, ilium bones, lumbar and the like, the numbers of the respective elastic member continuous elements 3S on the front portion 21 and rear portion 23 may be changed. By increasing the number of the elastic member continuous elements 3S, the elastic force can be strengthen, and thus strong constriction force can be obtained. Alternatively, the numbers of the respective elastic member continuous elements 3S on the front portion 21 and rear portion 23 may be different. For example, by adjusting the number of the elastic member continuous elements 3S on the rear portion 23 to be more than that on the front portion 21, the elastic force on the rear portion 23 can be strengthen and the falling off of the diaper can be suppressed. Furthermore, by adjusting the number of the elastic member continuous elements 3S on the front portion 21 to be more than that on the rear portion 23, the elastic force of the front portion 21 can be strengthen and the falling off of the diaper can be suppressed.

Figure 30:
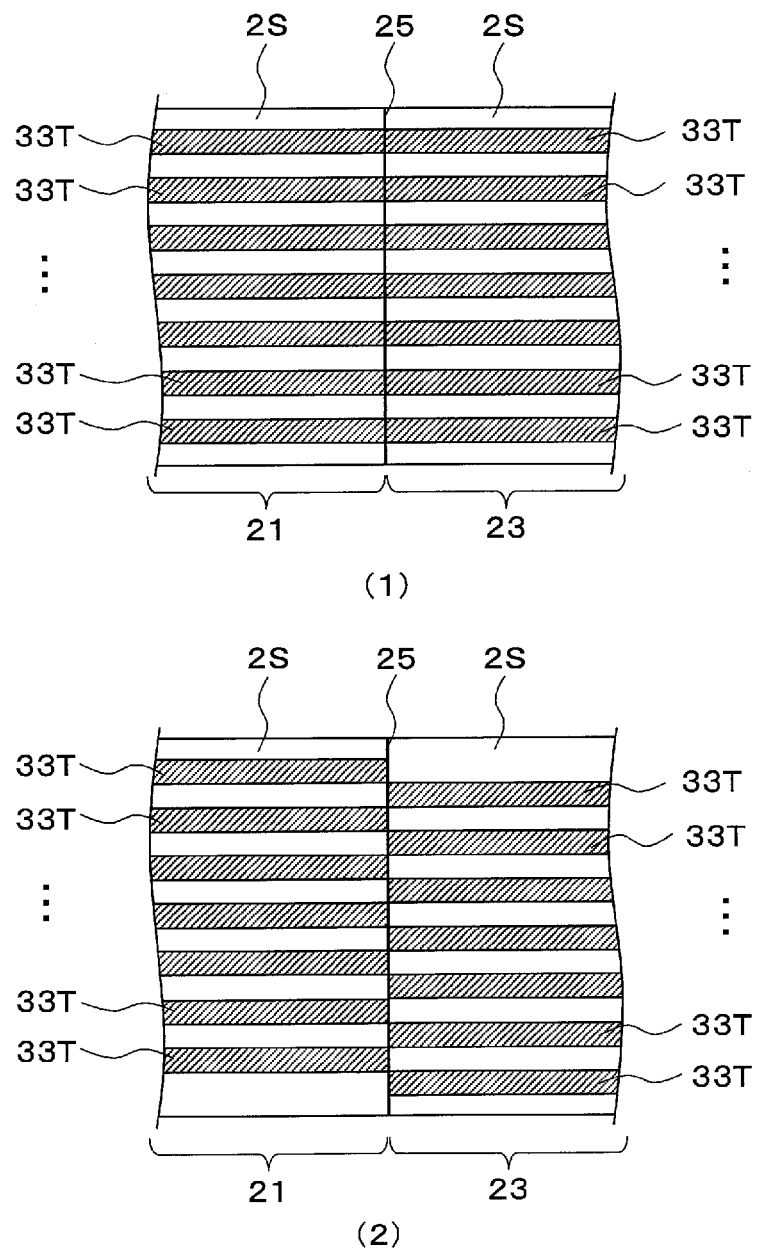
FIG. 30 shows a side view of the main portion showing an example of the positional relationship between the tape-type sheet materials and the second sheet materials for the front portion and the rear portion, on both sides of the side seal portion of the pull-on wear article of the present invention.
Figure 32:
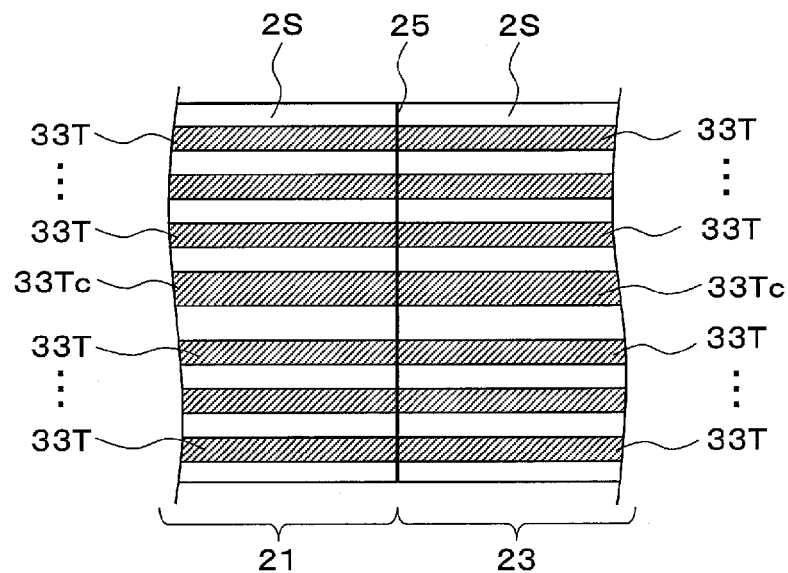
FIG. 32 shows a side view of the main portion showing an example of the positional relationship between the tape-type sheet materials and the second sheet materials for the front portion and the rear portion, on both sides of the side seal portion of the pull-on wear article of the present invention.

Next, the case where a pull-on diaper is made by using tape-type sheet materials 33T slitted into even widths will be explained below, referring to FIG. 30. FIGS. 30 to 32 are shown by describing hatching for easy understanding of the positions of the tape-type sheet materials 33T.

FIG. 30 (1) shows a side view of the main portion of a diaper made by using the tape-type sheet materials 33T slitted into even widths. The numbers of the respective tape-type sheet materials 33T disposed on the front portion 21 and rear portion 23 are the same. The feed positions of the second sheet materials 2S disposed respectively on the rear portion 23 and front portion 21, with respect to the tape-type sheet materials 33T, are adjusted so that the positional relationship between the second sheet material 2S and the tape-type sheet materials 33T on the rear portion 23, and the positional relationship between the second sheet material 2S and the tape-type sheet materials 33T on the front portion 21 become similar. Namely, the distances between the one end side in the lateral direction of the second sheet material 2S and the end side at the side of the above former one end side in the lateral direction of the tape-type sheet material 33T that is the closest to the above former end side are adjusted to be the same. When a diaper is made by using the second sheet material 2S to which the tape-type sheet materials 33T are adhered by this, the tape-type sheet materials 33T adhered to the second sheet material 2S disposed on the front portion 21 and the tape-type sheet materials 33T adhered to the second sheet material 2S disposed on the rear portion 23 are superposed on a side seal portion 25. In this case, the side seal portion 25 has a strong-weak sealing relationship, and thus easiness of peeling on the side seal portion 25 is improved.

In the above-mentioned example, the width of the second sheet material 2S disposed on the front portion 21 and the width of the second sheet material 2S disposed on the rear portion 23 are the same. Hereinafter the same will apply to the widths of the second sheet materials 2S. {0173}

In addition, it is possible to displace the positional relationship between the tape-type sheet materials 33T disposed on the front portion 21 and the tape-type sheet materials 33T disposed on the rear portion 23 in the state that the diaper is made, by changing the feed positions of the second sheet materials 2S with respect to the tape-type sheet material 33T during the adhering of the tape-type sheet materials 33T. For example, by displacing the feed position of the second sheet material 2S by the width of one piece of the tape-type sheet material 33T from the constitution shown in FIG. 30 (1), the tape-type sheet materials 33T adhered to the second sheet material 2S disposed on the rear portion 23 are disposed between the tape-type sheet materials 33T adhered to the second sheet material 2S disposed on the front portion 21 on the side seal portion 25, as shown in FIG. 30(2), and the tape-type sheet materials 33T are not superposed each other. In this case, it is not necessary to adjust the flow of the second sheet material 2S, the processing can be conducted without paying attention to the conveying property of the entirety of the outer cover.

Furthermore, the case where the numbers of the tape-type sheet materials 33T disposed on the front portion 21 and the tape-type sheet materials 33T disposed on the rear portion 23 are different, for example, the case where one is an odd number and the other is an even number will be explained below.

For one example, the case when the number of the tape-type sheet materials 33T disposed on the front portion 21 is six and the number of the tape-type sheet materials 33T disposed on the rear portion 23 is seven will be explained, referring to FIG. 31 (1). In the case where the second sheet material 2S disposed on the front portion 21 and the second sheet material 2S disposed on the rear portion 23, to which the tape-type sheet materials 33T separated by an outer layer material slit cutter (not shown) are attached, are on the same position in a planar view (however, the positions in the height direction are different), the distance a between one end side in the lateral direction of the second sheet material 2S disposed on the rear portion 23 and the end side at the side of the above-mentioned one end side in the lateral direction of the tape-type sheet material 33T that is the closest to that end side, and the distance b between one end side in the lateral direction of the second sheet material 2S disposed on the front portion 21 and the end side at the side of the above-mentioned one end side in the lateral direction of the tape-type sheet material 33T that is the closest to that end side, are different by the width of the tape-type sheet material 33T. The second sheet material 2S was fed with respect to the tape-type sheet materials 33T so as to be disposed in such way, and the second sheet material 2S and the tape-type sheet materials 33T are adhered to each other, and a diaper was made by using the second sheet materials 2S. In this case, the positional relationship between the tape-type sheet materials 33T disposed on the front portion 21 and the tape-type sheet materials 33T disposed on the rear portion 23 is in an alternately-disposed state, and these tape-type sheet materials are not superposed.

Furthermore, the case where the numbers of the tape-type sheet materials 33T disposed on the front portion 21 and rear portion 23 are different as mentioned above will be explained, referring to FIG. 31 (2). This example is the case where the distance a between one end side in the lateral direction of the second sheet material 2S disposed on the rear portion 23 and the end side at the side of the above-mentioned one end side in the lateral direction of the tape-type sheet material 33T that is the closest to that end side, and the distance b between one end side in the lateral direction of the second sheet material 2S disposed on the front portion 21 and the end side at the side of the above-mentioned one end side in the lateral direction of the tape-type sheet material 33T that is the closest to that end side, are the same. The second sheet materials 2S were fed to the tape-type sheet materials 33T so as to be disposed in such way, the second sheet material and the tape-type sheet materials are adhered to each other, and a diaper was made by using the second sheet materials 2S. In this case, the tape-type sheet materials 33T disposed on the front portion 21 and the tape-type sheet materials 33T disposed on the rear portion 23 are superposed on the side seal portion 25 of the diaper. Since the tape-type sheet materials 33T are disposed lesser on the front portion 21 than on the rear portion 23, the tape-type sheet material 33T on the front portion 21, which is not superposed with the tape-type sheet materials 33T on the rear side 23, are generated on the side seal portion 25.

In the cases of the constitutions shown in FIG. 31 (1) and (2), the adjustments of the range of stretch and stress are possible, and the range of freedom of the specification of the outer cover (for example, designing of constriction stress) is broaden. Furthermore, in either constitution, since the tape-type sheet materials 33T on the rear portion 23 are one piece more down below, the fittability to the buttocks is excellent.

Next, the case where a pull-on diaper is made by using tape-type sheet materials 33T comprising tape-type sheet materials 33Tc slitted into different widths will be explained below, referring to FIG. 32.

The side view of the main portion of the diaper shown in FIG. 32 is the case of the tape-type sheet material 33T comprising the tape-type sheet materials 33Tc with different widths shown in FIG. 28, and the feed positions of the second sheet materials 2S with respect to the tape-type sheet materials 33T were adjusted, the second sheet material and the tape-type sheet materials 33T are adhered to each other, and a diaper was made by using these second sheet materials 2S. In this case, the tape-type sheet materials 33T disposed on the front portion 21 and the tape-type sheet materials 33T disposed on the rear portion 23, on the side seal portion 25 of the diaper, are superposed. Furthermore, the tape-type sheet materials 33Tc having different widths are superposed with each other.

Next, another example in which a pull-on diaper is made by using the tape-type sheet materials 33T comprising the tape-type sheet material 33Tc slitted into different widths will be explained below, referring to FIG. 33.

Figure 33:
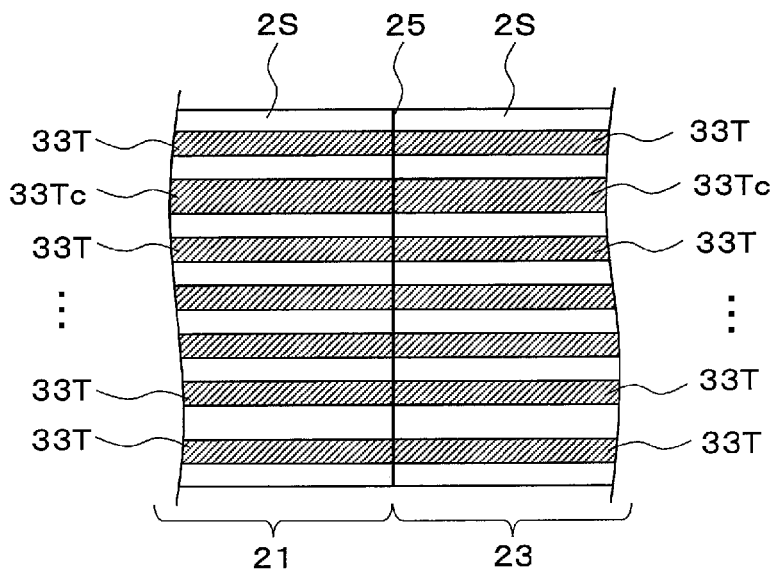
FIG. 33 shows a side view of the main portion showing an example of the positional relationship between the tape-type sheet materials and the second sheet materials for the front portion and the rear portion, on both sides of the side seal portion of the pull-on wear article of the present invention.

The side view of the main portion of the diaper shown in FIG. 33 is the case of the tape-type sheet materials 33T comprising the tape-type sheet materials 33Tc with different widths shown in FIG. 29, and the feed positions of the second sheet materials 2S with respect to the tape-type sheet materials 33T were adjusted, the second sheet material and the tape-type sheet materials are adhered to each other, and a diaper was made by using these second sheet materials 2S. In this case, the tape-type sheet materials 33T disposed on the front portion 21 and the tape-type sheet material 33T disposed on the rear portion 23 are superposed on the side seal portion 25 of the diaper. Furthermore, the tape-type sheet materials 33Tc with different widths are also superposed with each other. In addition, the tape-type sheet materials 33Tc with different widths disposed on the front portion 21 and the tape-type sheet materials 33Tc with different widths disposed on the rear portion 23 are superposed on the side seal portion 25. In addition, the positions between the tape-type sheet materials 33T, which correspond to the positions from which the tape-type sheet materials 33T with different widths have been removed, are also superposed.

Next, a method for adjusting the positions of the respective outer cover continuous elements 11S disposed on the front portion 21 and rear portion 23 to give a predetermined interval D in the embodiments explained in the above-mentioned FIGS. 24 to 27 will be explained. Examples of this method include, adding to a method by a combination of the above-mentioned rolls, a method comprising feeding the second sheet 2S disposed on the rear side and the second sheet 2S disposed on the front side so that the tape-type sheet materials 33T are disposed on the surface side and feeding the two second sheets 2S in the parallel direction by using a spacing means (not shown), in a similar manner to the method for producing the pull-on diaper 10 as explained by the above-mentioned FIGS. 10 to 13. In this method, the height of the second sheet material 2S disposed on the rear side and the height of the second sheet material 2S disposed on the front side are different, and the difference in height may be adjusted to the same height by using, for example, two rolls (not shown).

Figure 34:
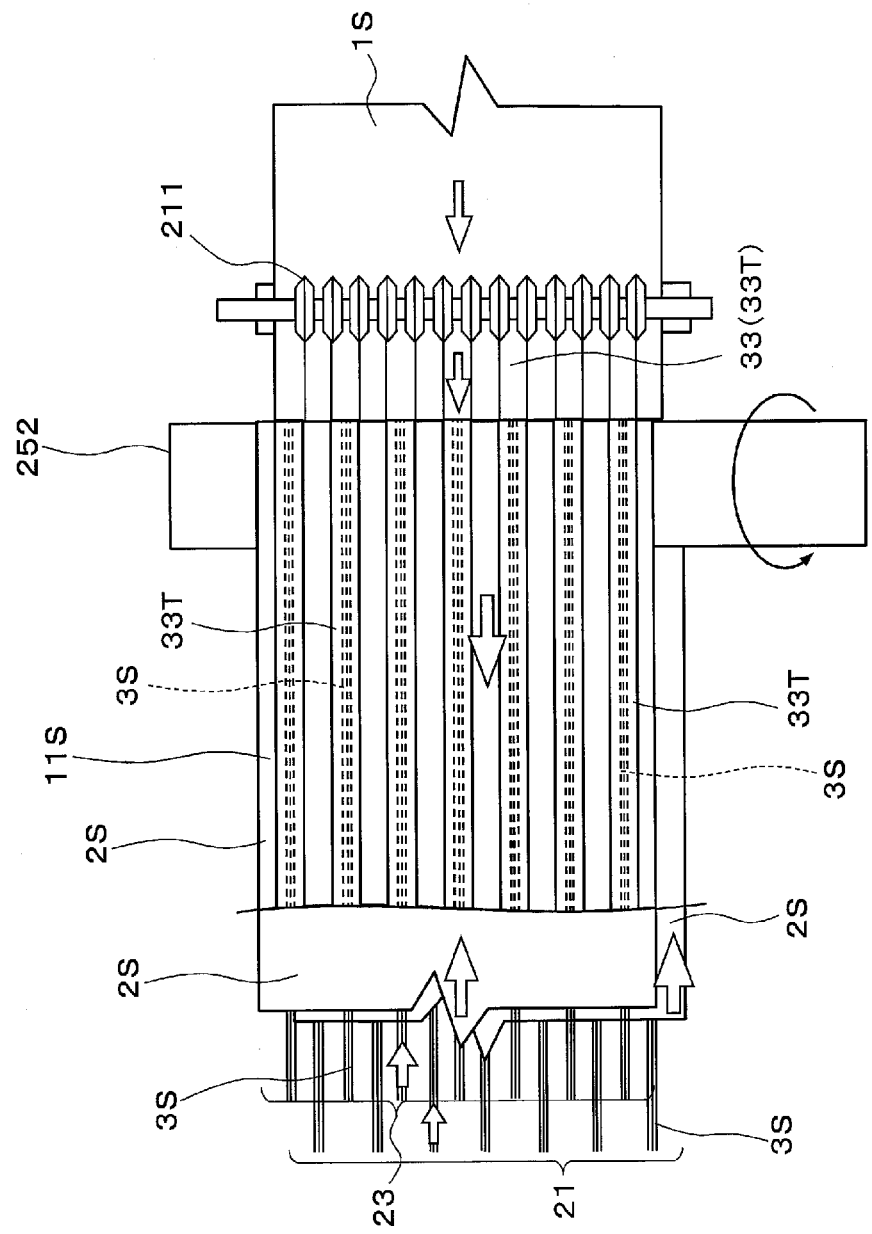
FIG. 34 shows a drawing showing the sixth embodiment according to the method for producing a pull-on wear article of the present invention, which is a plane view of the main portion showing the case where plural pieces of elastic member continuous elements 3S are fed each in plural pieces in FIG. 21 (1) of the first embodiment.

Next, the fourth embodiment according to the method for producing a pull-on wear article of the present invention will be explained, with referring to FIG. 34. FIG. 34 is a plane view of the main portion showing the case where plural pieces of elastic member continuous elements 3S are fed each time in FIG. 21 (1) of the above-mentioned first embodiment, unlike the above-mentioned first to third embodiments. Furthermore, the fourth embodiment utilizes the maintaining of the intervals of the tape-type sheet materials 33T without misalignment from the slitting to the adhering to the second sheet material 2S in the above-mentioned first to third embodiments.

As shown in FIG. 34, it becomes possible to feed plural pieces of thin elastic member continuous element 3S to one tape-type sheet material 33T, and adhere the second sheet material 2S to the tape-type sheet material 33T by interposing the plural pieces of thin elastic member continuous elements 3S therebetween. At this time, it is preferable to consider the width and number of the thin elastic member continuous elements 3S so that elastic force similar to elastic force of an elastic member continuous element 3S constituted by one piece can be obtained. Furthermore, since the positions of the tape-type sheet materials 33T in the lateral direction during the slitting are maintained, the adjusting the positions of the tape-type sheet materials 33T is conducted with high precision; therefore, even plural pieces of the thin elastic member continuous elements 3S are adhered to one piece of the tape-type sheet material 33T, the adhesion can be conducted so that the elastic member continuous elements 3S fit in the width of the tape-type sheet material 33T without running off the tape-type sheet material 33T.

Therefore, since plural pieces of the thin elastic member continuous elements 3S can be adhered to one piece of the tape-type sheet material 33T, the elastic member continuous elements 3S can be made more difficult to be seen by being made thin without decreasing the stretch force, a wearer is made more unconscious of the constriction force by the elastic members (the elastic member continuous elements 3S), and the wearing comfort can be improved.

For example, although it depends on the tape-type sheet material 33T, in the case where the tape-type sheet material 33T having a basis weight of about 16 g/m² and a thickness of about 0.02 mm is used, the elastic member continuous elements 3S becomes difficult to be seen by using each one having a width of about 0.1 mm to 1 mm and adjusting the intervals thereof to about 1 mm to 5 mm, and it is preferable that the width is adjusted to about 0.1 mm to 0.3 mm and the intervals thereof are adjusted to about 2 mm to 4 mm.

The above-mentioned respective embodiments and respective aspects can be suitably combined.

For example, the fourth embodiment can be combined with the above-mentioned first to third embodiments.

The case where the second aspect of the above-mentioned third embodiment and the fourth embodiment mentioned above are combined will be explained. For example, in the first sheet material 1S, for the portions from which the tape-type sheet materials 33Tc have been removed for the front portion 21, intervals that correspond to the tape-type sheet materials 33Tc are formed on the rear portion 23. Therefore, the elastic force is weak at those portions on the rear portion 23. Therefore, by adhering plural pieces of the elastic member continuous elements 3S to the portions of the tape-type sheet materials 33T that are adjacent to the both sides of the portions at which the interval of the tape-type sheet materials 33T is broad on the rear portion 23, the elastic force on those portions can be strengthen to thereby cover decreasing of the elastic force at the portions where the intervals of the tape-type sheet materials 33T are broaden.

Although a pull-on diaper is exemplified as the pull-on wear article of the present invention in the above-mentioned respective embodiments, a pull-on diaper cover used to dispose an absorbent body on the skin-surface side is also preferable. The absorbent body is not specifically limited as long as it absorbs discharged urine and the like, and examples may include absorbent pads such as urine pads. Examples of the absorbent pads may include an absorbent pad comprising a liquid-permeable topsheet, a liquid-impermeable leak-preventive sheet, and a liquid-retainable absorbent core that is interposed between the two sheets, and formed into a longitudinal long shape such as a rectangular shape in a planar view. Furthermore, it is preferable that a matched pair of three-dimensional guards is formed on the both sides in the longitudinal direction of the absorbent pad, and it is preferable that sheet materials having three-dimensional guard elastic elements for forming the three-dimensional guards are disposed on the both sides of the longitudinal direction of the absorbent pad as the respective steric guards. Such absorbent pad is disposed so that the longitudinal direction would bridge between the rear side and front side of a wearer through the crotch to thereby dispose the liquid permeable sheet side of the pad so as to contact with the skin of the wearer. It is preferable that the diaper cover is worn so as to wrap the absorbent pad.

Furthermore, the pull-on wear article of the present invention is a concept that comprises general absorbent articles having a pull-on structure such as sanitary shorts and shorts type napkins, besides the pull-on diapers mentioned above. The pull-on wear article may be either for infants or for adult humans.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2010-291843 filed in Japan on Dec. 28, 2010, and Patent Application No. 2011-243227 filed in Japan on Nov. 7, 2011, each of which is entirely herein incorporated by reference.

With respect to the above-mentioned embodiments, the present invention further discloses the pull-on wear articles or methods of producing a pull-on wear article mentioned below.

<1> A pull-on wear article having a front portion that is adapted to be worn around the front side of a wearer, a crotch portion that is adapted to be worn along the wearer's crotch region, and a rear portion that is adapted to be worn around the wearer's rear side, which is formed into a pants form by bonding lateral side edges of the front portion and lateral side edges of the rear portion, wherein the front portion and the rear portion are each constituted by an outer cover in which an inner layer material and an outer layer material are laminated, the outer cover has plural single layer areas that are formed of the inner layer material or the outer layer material at intervals in the direction of length of the outer cover, and the laminate areas where the inner layer material and outer layer material are laminated have elasticity in the waist-surrounding direction of the outer cover.

<2> The pull-on wear article according to the above-mentioned <1>, wherein the inner layer material is present in the single layer areas, and the outer layer material is laminated on the inner layer material at intervals in the lateral direction of the outer cover.

<3> The pull-on wear article according to the above-mentioned <1> or <2>, wherein the laminate areas each has an elastic member between the inner layer material and the outer layer material, or both or one of the inner layer material and the outer layer materials is/are formed of a elastic material.

<4> The pull-on wear article according to any one of the above-mentioned <1> to <3>, wherein the outer cover has undergone a stretching processing.

<5> The pull-on wear article according to any one of the above-mentioned <1> to <4>, wherein the outer layer material in the laminate areas is fixed to the inner layer material at the central portion in the lateral direction of the outer layer material, and frills are formed on the edge portions that are free ends of the outer layer material.

<6> A method for producing a pull-on wear article, comprising:

a step of slitting a first sheet material for constituting an outer cover at plural points in a lateral direction to form plural pieces of tape-type sheet materials;

a step of laminating and fixing the plural pieces of tape-type sheet materials at spaced intervals with second sheet materials to give the outer cover;

a step of orienting the second sheet materials to face inward and thereby overlapping the outer cover, and bonding the overlapped outer cover at a predetermined interval in the lateral direction of the outer cover; and a step of cutting the outer cover at the bonded portions in the lateral direction.

<7> The method for producing a pull-on wear article according to the above-mentioned <6>, wherein the plural pieces of tape-type sheet materials are spaced apart in the lateral direction by a spacing means.

<8> The method for producing a pull-on wear article according to the above mentioned <6> or <7>, wherein the first sheet and second sheet in an area where an elastic member is absent are emboss-bonded in the state that the elastic member is interposed between the first sheet material and the second sheet material.

<9> The method for producing a pull-on wear article according to any of the above-mentioned <6> to <8>, wherein a stretching processing is conducted on either one or both of the first sheet material and second sheet material before laminating the first sheet material and second sheet material, or after putting the first sheet material and second sheet material into the laminated state.

<10> A method for producing a pull-on wear article, comprising:
  a step of slitting a first sheet material for constituting an outer cover at plural points in a lateral direction to form plural pieces of tape-type sheet materials;
  a step of conveying the plural pieces of tape-type sheet materials alternately in different directions while maintaining the positions in the lateral direction during the slitting to thereby separate the tape-type sheet materials into tape-type sheet materials for the front side and tape-type sheet materials for the rear side;
  a step of laminating and fixing the respective tape-type sheet materials for the front side and for the rear side with separate second sheet materials for the front side and rear side while maintaining the positions in the lateral direction during the slitting to give an outer cover continuous element to be disposed on the front portion and an outer cover continuous element to be disposed on the rear portion;
  a step of adjusting their positions of the outer cover continuous element to be disposed on the front portion and the outer cover continuous element to be disposed on the rear portion to give a predetermined interval;
  a step of fixing an absorbent body so as to bridge between the outer cover continuous element to be disposed on the front portion and the outer cover continuous element to be disposed on the rear portion;
  a step of orienting the second sheet materials to face inward and thereby overlapping the outer cover continuous element to be disposed on the front portion and the outer cover continuous element to be disposed on the rear portion, and bonding the outer cover continuous elements at a predetermined interval in the lateral direction; and
  a step of cutting the outer cover continuous elements in the lateral direction at the bonded portions.

<11> The method for producing a pull-on wear article according to the above-mentioned <10>, wherein the step of separating the tape-type sheet materials into the tape-type sheet materials for the front side and the tape-type sheet materials for the rear side comprises selecting the plural pieces of tape-type sheet materials one by one alternately and winding the selected tape-type sheet material around each roll of a pair of separation rolls to thereby separate and convey the tape-type sheet materials in the different directions.

<12> The method for producing a pull-on wear article according to the above-mentioned <11>, wherein the tape-type sheet materials for the front side that wind around one of the pair of separation rolls are laminated on the second sheet material for the front side while maintaining their winding state, and the tape-type sheet materials for the rear side that wind around the other separation roll are laminated on the second sheet material for the rear side while maintaining their winding state.

<13> The method for producing a pull-on wear article according to any of the above-mentioned <10> to <12>, wherein the spacing interval of the tape-type sheet materials is the same as the width of the tape-type sheet material.

<14> The method for producing a pull-on wear article according to any of the above-mentioned <6>, <7> and <10> to <13>, wherein the tape-type sheet materials and the second sheet materials are bonded with interposing an elastic member continuous element therebetween.

<15> The method for producing a pull-on wear article according to any of the above-mentioned <10> to <14>, wherein the step of adjusting the positions of the respective outer cover continuous elements for the front portion and rear portion to give a predetermined interval comprises disposing the surface on the side of the second sheet material for the front portion and the surface on the side of the second sheet material for the rear portion in the same planar direction and at the same height.

<16> The method for producing a pull-on wear article according to any of the above-mentioned <10> to <15>, wherein the step of adjusting the positions of the respective outer cover continuous elements for the front portion and rear portion at a predetermined interval is conducted by two rolls that are configured to transfer, in parallel, the feed direction of one of the respective outer cover continuous elements for the front portion and the rear portion, and by two rolls that are configured to adjust the feeding height of one of the outer cover continuous elements.

INDUSTRIAL APPLICABILITY

The pull-on wear article of the present invention can soften the waist-surrounding area by the action of the portions of the single layer areas, and can markedly increase the air permeability in those areas and can significantly reduce steaminess, while maintaining similar elasticity to that of a conventional pull-on wear article to thereby retain the fittability to the body of a wearer and the movability to follow the motion of the wearer's body.

According to the method for producing a pull-on wear article of the present invention, a pull-on wear article in which the above-mentioned elasticity, fittability to the body, air permeability and the like are improved can be easily produced.

The method for producing a pull-on wear article of the present invention can easily produce a pull-on wear article that can soften the waist-surrounding area by the action of the portions of the single layer areas, and can markedly increase the air permeability at those areas and can significantly reduce steaminess.

Furthermore, since the tape-type sheet materials for the front side and for the rear side are respectively laminated and fixed on the second sheet materials while their positions in the lateral direction during slitting are maintained, the tape-type sheet materials can be stably disposed on the second sheet materials with high precision.

DESCRIPTION OF SYMBOLS

10 Pull-on wear article (Pull-on diaper)
11 Outer cover
11S Outer cover continuous element
13 Crotch portion
21 Front portion
21A, 21B Lateral side edge
23 Rear portion
23A, 23B Lateral side edge
31 Inner layer material
33 Outer layer material
35 Elastic member
1S First sheet material
2S Second sheet materials
3S Elastic member continuous elements
33T,33Tc Tape-type sheet materials 33T

The invention claimed is:
1. A pull-on wear article having a front portion that is adapted to be worn around the front side of a wearer, a crotch portion that is adapted to be worn along the wearer's crotch region, and a rear portion that is adapted to be worn around the wearer's rear side, which is formed into a pants form by bonding lateral side edges of the front portion and lateral side edges of the rear portion, wherein the front portion and the rear portion are each constituted by an outer cover in which an inner layer material and an outer layer material are laminated, the outer cover has plural single layer areas that are formed of the inner layer material or the outer layer material at intervals in the direction of length of the outer cover, and the laminate areas where the inner layer material and outer layer material are laminated have elasticity in the waist-surrounding direction of the outer cover.

2. The pull-on wear article according to claim 1, wherein the inner layer material is present in the single layer areas, and the outer layer material is laminated on the inner layer material at intervals in the lateral direction of the outer cover.

3. The pull-on wear article according to claim 1, wherein the laminate areas each has an elastic member between the inner layer material and the outer layer material, or both or one of the inner layer material and the outer layer materials is/are formed of an elastic material.

4. The pull-on wear article according to claim 1, wherein the outer cover has undergone a stretching processing.

5. The pull-on wear article according to claim 1, wherein the outer layer material in the laminate areas is fixed to the inner layer material at the central portion in the lateral direction of the outer layer material, and frills are formed on the edge portions that are free ends of the outer layer material.

\* \* \* \* \*